(12) United States Patent
Fischell et al.

(10) Patent No.: US 10,420,481 B2
(45) Date of Patent: *Sep. 24, 2019

(54) APPARATUS FOR EFFECTIVE ABLATION AND NERVE SENSING ASSOCIATED WITH DENERVATION

(71) Applicant: Ablative Solutions, Inc., Palo Alto, CA (US)

(72) Inventors: David R. Fischell, Fair Haven, NJ (US); Tim A. Fischell, Kalamazoo, MI (US); Vartan Ghazarossian, Menlo Park, CA (US); Steven Almany, Bloomfield Hills, MI (US); Michael Sasha John, Larchmont, NY (US)

(73) Assignee: Ablative Solutions, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/034,854

(22) Filed: Jul. 13, 2018

(65) Prior Publication Data

US 2019/0015002 A1 Jan. 17, 2019

Related U.S. Application Data

(63) Continuation of application No. 15/663,409, filed on Jul. 28, 2017, now Pat. No. 10,022,059, which is a (Continued)

(51) Int. Cl.
*A61B 3/02* (2006.01)
*A61B 5/04* (2006.01)
(Continued)

(52) U.S. Cl.
CPC ........ *A61B 5/04001* (2013.01); *A61B 5/4035* (2013.01); *A61B 5/6848* (2013.01);
(Continued)

(58) Field of Classification Search
CPC ... A61B 5/065; A61B 5/0422; A61B 18/1492; A61B 5/6852; A61B 2018/00267;
(Continued)

(56) References Cited

U.S. PATENT DOCUMENTS

| 4,578,061 A | 3/1986 | Lemelson |
| 4,798,595 A | 1/1989 | Anderson et al. |

(Continued)

FOREIGN PATENT DOCUMENTS

| CN | 1147964 | 4/1997 |
| CN | 1494399 | 5/2004 |

(Continued)

OTHER PUBLICATIONS

U.S. Appl. No. 15/940,178, filed Mar. 29, 2018, Fischell, et al.

(Continued)

*Primary Examiner* — Joseph A Stoklosa
*Assistant Examiner* — Brian M Antiskay
(74) *Attorney, Agent, or Firm* — Knobbe, Martens, Olson & Bear, LLP

(57) ABSTRACT

An intravascular catheter for nerve activity ablation and/or sensing includes one or more needles advanced through supported guide tubes (needle guiding elements) which expand to contact the interior surface of the wall of the renal artery or other vessel of a human body allowing the needles to be advanced though the vessel wall into the extra-luminal tissue including the media, adventitia and periadvential space. The catheter also includes structures which provide radial and lateral support to the guide tubes so that the guide tubes open uniformly and maintain their position against the interior surface of the vessel wall as the sharpened needles are advanced to penetrate into the vessel wall. Electrodes near the distal ends of the needles allow sensing of nerve activity before and after attempted renal denervation. In a (Continued)

combination embodiment ablative energy or fluid is delivered from the needles in or near the adventitia to ablate nerves outside of the media while sparing nerves within the media.

21 Claims, 21 Drawing Sheets

Related U.S. Application Data continuation of application No. 14/963,179, filed on Dec. 8, 2015, now Pat. No. 9,949,652, which is a continuation-in-part of application No. 14/063,907, filed on Oct. 25, 2013, now Pat. No. 9,931,046.

(51) Int. Cl.

| | |
|---|---|
| *A61M 31/00* | (2006.01) |
| *A61B 5/00* | (2006.01) |
| *A61B 18/14* | (2006.01) |
| *A61B 17/32* | (2006.01) |
| *A61B 5/20* | (2006.01) |
| *A61B 18/18* | (2006.01) |
| *A61B 18/00* | (2006.01) |
| *A61B 18/02* | (2006.01) |
| *A61B 18/04* | (2006.01) |
| *A61M 25/00* | (2006.01) |
| *A61B 90/00* | (2016.01) |
| *A61B 18/12* | (2006.01) |
| *A61B 17/00* | (2006.01) |

(52) U.S. Cl.
CPC ........ *A61B 5/6852* (2013.01); *A61B 18/1492* (2013.01); *A61B 5/201* (2013.01); *A61B 17/320068* (2013.01); *A61B 18/0218* (2013.01); *A61B 18/1233* (2013.01); *A61B 18/1477* (2013.01); *A61B 18/1815* (2013.01); *A61B 2017/00039* (2013.01); *A61B 2018/00214* (2013.01); *A61B 2018/00404* (2013.01); *A61B 2018/00434* (2013.01); *A61B 2018/00541* (2013.01); *A61B 2018/00577* (2013.01); *A61B 2018/00642* (2013.01); *A61B 2018/00666* (2013.01); *A61B 2018/00738* (2013.01); *A61B 2018/00779* (2013.01); *A61B 2018/00815* (2013.01); *A61B 2018/00821* (2013.01); *A61B 2018/00827* (2013.01); *A61B 2018/00839* (2013.01); *A61B 2018/00875* (2013.01); *A61B 2018/00892* (2013.01); *A61B 2018/00898* (2013.01); *A61B 2018/00916* (2013.01); *A61B 2018/0212* (2013.01); *A61B 2018/046* (2013.01); *A61B 2018/048* (2013.01); *A61B 2018/143* (2013.01); *A61B 2018/1425* (2013.01); *A61B 2018/1432* (2013.01); *A61B 2018/1467* (2013.01); *A61B 2018/1475* (2013.01); *A61B 2090/376* (2016.02); *A61B 2090/3966* (2016.02); *A61M 2025/0095* (2013.01)

(58) Field of Classification Search
CPC .............. A61B 5/6859; A61B 19/5244; A61B 2018/00214; A61B 2017/003; A61B 5/6848; A61B 2018/1425
USPC ................ 600/372–375, 378, 381, 466–467; 607/115, 118–119, 126, 128, 133
See application file for complete search history.

(56) References Cited

U.S. PATENT DOCUMENTS

| | | |
|---|---|---|
| 5,304,141 A | 4/1994 | Johnson et al. |
| 5,354,279 A | 10/1994 | Hofling |
| 5,385,562 A | 1/1995 | Adams et al. |
| 5,405,376 A | 4/1995 | Mulier |
| 5,419,777 A | 5/1995 | Hofling |
| 5,464,395 A | 11/1995 | Faxon et al. |
| 5,474,102 A | 12/1995 | Lopez |
| 5,551,426 A | 9/1996 | Hummel et al. |
| 5,588,960 A | 12/1996 | Edwards et al. |
| 5,667,488 A | 9/1997 | Lundquist et al. |
| 5,672,173 A | 9/1997 | Gough |
| 5,683,384 A | 11/1997 | Gough |
| 5,713,863 A | 2/1998 | Vigil et al. |
| 5,792,094 A | 8/1998 | Stevens et al. |
| 5,800,379 A | 9/1998 | Edwards |
| 5,855,576 A | 1/1999 | LeVeen et al. |
| 5,902,289 A | 5/1999 | Swartz et al. |
| 5,971,958 A | 10/1999 | Zhang |
| 5,980,516 A | 11/1999 | Mulier et al. |
| 6,056,744 A | 5/2000 | Edwards |
| 6,106,521 A | 8/2000 | Blewett et al. |
| 6,165,164 A | 12/2000 | Hill et al. |
| 6,190,353 B1 | 2/2001 | Makower et al. |
| 6,190,393 B1 | 2/2001 | Bevier et al. |
| 6,217,554 B1 | 4/2001 | Green |
| 6,221,049 B1 | 4/2001 | Selmon et al. |
| 6,231,597 B1 | 5/2001 | Deem et al. |
| 6,254,599 B1 | 7/2001 | Lesh et al. |
| 6,277,107 B1 | 8/2001 | Lurie et al. |
| 6,283,947 B1 | 9/2001 | Mirzaee |
| 6,283,951 B1 | 9/2001 | Flaherty et al. |
| 6,302,870 B1 | 10/2001 | Jacobsen et al. |
| 6,375,660 B1 | 4/2002 | Fischell et al. |
| 6,416,510 B1 | 7/2002 | Altman et al. |
| 6,432,092 B2 | 8/2002 | Miller |
| 6,478,778 B1 | 11/2002 | Jacobsen et al. |
| 6,514,248 B1 | 2/2003 | Eggers et al. |
| 6,547,803 B2 | 4/2003 | Seward et al. |
| 6,599,267 B1 | 7/2003 | Ray et al. |
| 6,652,517 B1 | 11/2003 | Hall et al. |
| 6,685,648 B2 | 2/2004 | Flaherty et al. |
| 6,692,466 B1 | 2/2004 | Chow et al. |
| 6,764,461 B2 | 7/2004 | Mickley et al. |
| 6,854,467 B2 | 2/2005 | Boekstegers |
| 6,855,124 B1 | 2/2005 | Gonzalez et al. |
| 6,905,480 B2 | 6/2005 | McGuckin et al. |
| 6,966,897 B2 | 11/2005 | Shimazaki |
| 6,978,174 B2 | 12/2005 | Gelfand et al. |
| 6,997,903 B2 | 2/2006 | Wijay et al. |
| 7,015,253 B2 | 3/2006 | Escandon et al. |
| 7,056,286 B2 | 6/2006 | Ravenscroft et al. |
| 7,087,040 B2 | 8/2006 | McGuckin, Jr. et al. |
| 7,094,202 B2 | 8/2006 | Nobis et al. |
| 7,162,303 B2 | 1/2007 | Levin et al. |
| 7,181,288 B1 | 2/2007 | Rezai et al. |
| 7,273,469 B1 | 9/2007 | Chan et al. |
| 7,472,705 B2 | 1/2009 | Baran |
| 7,617,005 B2 | 11/2009 | Demarais et al. |
| 7,621,945 B2 | 11/2009 | Lennox et al. |
| 7,647,115 B2 | 1/2010 | Levin et al. |
| 7,653,438 B2 | 1/2010 | Deem et al. |
| 7,666,163 B2 | 2/2010 | Seward et al. |
| 7,691,080 B2 | 4/2010 | Seward et al. |
| 7,691,086 B2 | 4/2010 | Tkebuchava |
| 7,717,899 B2 | 5/2010 | Bowe et al. |
| 7,717,948 B2 | 5/2010 | Demarais et al. |
| 7,744,584 B2 | 6/2010 | Seward et al. |
| 7,756,583 B2 | 7/2010 | Demarais et al. |
| 7,794,444 B2 | 9/2010 | Lesh et al. |
| 7,850,656 B2 | 12/2010 | McKay et al. |
| 7,862,563 B1 | 1/2011 | Cosman et al. |
| 7,873,417 B2 | 1/2011 | Demarais et al. |
| 7,881,807 B2 | 2/2011 | Schaer |
| 7,942,854 B1 | 5/2011 | Von Oepen et al. |
| 8,000,764 B2 | 8/2011 | Rashidi |

(56) References Cited

U.S. PATENT DOCUMENTS

| | | |
|---|---|---|
| 8,100,883 B1 | 1/2012 | Johnson |
| 8,131,371 B2 | 3/2012 | Demarals et al. |
| 8,131,372 B2 | 3/2012 | Levin et al. |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,758 B2 | 4/2012 | Chan et al. |
| 8,152,804 B2 | 4/2012 | Elmouelhi et al. |
| 8,175,711 B2 | 5/2012 | Demarais et al. |
| 8,396,548 B2 | 3/2013 | Perry et al. |
| 8,399,443 B2 | 3/2013 | Seward et al. |
| 8,465,451 B2 | 6/2013 | McRae et al. |
| 8,465,752 B2 | 6/2013 | Seward |
| 8,663,190 B2 | 3/2014 | Fischell et al. |
| 8,684,998 B2 | 4/2014 | Demarais et al. |
| 8,708,995 B2 | 4/2014 | Seward et al. |
| 8,740,849 B1 | 6/2014 | Fischell et al. |
| 8,771,252 B2 | 7/2014 | Gelfand et al. |
| 8,852,163 B2 | 10/2014 | Deem et al. |
| 8,880,186 B2 | 11/2014 | Levin et al. |
| 8,934,978 B2 | 1/2015 | Deem et al. |
| 8,948,865 B2 | 2/2015 | Zarins et al. |
| 8,975,233 B2 | 3/2015 | Stein et al. |
| 8,979,801 B2 | 3/2015 | Lamson et al. |
| 8,983,595 B2 | 3/2015 | Levin et al. |
| 9,011,879 B2 | 4/2015 | Seward |
| 9,056,185 B2 | 6/2015 | Fischell et al. |
| 9,125,661 B2 | 9/2015 | Deem et al. |
| 9,131,978 B2 | 9/2015 | Zarins et al. |
| 9,131,983 B2 | 9/2015 | Fischell et al. |
| 9,138,281 B2 | 9/2015 | Zarins et al. |
| 9,179,962 B2 | 11/2015 | Fischell et al. |
| 9,192,715 B2 | 11/2015 | Gelfand et al. |
| 9,199,065 B2 | 12/2015 | Seward |
| 9,237,925 B2 | 1/2016 | Fischell et al. |
| 9,254,360 B2 | 2/2016 | Fischell et al. |
| 9,265,558 B2 | 2/2016 | Zarins et al. |
| 9,278,196 B2 | 3/2016 | Fischell et al. |
| 9,289,255 B2 | 3/2016 | Deem et al. |
| 9,301,795 B2 | 4/2016 | Fischell et al. |
| 9,308,044 B2 | 4/2016 | Zarins et al. |
| 9,314,630 B2 | 4/2016 | Levin et al. |
| 9,320,561 B2 | 4/2016 | Zarins et al. |
| 9,320,850 B2 | 4/2016 | Fischell et al. |
| 9,326,817 B2 | 5/2016 | Zarins et al. |
| 9,439,726 B2 | 9/2016 | Zarins et al. |
| 9,456,869 B2 | 10/2016 | Zarins et al. |
| 9,474,563 B2 | 10/2016 | Zarins et al. |
| 9,486,270 B2 | 11/2016 | Zarins et al. |
| 9,526,827 B2 | 12/2016 | Fischell et al. |
| 9,539,047 B2 | 1/2017 | Fischell et al. |
| 9,554,849 B2 | 1/2017 | Fischell et al. |
| 9,629,675 B2 | 4/2017 | Kleshinski et al. |
| 9,636,174 B2 | 5/2017 | Zarins et al. |
| 9,675,413 B2 | 6/2017 | Deem et al. |
| 9,743,983 B2 | 8/2017 | Levin et al. |
| 9,757,192 B2 | 9/2017 | Levin et al. |
| 9,789,276 B2 | 10/2017 | Seward et al. |
| 9,795,441 B2 | 10/2017 | Fischell et al. |
| 9,814,873 B2 | 11/2017 | Zarins et al. |
| 9,895,195 B2 | 2/2018 | Zarins et al. |
| 9,907,611 B2 | 3/2018 | Levin et al. |
| 9,931,046 B2 | 4/2018 | Fischell et al. |
| 9,949,652 B2 | 4/2018 | Fischell et al. |
| 9,993,278 B2 | 6/2018 | Rioux et al. |
| 10,022,059 B2 | 7/2018 | Fischell et al. |
| 10,118,004 B2 | 11/2018 | Fischell et al. |
| 10,172,663 B2 | 1/2019 | Fischell et al. |
| 2001/0037065 A1 | 11/2001 | Graf et al. |
| 2002/0010439 A1 | 1/2002 | Miller |
| 2002/0052577 A1 | 5/2002 | Shimazaki et al. |
| 2002/0082584 A1 | 6/2002 | Rosenman et al. |
| 2002/0120238 A1 | 8/2002 | McGuckin et al. |
| 2002/0151866 A1 | 10/2002 | Lundkvist et al. |
| 2002/0177846 A1 | 11/2002 | Mulier et al. |
| 2002/0183738 A1 | 12/2002 | Chee et al. |
| 2003/0032929 A1 | 2/2003 | McGuckin, Jr. |
| 2003/0171723 A1 | 9/2003 | Ponzi |
| 2004/0064098 A1 | 4/2004 | Cuschieri et al. |
| 2004/0133154 A1 | 7/2004 | Flaherty et al. |
| 2004/0147902 A1 | 7/2004 | McGuckin, Jr. et al. |
| 2005/0070885 A1 | 3/2005 | Nobis et al. |
| 2005/0096647 A1 | 5/2005 | Steinke et al. |
| 2005/0187546 A1 | 8/2005 | Bek et al. |
| 2005/0234437 A1 | 10/2005 | Baxter et al. |
| 2005/0245923 A1 | 11/2005 | Christopherson et al. |
| 2005/0288730 A1 | 12/2005 | Deem et al. |
| 2006/0064065 A1 | 3/2006 | Russo |
| 2006/0173440 A1 | 8/2006 | Lamson et al. |
| 2006/0189940 A1 | 8/2006 | Kirsch |
| 2006/0224118 A1 | 10/2006 | Morris et al. |
| 2006/0271111 A1 | 11/2006 | Demarais et al. |
| 2006/0271135 A1 | 11/2006 | Minar et al. |
| 2007/0060812 A1 | 3/2007 | Harel et al. |
| 2007/0083239 A1 | 4/2007 | Demarias et al. |
| 2007/0129720 A1 | 6/2007 | Demarais et al. |
| 2007/0129760 A1 | 6/2007 | Demarais et al. |
| 2007/0173899 A1 | 7/2007 | Levin et al. |
| 2007/0203549 A1 | 8/2007 | Demarais et al. |
| 2007/0244479 A1 | 10/2007 | Beatty et al. |
| 2007/0270751 A1 | 11/2007 | Stangenes |
| 2007/0270757 A1 | 11/2007 | Willis et al. |
| 2008/0045890 A1 | 2/2008 | Seward et al. |
| 2008/0051756 A1 | 2/2008 | Makower et al. |
| 2008/0188812 A1 | 8/2008 | Valaie |
| 2008/0213331 A1 | 9/2008 | Gelfand et al. |
| 2008/0300454 A1 | 12/2008 | Goto |
| 2009/0018526 A1 | 1/2009 | Power |
| 2009/0018638 A1 | 1/2009 | Shirley et al. |
| 2009/0036948 A1 | 2/2009 | Levin et al. |
| 2009/0076500 A1 | 3/2009 | Azure |
| 2009/0312617 A1 | 12/2009 | Creed et al. |
| 2010/0076545 A1 | 3/2010 | Kleshinski et al. |
| 2010/0114087 A1 | 5/2010 | Edwards |
| 2010/0137860 A1 | 6/2010 | Demarais et al. |
| 2010/0137952 A1 | 6/2010 | Demarais et al. |
| 2010/0179416 A1 | 7/2010 | Hoey et al. |
| 2010/0191112 A1 | 7/2010 | Demarais et al. |
| 2010/0222851 A1 | 9/2010 | Deem et al. |
| 2010/0268307 A1 | 10/2010 | Demarais et al. |
| 2010/0305546 A1 | 12/2010 | Seward et al. |
| 2011/0009848 A1 | 1/2011 | Woodard et al. |
| 2011/0104060 A1 | 5/2011 | Seward |
| 2011/0104061 A1 | 5/2011 | Seward |
| 2011/0112400 A1 | 5/2011 | Emery et al. |
| 2011/0146674 A1 | 6/2011 | Roschak |
| 2011/0182912 A1 | 7/2011 | Evans et al. |
| 2011/0184337 A1 | 7/2011 | Evans et al. |
| 2011/0195971 A1 | 8/2011 | Cincotta |
| 2011/0202098 A1 | 8/2011 | Demarais et al. |
| 2011/0207758 A1 | 8/2011 | Sobotka et al. |
| 2011/0208096 A1 | 8/2011 | Demarais et al. |
| 2011/0257564 A1 | 10/2011 | Demarais et al. |
| 2011/0257622 A1 | 10/2011 | Salahieh et al. |
| 2012/0010524 A1 | 1/2012 | Fojtik et al. |
| 2012/0053604 A1 | 3/2012 | DiCaprio |
| 2012/0071832 A1 | 3/2012 | Bunch |
| 2012/0101490 A1 | 4/2012 | Smith |
| 2012/0108517 A1 | 5/2012 | Evans et al. |
| 2012/0116438 A1 | 5/2012 | Salahieh et al. |
| 2012/0130269 A1 | 5/2012 | Rea |
| 2012/0130289 A1 | 5/2012 | Demarais et al. |
| 2012/0130345 A1 | 5/2012 | Levin et al. |
| 2012/0143181 A1 | 6/2012 | Demarais et al. |
| 2012/0197198 A1 | 8/2012 | Demarais et al. |
| 2012/0197252 A1 | 8/2012 | Deem et al. |
| 2012/0253186 A1 | 10/2012 | Simpson et al. |
| 2012/0253192 A1 | 10/2012 | Cressman |
| 2012/0271277 A1 | 10/2012 | Fischell et al. |
| 2012/0271301 A1 | 10/2012 | Fischell et al. |
| 2012/0296329 A1 | 11/2012 | Ng |
| 2013/0053792 A1 | 2/2013 | Fischell et al. |

(56) References Cited

U.S. PATENT DOCUMENTS

| | | |
|---|---|---|
| 2013/0053821 A1 | 2/2013 | Fischell et al. |
| 2013/0053822 A1 | 2/2013 | Fischell et al. |
| 2013/0090637 A1 | 4/2013 | Sliwa |
| 2013/0103026 A1 | 4/2013 | Kleshinski et al. |
| 2013/0131743 A1 | 5/2013 | Yamasaki et al. |
| 2013/0138082 A1 | 5/2013 | Salahieh et al. |
| 2013/0144251 A1 | 6/2013 | Sobotka |
| 2013/0178910 A1 | 7/2013 | Azamian et al. |
| 2013/0274614 A1 | 10/2013 | Shimada et al. |
| 2013/0274673 A1 | 10/2013 | Fischell et al. |
| 2013/0274674 A1 | 10/2013 | Fischell et al. |
| 2013/0287698 A1 | 10/2013 | Seward |
| 2014/0024959 A1 | 1/2014 | Sobotka |
| 2014/0046298 A1 | 2/2014 | Fischell et al. |
| 2014/0121641 A1 | 5/2014 | Fischell et al. |
| 2014/0121644 A1 | 5/2014 | Fischell et al. |
| 2014/0236103 A1 | 8/2014 | Fischell et al. |
| 2014/0316351 A1 | 10/2014 | Fischell et al. |
| 2014/0358079 A1 | 12/2014 | Fischell et al. |
| 2014/0378906 A1 | 12/2014 | Fischell et al. |
| 2015/0005719 A1 | 1/2015 | Fischell et al. |
| 2015/0119674 A1 | 4/2015 | Fischell et al. |
| 2015/0119875 A1 | 4/2015 | Fischell et al. |
| 2015/0132409 A1 | 5/2015 | Stein et al. |
| 2015/0202220 A1 | 7/2015 | Stein et al. |
| 2015/0224289 A1 | 8/2015 | Seward |
| 2015/0245863 A1 | 9/2015 | Fischell et al. |
| 2015/0335384 A1 | 11/2015 | Fischell et al. |
| 2015/0343156 A1 | 12/2015 | Fischell et al. |
| 2016/0045257 A1 | 2/2016 | Fischell et al. |
| 2016/0058489 A1 | 3/2016 | Fischell et al. |
| 2016/0120587 A1 | 5/2016 | Fischell et al. |
| 2016/0235464 A1 | 8/2016 | Fischell et al. |
| 2016/0242661 A1 | 8/2016 | Fischell et al. |
| 2016/0279384 A1 | 9/2016 | Zarins et al. |
| 2016/0354137 A1 | 12/2016 | Fischell et al. |
| 2017/0304594 A1 | 10/2017 | Fischell et al. |
| 2017/0326363 A1 | 11/2017 | Deem et al. |
| 2017/0332926 A1 | 11/2017 | Fischell et al. |
| 2018/0071019 A1 | 3/2018 | Fischell et al. |
| 2018/0193596 A1 | 7/2018 | Fischell et al. |
| 2018/0279894 A1 | 10/2018 | Fischell et al. |
| 2019/0008580 A1 | 1/2019 | Fischell et al. |
| 2019/0015002 A1 | 1/2019 | Fischell et al. |

FOREIGN PATENT DOCUMENTS

| | | |
|---|---|---|
| CN | 1927130 | 3/2007 |
| EP | 0834288 | 4/1998 |
| EP | 0876805 | 8/2006 |
| JP | H07509389 | 10/1995 |
| JP | H0889582 | 4/1996 |
| JP | 2001527428 | 12/2001 |
| JP | 2002510229 | 4/2002 |
| JP | 2002542901 | 12/2002 |
| JP | 2004516042 | 6/2004 |
| JP | 2005-40599 | 2/2005 |
| JP | 2008506500 | 3/2008 |
| JP | 09509865 | 3/2009 |
| WO | WO94/04220 | 3/1994 |
| WO | WO95/13752 | 5/1995 |
| WO | WO 2004/030740 | 4/2004 |
| WO | WO 2007/121143 | 10/2007 |
| WO | WO 2009/141727 | 11/2009 |
| WO | WO 2010/124120 | 10/2010 |
| WO | WO 2011/094367 | 8/2011 |
| WO | WO 2012/145300 | 10/2012 |
| WO | WO 2012/145304 | 10/2012 |
| WO | WO 2013/028781 | 2/2013 |
| WO | WO 2013/112844 | 8/2013 |
| WO | WO 2013/159066 | 10/2013 |
| WO | WO 2014/070558 | 5/2014 |
| WO | WO 2015/061614 | 4/2015 |
| WO | WO 2015/168314 | 11/2015 |

OTHER PUBLICATIONS

U.S. Appl. No. 15/947,460, filed Apr. 6, 2018, Fischell, et al.
U.S. Appl. No. 15/947,618, filed Apr. 6, 2018, Fischell, et al.
U.S. Appl. No. 15/947,619, filed Apr. 6, 2018, Fischell, et al.
U.S. Appl. No. 15/947,626, filed Apr. 6, 2018, Fischell, et al.
U.S. Appl. No. 16/039,234, filed Jul. 18, 2018, Fischell, et al.
Angelini et al., Retractable-Needle Catheters: An Updated on Local Drug Delivery in Coronary Interventions, Texas Heart Institute Journal, 2008, p. 419-424.
Bello-Reuss et al., Effects of Acute Unilateral Renal Denervation in the Rat, J. of Clinical Investigation, vol. 56, Jul. 1975, p. 208-217.
Berne, Hemodynamics and Sodium Excretion of Denervated Kidney in Anesthetized and Unanesthetized Dog, Am. J. of Physiology, vol. 171, No. 1, Oct. 1952, p. 148-158.
Chinushi et al., "Blood Pressure and Autonomic Responses to Electrical Stimulation of the Renal Arterial Nerves Before and After Ablation of the Renal Artery", Hypertension, 2013, vol. 61, p. 450-456.
Dave, R.M., "The ClearWay™ RX Local Therapeutic Infusion Catheter", CathLab Digest, May 2010, vol. 18, No. 5, p. 1-6.
Demas et al., Novel method for localized, functional sympathetic nervous system denervation of peripheral tissue using guanethidine (Journal of Neuroscience Methods 112, 2001), p. 21-28.
Dorward et al., "Reflex Responses to Baroreceptor, Chemoreceptor and Nociceptor Inputs in Single Renal Sympathetic Neurons in the Rabbit and the Effects of Anaesthesia on Them", Journal of the Autonomic Nervous System, 1987, vol. 18, p. 39-54.
F Mahoud, C Ukena, RE Schmieder. Ambulatory Blood Pressure Changes After Renal Sympathetic Denervation in Patients With Resistant Hypertension. Jul. 8, 2013 AHA Circulation 2013;128:132-140.
Gado et al., "Intra-articular guanethidine injection for resistant shoulder pain: a preliminary double blind study of a novel approach" Annals of the Rheumatic Disease, 1996, p. 199-201.
Habara et al., "Novel Use of a Local Drug Delivery Catheter for Coronary Perforation", Journal of Invasive Cardiology, Jan. 2011, vol. 23, No. 1, p. 1-8.
Hamza et al., "Substantial Reduction in Single Sympathetic Nerve Firing After Renal Denervation in Patients With Resistant Hypertension", Nov. 19, 2012, p. 856-864.
Hsu et al., "The Use of Intravenous Guanethidine Block in the Management of Reflex Sympathtic Dystrophy Syndrome of the Hand." Second Congress of the Hong Kong Orthopaedic Association, Nov. 1982, p. 93-105.
Hering et al., "Substantial Reduction in Single Sympathetic Nerve Firing After Renal Denervation in Patients With Resistant Hypertension", Nov. 19, 2012 in 15 pages.
Klein et al. "Functional reinnervation and development of supersensitivity to NE after renal denervation in rats" American Physiological Society, 1980, p. 353-358.
Klein et al., Effect of Renal Denervation on Arterial Pressure and Renal Norepinephrine Concentration in Wistar-Kyota and Spontaneously Hypersensitive Rats, Can. J. Physiology and Pharmacology, vol. 58, 1980, p. 1384-1388.
Markovic, B., et al., "Embolization With Absolute Ethanol Injection of Insufficiently Ligated Renal Artery After Open Nephrectomy"; Diagnostic and Interventional Radiology, Mar. 2011; vol. 17, Issue 1, p. 88-91.
"Multi-prong Infusion Needle Case Study", from the web site of peridot™ Precision Manufacturing, http://www.peridotcorp.com/casestudy.aspx, Copyright 2012, in 8 pages.
Nanni et al., Control of Hypertension by Ethanol Renal Ablation (Radiology 148:51-54, Jul. 1983), p. 52-54.
National Institute for Health and Care Excellence. Hypertension in adults: diagnosis and management. Aug. 24, 2011, Nice, CG127.
Owens et al., Percutaneous Peri-Adventitial Guanethidine Delivery Induces Renal Artery Sympathectomy: Preclinical Experience and Implication for Refractory Hypertension (Journal of Vascular Surgery 53:17S), p. 87S, Jun. 2011.
Roytta et al., Taxol-induced neuropathy: short-term effects of local injection (Journal of Neurocytology 13, 1984), p. 685-701.

(56) References Cited

OTHER PUBLICATIONS

S.J .Doletskiy et al. "Vysokochastotnaj Elektrotekhnika", M., 7-10 "Meditsina", 1980, p. 48-50, fig. 18- 19.
Trostel et al., Do renal nerves chronically influence renal function and arterial pressure in spinal rats? (The American Physiological Society 1992), p. 1265-1270.
Verloop et al., Eligibility for percutaneous renal denervation: the importance of a systematic screening, Journal of Hypertension, 2013, p. 1-7.
Vink et al. Limited destruction of renal nerves after catheter-based renal denervation: results of a human case study, Nephrol Dial Transplant, 2014, p. 1-3.
Ya Ashram, NH Abdel Wahab, IH Diab, Non-dipping pattern of nocturnal blood pressure in obstructive sleep apnea syndrom: Possible role of oxidative stress and endothelin-1 precursor. Feb. 14, 2013, Alexandria Journal of Medicine, 49, 153-161.
Zafonte et al., "Phenol and Alcohol Blocks for the Treatment of Spasticity", Physical medicine and rehabilitation clinics of North America, Nov. 2001, p. 817-832.
International Search Report and Written Opinion in PCT/US14/062043 dated Mar. 27, 2015 in 16 pages.
International Search Report and Written Opinion in PCT/US16/65017 dated Aug. 14, 2017 in 9 pages.
Extended Search Report in EP 14855452.0 dated May 22, 2017 in 7 pages.
Office Action for Chinese Patent Application 201480068510.0 dated Dec. 25, 2017 in 20 pages.
Office Action for Chinese Patent Application 201480068510.0 dated Nov. 16, 2018 in 18 pages.

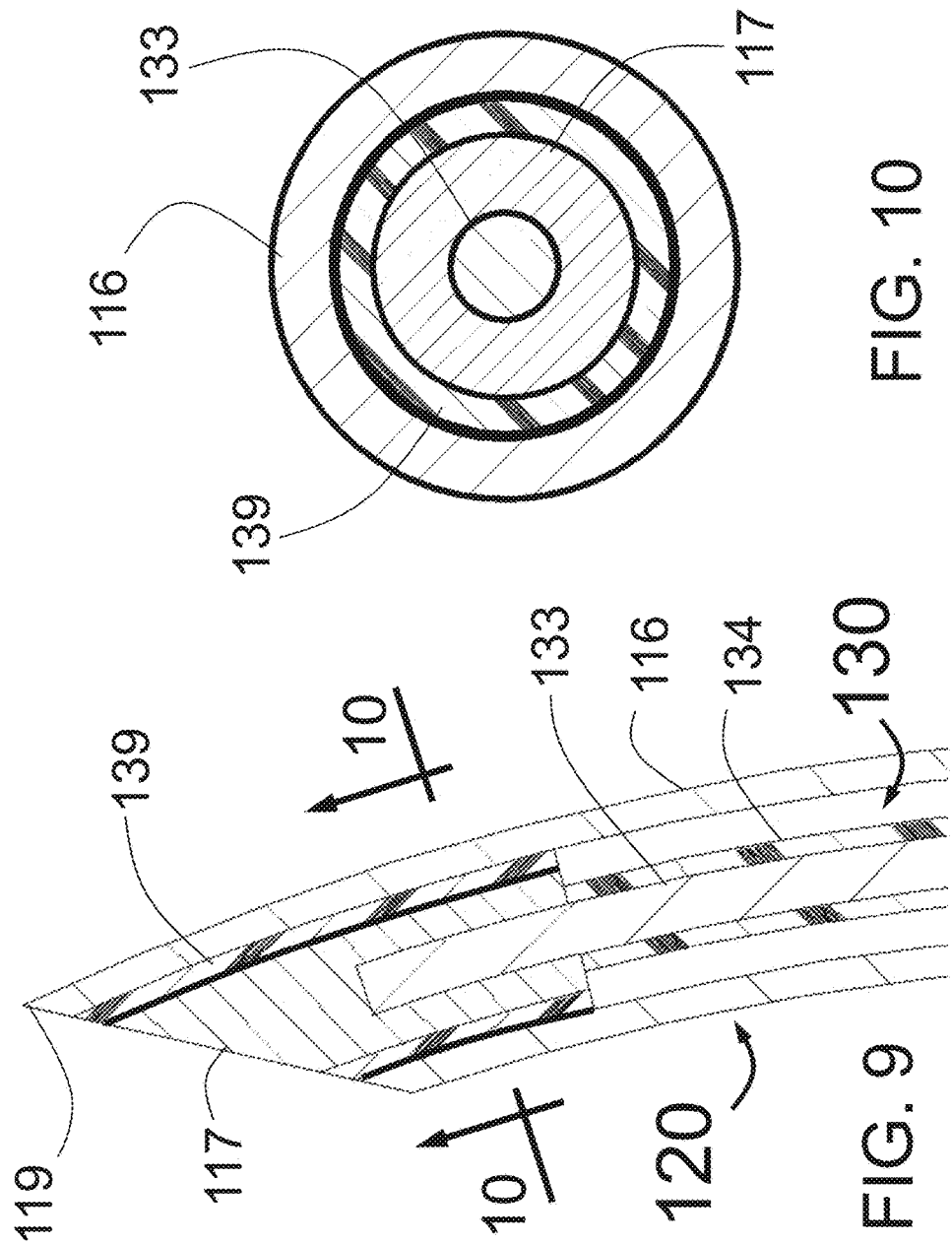

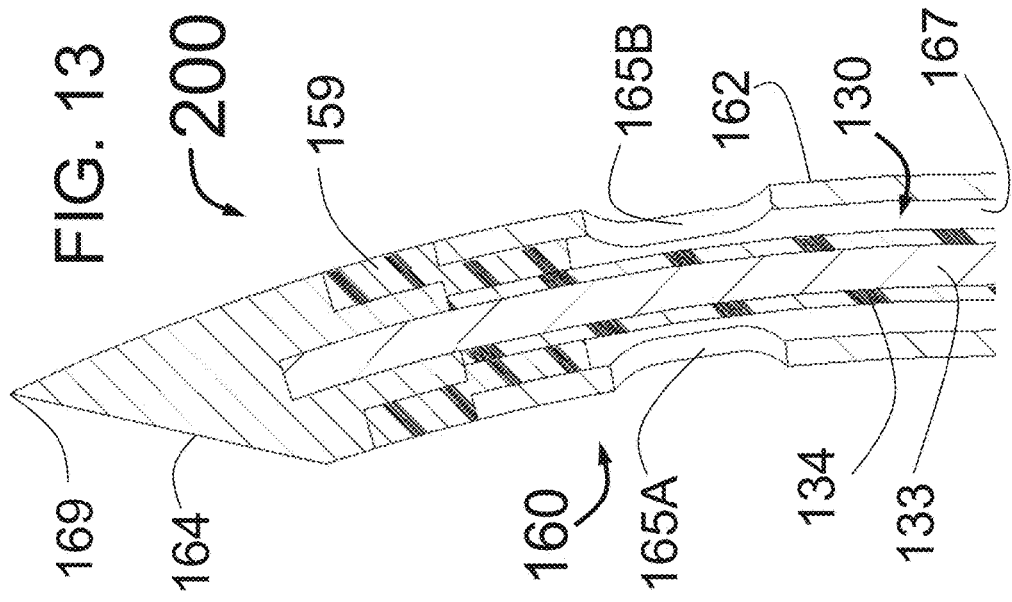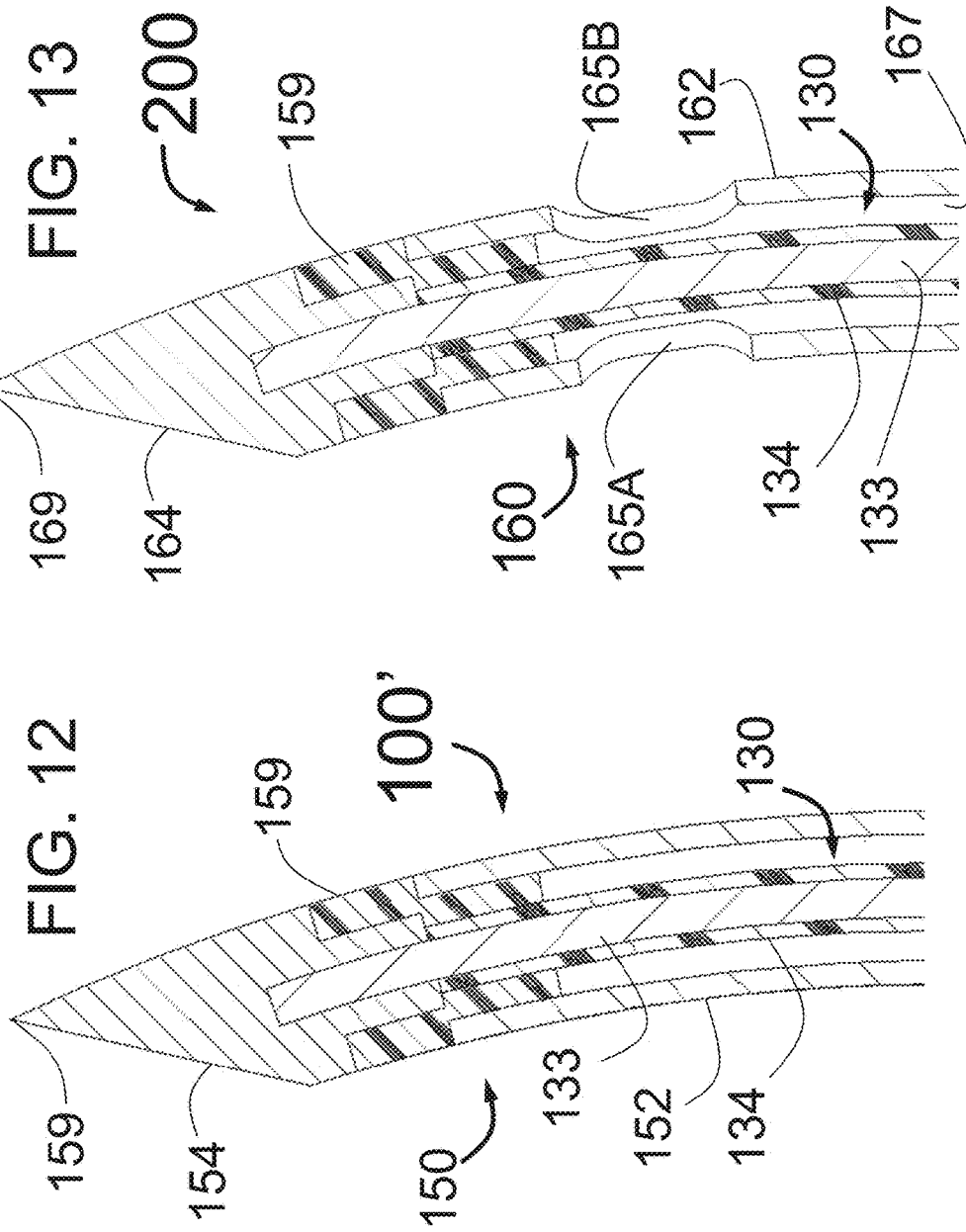

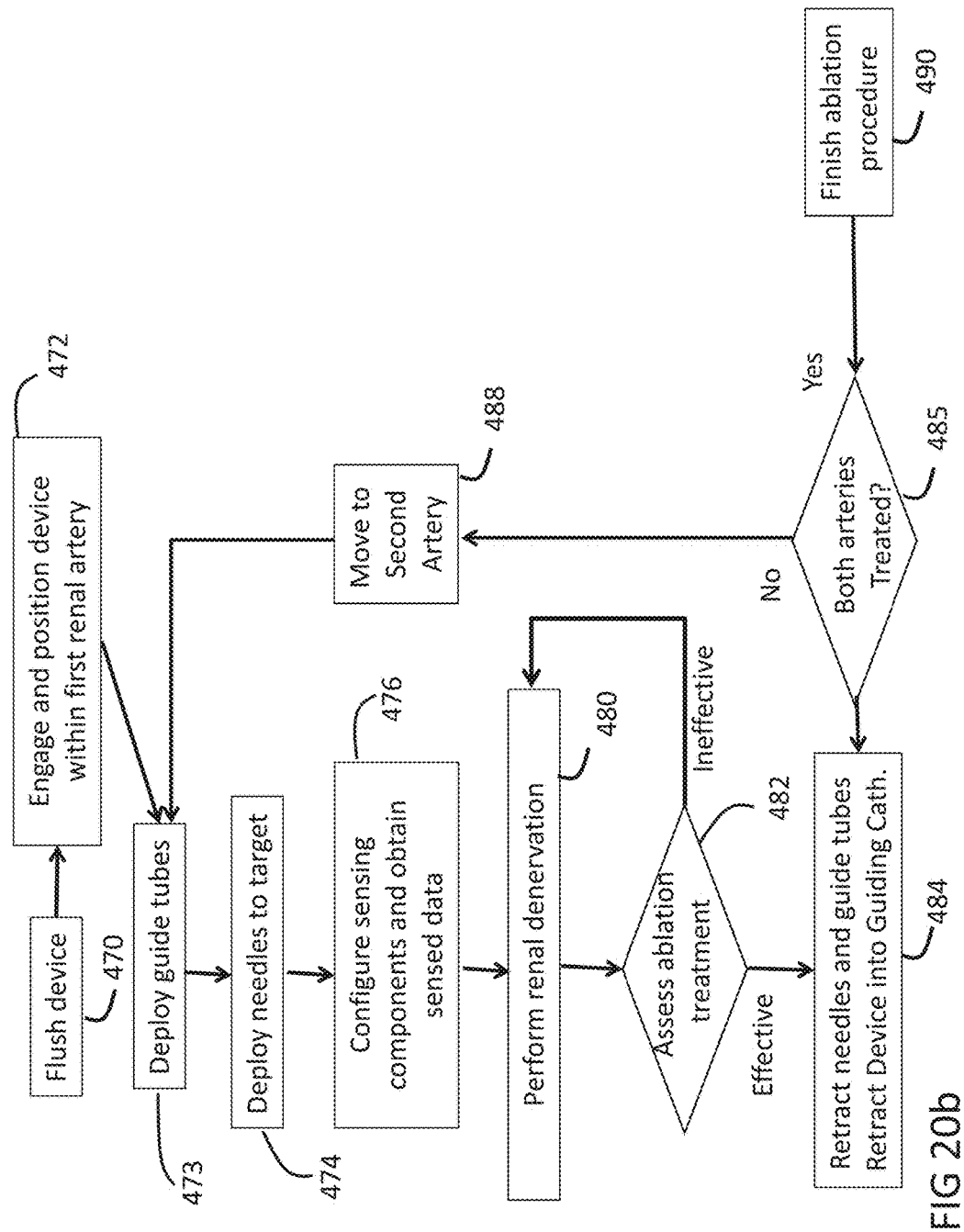

APPARATUS FOR EFFECTIVE ABLATION AND NERVE SENSING ASSOCIATED WITH DENERVATION

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

CROSS-REFERENCE TO RELATED APPLICATIONS

This application is a continuation application of U.S. patent application Ser. No. 15/663,409 filed on Jul. 28, 2017, which in turn is continuation application of U.S. patent application Ser. No. 14/963,179 filed on Dec. 8, 2015, which in turn is a continuation-in-part of U.S. patent application Ser. No. 14/063,907 entitled "Intravascular Catheter with Peri-vascular Nerve Activity Sensors," filed on Oct. 25, 2013, the disclosures of each of the foregoing applications of which are incorporated in their entireties herein by reference.

BACKGROUND

Field of the Invention

This invention relates in some aspects to the field of devices that monitor, stimulate, and/or ablate tissue and nerve fibers primarily in the adventitial and/or periadvential area surrounding a blood vessel.

Description of the Related Art

It has been recognized that activity of the sympathetic nerves to the kidneys contributes to essential hypertension, which is the most common form of hypertension. Sympathetic stimulation of the kidneys may contribute to hypertension by several mechanisms, including the stimulation of the release of renin (which results in production of angiotensin II, a potent vasoconstrictor), increased renal reabsorption of sodium, at least in part related to increased release of aldosterone (which increases blood volume and therefore blood pressure), and reduction of renal blood flow, which also results in angiotensin II production.

Since the 1930s it has been known that injury or ablation of the sympathetic nerves in or near the outer layers of the renal arteries can dramatically reduce high blood pressure. As far back as 1952, alcohol has been used for tissue ablation in animal experiments. Specifically Robert M. Berne in "Hemodynamics and Sodium Excretion of Denervated Kidney in Anesthetized and Unanesthetized Dog" Am J Physiol, October 1952 171:(1) 148-158, describes applying alcohol on the outside of a dog's renal artery to produce denervation.

Ablation of renal sympathetic nerves to treat hypertension has been shown to be a successful strategy (e.g., Renal sympathetic denervation in patients with treatment-resistant hypertension (The Symplicity HTN-2 Trial): a randomized controlled trial. Lancet 2010, 376:1903-1909).

However, in order for the procedure to be successful, renal nerves need to be sufficiently ablated such that their activity is significantly diminished. This issue was likely a contributing factor in Simplicity HTN-3 Trial (e.g., Catheter-based renal denervation for resistant hypertension: rationale and design of the SYMPLICITY HTN-3 Trial. Clin Cardiol. 2012; 35:528-535). In this study, incomplete ablation may have served as a key determinant in the negative study outcome. A significant drawback of ablation procedures is the inability for the physician performing the procedure to ascertain during the procedure itself that the ablation has been successfully accomplished. The reason for this is that the nerves cannot be visualized during the procedure; therefore, the procedure is be performed in a "blind" fashion. The ablation procedure is invasive, requiring catheterization of the femoral artery, advancement of a catheter into the renal artery, administration of iodinated contrast agents, and radiation exposure. Furthermore, procedural success with currently available devices is far from universal. In spite of success in some patients as found in the Symplicity-HTN-2 Trial, it is noteworthy that 16% of patients failed to achieve even a 10 mmHg reduction in systolic blood pressure and 61% did not achieve a goal systolic blood pressure of <140 mmHg.

The procedure is be performed in a catheterization laboratory or operative-type suite. The benefit-risk, cost-benefit, and incremental cost effectiveness ratio, of this invasive procedure would all be enhanced if measures related to procedural success could be assessed during the procedure. Assessing the success, or sensing relevant data to guide the ablation procedure, during the surgery would allow the physician to perform additional ablation interventions and/or to adjust the technique as needed. This real-time assessment would be expected to improve efficacy and to reduce the need to bring the patient back for a second procedure at additional cost and risks to the patient.

The desired effect of renal sympathetic nerve ablation procedure is a lowering of blood pressure, with consequent reduction in the need for chronic antihypertensive drug treatment. Since the blood pressure lowering effect of the treatment often does not occur immediately, the blood pressure measured in the catheterization laboratory cannot act as a measure to guide to the technical success of the procedure. What is clearly needed are systems and methods for assessing denervation procedural success, for example, by stimulating the nerve fibers to assess whether the stimulation modulates a measurable quantity such as blood pressure or cardiac activity, or by directly recording nerve activity from the from the target volume of tissue, or both (e.g. recording evoked activity that is time locked to stimulation).

There are currently two basic methods to ablate renal sympathetic nerves: a) energy-based neural damage resulting from radiofrequency or ultrasonic energy delivery and b) chemical neurolysis. Both methods require percutaneous insertion of a catheter into the renal arteries. Radiofrequency-based methods transmit radiofrequency energy through the renal artery wall to ablate the renal nerves surrounding the blood vessel. Chemical neurolysis uses small gauge needles that pass through the renal artery wall to inject a neurolytic agent directly into the adventitial and/or periadvential area surrounding the blood vessel, which is where the renal sympathetic nerves entering and leaving the kidney (i.e., afferent and efferent nerves) are located.

Recent technology for renal denervation includes energy delivery devices using radiofrequency or ultrasound energy, such as Simplicity™ (Medtronic), Vessix™. (Boston Scientific) EnligHTN™ (St. Jude Medical) and One Shot system from Covidien, all of which are RF ablation catheters. There are potential risks using the current technologies for RF ablation to create sympathetic nerve denervation from inside the renal artery. The short-term complications and the long-term sequalae of applying RF energy from the inner lining (intima) of the renal artery to the outer wall of the artery are not well defined. This type of energy applied within the renal artery, and with transmural renal artery injury, may lead to late stenosis, thrombosis, renal artery spasm, embolization of debris into the renal parenchyma, or other problems related to the thermal injury of the renal artery. There may also be uneven or incomplete sympathetic nerve ablation, particularly if there are anatomic anomalies, individual variation in characteristics such as wall depth or distance of nerves from the inner wall, or atherosclerotic or fibrotic disease in the intima of the renal artery, the result being that there is non-homogeneous or otherwise ineffective delivery of RF energy. This could lead to treatment failures, or the need for additional and potentially dangerous levels of RF energy to ablate the nerves that run along the adventitial plane of the renal artery. Similar safety and efficacy issues may also be a concern with the use of ultrasound or other type of energy used for ablation when this is provided from within the vessel wall.

The Simplicity™ system for RF delivery, like other energy based systems, applies energy to the intimal surface of the artery in a spiral pattern because intraluminal circumferential ablation would result in a higher risk for permanent arterial damage leading to renal artery stenosis or perforation. The "burning" of the interior wall of the renal artery using RF ablation can be extremely painful during the procedure. The long duration of the RF ablation renal denervation procedure requires sedation and, at times, high doses of morphine or other opiates, and anesthesia, close to the levels used for general anesthesia, to control the severe pain associated with repeated burning of the vessel wall and its associated pain fibers. This is especially difficult to affect with any energy based system operating from inside the renal artery because the C-fibers, which are the pain nerves, are located within or close to the media layer of the artery. Thus, there are numerous and substantial limitations of the current approach using RF-based renal sympathetic denervation. Similar limitations apply to ultrasound or other energy delivery techniques which are delivered from within the renal artery.

The Bullfrog® micro infusion catheter described by Seward et al in U.S. Pat. Nos. 6,547,803 and 7,666,163, which uses an inflatable elastic balloon to expand a single needle against the wall of a blood vessel, could be used for the injection of a chemical ablative solution such as guanethidine or alcohol but it would require multiple applications. For example, in one embodiment, the needle would be rotated within the arterial wall and then re-deployed in a new target area. Those Seward et al., patents do not describe or anticipate the circumferential delivery of an ablative substance to provide ablation around the entire circumference of the vessel. The greatest number of needles shown by Seward is two, and the two needle version of the Bullfrog® would be hard, if not impossible, to miniaturize sufficiently to enable the distal end to fit through a small guiding catheter to be used in a renal artery, particularly if needles of adequate length to penetrate to the periadventitia were used: this shortcoming is why the Bullfrog® is usually illustrated with one needle. Accordingly, the incorporation of three needles would likely be impossible to realize using the technology disclosed in that prior art. If only one needle is used, controlled and accurate rotation of any device at the end of a catheter is difficult at best and could be risky, inaccurate, and therapeutically ineffective if the subsequent injections are not evenly spaced. This device also does not allow for a precise, controlled and adjustable penetration depth (i.e. relative to the wall surface) of delivery of a neuroablative agent. The physical constraints regarding the length that can be used, thus limits the ability to inject agents to an adequate depth outside of the arterial wall, particularly in diseased renal arteries with thickened intima. All of these limitations could lead to incomplete denervation and treatment failure. Another limitation of the Bullfrog® is that inflation of a balloon within the renal artery can induce transient renal ischemia during the operation and possibly late vessel stenosis due to balloon injury of the intima and media of the artery, as well as causing endothelial cell denudation.

Jacobson and Davis in U.S. Pat. No. 6,302,870 disclose a catheter for medication injection into the interior wall of a blood vessel. While Jacobson includes the concept of multiple needles expanding outward, each with a hilt to limit penetration of the needle into the wall of the vessel, his design depends on rotation of the tube having the needle at its distal end to allow it to get into an outwardly curving shape. The hilt design shown of a small disk attached a short distance proximal to the needle distal end has a fixed diameter which will increase the total diameter of the device by at least twice the diameter of the hilt so that if the hilt is large enough in diameter to stop penetration of the needle, it will significantly add to the diameter of the device. Using a hilt that has a greater diameter than the tube, suffers the disadvantage that it increases the device profile, and also prevents the needle from being completely retracted back inside the tubular shaft from which it emerges This design requires keeping the needles exposed and potentially allowing accidental needlestick injuries to occur, during either catheter removal after the ablation procedure is completed, during any rotation which is desired during the procedure, or when moving from one target location to the next. For either the renal denervation or atrial fibrillation application, the length of the needed catheter would make control of such rotation difficult. Jacobson appears to intend the drug to be injected into the vessel wall rather than injecting exterior to the vessel wall (at the targets nerve sites themselves) since the hilts, which limit penetration, are a relatively short fixed distance from the distal end of the needles. Longer penetration depths that are needed to provide the advantage of extending beyond the adventitia to the location of the sympathetic nerves outside of the renal artery would greatly increase the diameter of the Jacobson catheter thereby making insertion of the catheter tip problematic and needlestick injuries even more likely. There is also no mechanism that would provide for the adjustment of penetration depth which may be important if the clinician wishes to selectively target a specific layer in a vessel or penetrate all the way through to the volume of tissue outside of the adventitia in vessels that may have different wall thicknesses. Many of the limitations of Jacobson may be due to the fact that Jacobson does not envision use of the injection catheter for denervation. It is also of note that FIG. 3 of the Jacobson patent shows a sheath over expandable needles and does not disclose a guide wire. Further, the sheath has an open distal end. Both of these design limitations make advancement through the vascular system more difficult. Lastly, because of the hilts used by Jacobson, if the needles were withdrawn completely inside of the sheath they could get stuck inside the sheath and be difficult to push out during the intended deployment at the target area. The above listed limitations and complexity of the Jacobson system might increase the risk of surgical complications and inadequate, or incomplete, renal denervation.

McGuckin in U.S. Pat. No. 7,087,040 discloses a tumor tissue ablation catheter having three expandable tines for injection of fluid that exit a single needle. The tines expand outwardly to penetrate the tissue. The McGuckin device has an open distal end that does not provide protection from inadvertent needle sticks from the sharpened tines. In addition, the McGuckin device depends on the shaped tines to be of sufficient strength so that they can expand outwardly and penetrate the tissue. To achieve such strength, the tines would have to be so large in diameter that severe extravascular bleeding would likely often occur when the tines would be retracted back following fluid injection for a renal denervation application. Further, there is no workable penetration limiting mechanism that will reliably set the depth of penetration of the distal opening from the tines with respect to the interior wall of the vessel, nor is there disclosed a preset adjustment for such depth. For the application of treating liver tumors, the continually adjustable depth of tine penetration may make sense since multiple injections at several depths might be needed. However, for renal denervation, the ability to accurately adjust the depth or have choice of penetration depth when choosing the device to be used can be important so as to not infuse the ablative fluid too shallow and injure the media of the renal artery or too deep and thus miss the nerves that are in the adventitial and peri-adventitial layers of the renal artery.

Fischell et al in U.S. Pat. Nos. 8,740,849, 9,056,185, 9,179,962 and application Ser. Nos. 13/216,495, 13/294,439 and 13/342,521 describe apparatus and methods of using expandable needles to deliver ablative fluid into or deep to the wall of a target vessel. Each of these applications is hereby incorporated by reference in its entirety. There are two main types of embodiments of the above patents and patent applications, those where the needles alone expand outwardly without support from any other structure and those with support structures such as guide tubes that act as guiding elements to support the needles as they are advanced into and/or through the wall of a target vessel. The limitation of the needle alone designs are that if small enough diameter needles are used to avoid unwanted surgical results such as blood loss following penetration through the vessel wall, then the needles may be too flimsy to reliably and uniformly expand to their desired positions. The use of a cord or wire to connect the needles together in as shown in U.S. Pat. No. 9,056,185 helps some in the area. The use of guide tubes as described in the Fischell U.S. Pat. No. 8,740,849 and patent application Ser. Nos. 13/294,439 and 13/342,521 greatly improves this support, but the unsupported guide tubes themselves depend on their own shape to ensure that they expand uniformly and properly center the distal portion of the catheter. Without predictable catheter centering and guide tube expansion it may be challenging to achieve accurate and reproducible needle penetration to a targeted depth. More recently in U.S. Pat. No. 8,740,849, Fischell et al describe self-expanding and manually expandable ablation devices that have additional structures to support the needle guiding elements/guide tubes. Of these the preferred embodiment is the manually expandable design that will be the basis, at least for illustration purposes and without intention of limiting the disclosed invention, for the various embodiments of the present invention disclosed herein. The 8,740,849 designs for a Perivascular Tissue Ablation Catheter (PTAC) will be referenced throughout this disclosure.

While the prior art has the potential to produce ablation of the sympathetic nerves surrounding the renal arteries and thus produce desired therapeutic effects such as reducing the patient's blood pressure, none of the prior art includes sensors (e.g. extravascular sensors) or additional systems to monitor the activity of the sympathetic nerves being ablated. Such measurement would be advantageous as it could provide feedback related to the effectiveness of the ablation procedure and indicate such as indicating if an additional ablation administration may be needed. For example, additional energy delivery or additional ablative fluid delivery or other type of ablation treatment could be administered if sensed data obtained from sensors outside the vessel wall indicate the nerves were not ablated sufficiently such may occur if the nerves are still conducting (electrical) activity.

It is technically feasible to measure renal sympathetic activity directly or indirectly in vivo using several methods. Such measurements have been accomplished, for example in unrestrained conscious mice [Hamza and Hall, Hypertension 2012], dogs [Chimushi, et al. Hypertension 2013], rats [Stocker and Muntzel, Am J Physiol Heart Circ Physiol. 2013] and rabbits [Doward, et al. J Autonomic Nervous System 1987].

In the study by Hamza and Hal, an electrode was surgically placed directly on the renal nerves and left in place while recordings were made over up to 5 days. The recordings of renal sympathetic nerve activity were confirmed by observations of appropriate responses to conditions of rest and activity, pharmacologic manipulation of blood pressure with sodium nitroprusside and phenylephrine, and by neural ganglionic blockade. Doward, et al also used surgical placement of an electrode to directly measure renal sympathetic nerve activity. The recordings of renal sympathetic nerve activity were confirmed by observations of appropriate responses to baroreceptor stimulation, angiotensin, central and peripheral chemoreceptors. In the study by Chimushi et al., renal sympathetic nerves were stimulated from within the renal artery and evidence of activity was indirectly evaluated based on blood pressure response to neural stimulation.

Throughout this disclosure the term perivascular space refers to the volume of tissue radially outside of (or deep to) the media of a vessel of the human body such as an artery.

SUMMARY

The present application discloses, in some embodiments, a Nerve Sensing Catheter (NSC) that senses perivascular renal sympathetic nerve activity (as an example although other types of extra-vascular nerve activity, including non-sympathetic nerves, may also be measured) and can be used complementary to a non-sensing renal denervation device whether it is a chemical device such as the PTAC of Fischell (e.g., U.S. Pat. Nos. 8,740,849 and 9,056,185) or an energy delivery device such as SIMPLICITY®, or even when using external sources of ablation such as surgical intervention, or externally delivered energy such as focused ultrasound (such as the Surround Sound™ system of Kona Medical), etc.

Also disclosed is a perivascular Nerve Ablation and Sensing Catheter (PNASC). In one embodiment the PNASC is capable of delivering an ablative fluid to produce circumferential damage in the tissue that is located within the vessel wall, (e.g. the media of an artery) in the outer layer of the vessel (e.g. in the adventitia of an artery) or beyond the outer layer of a vessel of a human body. The PNASC also includes sensors for sensing the activity of nerves, such as the sympathetic nerves that lie outside of the external elastic lamina of the renal artery. The integrated PNASC has the advantage of saving time at the cost of adding complexity to a device that was only designed to provide ablation. The NSC requires a separate renal denervation device to be used to provide ablation, but has a large potential market when used in combination with other, potentially less effective and less predictable renal denervation devices, such as those that ablate nerves using RF energy from intravascular sites. PNASC embodiments also are disclosed that use, RF or ultrasonic energy to provide for perivascular nerve ablation, such as renal nerve ablation.

The nerve ablation procedure using perivascular injection of alcohol by the prior art catheters disclosed by Fischell (e.g., the PTAC) or the PNASC disclosed herein, can be accomplished in a relatively short time as compared with RF ablation catheters, and in some embodiments also has the advantage of using only a single disposable catheter, with no additional, external, capital equipment. It will also, because of reduced pain levels and shorter procedural time, provide the advantages such as permitting:

the use of short acting sedating agents like Versed, delivery of local anesthetic into the adventitial space before ablation and the potential elimination/reduction of the need for large doses of narcotics to counter patient discomfort and pain that are typically experienced during RF energy based ablation procedures.

Part of some embodiments of the present invention method for use of the PNASC envisions that the pain associated with a chemical renal denervation procedure can be either largely reduced or completely eliminated by using ethanol as the ablative agent and also injecting the ethanol slowly over a period no shorter than at least 10 seconds and ideally longer than 30 seconds, which serves as a local analgesic at the site of the renal nerves prior to its effect as an ablative agent. This provides the advantage of decreasing the use of general anesthesia, and its associated risks and disadvantages, by providing for analgesia in the region of ablation.

While the primary focus of use of PNASC is in the treatment of hypertension and congestive heart failure by renal denervation, the PNASC has the ability to sense nerve activity such as sympathetic nerve activity, and could also be used in conjunction with other renal denervation devices to enhance the effectiveness of the renal denervation or to provide additional denervation if the other device is not appropriately effective.

In preferred embodiments, much of the structure of the NSC and PNASC may be similar to the manually expandable PTAC designs shown in FIGS. 2 through 11 of Fischell et al U.S. Pat. No. 8,740,849 incorporated herein by reference. Specifically, the NSC and PNASC would use the similar proximal control structures as well as the same guide tubes and radial and lateral support structures.

Various versions of the NSC and PNASC will be included herein. In one embodiment of the NSC the injector tubes with distal injection needles of the PTAC of U.S. Pat. No. 8,740,849 are replaced by a solid sharpened wire that is electrically insulated except for its tip that forms an electrode. The proximal end of each wire connects through conducting means to electronic equipment (e.g., connected to wires at the proximal end of the catheter) used to monitor nerve activity sensed by the electrodes and/or provide energy to the electrodes to ablate nerve tissue.

For one embodiment of the PNASC, the PTAC structure shown in FIGS. 2-10 of U.S. Pat. No. 8,740,849 would be modified to have the radiopaque wire inside the injector needles replaced by an electrode connected to a proximal insulated wire positioned within the distal end of the injection needle. Ideally, the electrode would be of gold or platinum or another radiopaque metal to provide radiopacity. At least two configurations of this PNASC embodiment will be disclosed: one where the electrode lies completely within the lumen of the injection needle and a second embodiment where the electrode extends distally beyond the lumen of the injector tube and forms at least part of the sharpened needle. It is also envisioned that with a separate control mechanism, these sensing electrodes could be advanced through the distal end of the injection needles, further into the perivascular space. It can also be preferred to coat the inside of the distal tip of the PNASC injection needles to prevent the needle tip from shorting to the inside of the metallic needle.

In this example embodiment each of the proximal insulated wires then run through the injector tube lumen into the lumen of the inner tube and finally exit out of the catheter near the proximal end of the PNASC. There, the wires can be attached directly or through a connector to an electronics module for any or all of the following:

providing energy for nerve ablation, for sensing/measuring nerve activity directly or in response to electrical stimulation and identifying changes that indicate when successful or unsuccessful nerve ablation has occurred; and, for providing electrical stimulation energy at a lower voltage or current than is used to provide nerve ablation.

The proximal exit for the wires may be though the side of the catheter or outward through the center of the injection port lumen where a Tuohy-Borst fitting would seal around the wires with the side port in the Tuohy-Borst used for infusion of the ablative fluid.

Sensing of the nerve activity may be done between pairs of electrodes located near or at the distal ends of the needles (PNASC) or wires (NSC) or between an active sensor located near or at the distal end of a needle/wire and a reference electrode.

The reference electrode could be any electrical reference used to reference voltage or current measurements from the distal electrodes embodiments including:

a reference electrode located on the body of the PNASC/NSC, including a ring located on the outside of the PNASC/NSC, a portion of the distal nose of the PNASC/NSC, or an integrated guide wire;

a separate guide wire; or, an electrode placed on the body such as at a location over the location of the renal artery.

The preferred embodiment would measure activity between pairs of distal electrodes or would use the skin electrode (e.g., a standard ECG electrode) as this will allow a smaller diameter configuration of the internal lumen of the catheter.

Embodiments of the PNASC can have injection ports such as side holes in the sensor/injector tube just proximal to the distal electrode or longitudinal holes through the electrode. These holes allow ablative fluid injected from a proximal injection port in the handle of the PNASC to effuse from the distal end of each needle In its embodiments, the PNASC, similar to the PTAC of U.S. Pat. No. 8,740,849 is a percutaneously introduced catheter with two or more injection needles configured for the delivery of ablative fluid. The needles expand outwardly from the catheter and penetrate into or fully through the wall of the renal artery and into the perivascular space where the sympathetic nerves are located.

Another embodiment of the PNASC could have one or more expandable structures separate from the needles for fluid delivery. These structures could be configured to deliver a sharpened wire forming a distal electrode through the arterial wall into the tissue beyond. The control of the expansion of these sharpened wires, which can provide energy based ablation or nerve activity sensing, can occur either by the same or separate mechanisms that expand and support the injection needles. For example, four guide tubes similar to those in the PTAC of U.S. Pat. No. 8,740,849 could expand outwardly from the shaft of the PNASC catheter. Four sharpened structures would then be advanced through the guide tubes through the renal artery wall and/or into the periadventitial space. Two of the four structures could be injection needles for delivery of ablative fluid and two could be sharpened wires for providing energy based ablation and/or nerve activity sensing the effectiveness of the ablation. Preferably, in one embodiment, the sensors are circumferentially offset from the injection needles. In one two-needle embodiment, the offset is about 90 degrees, and in a three-needle implementation, the offset is about 60 degrees. This type of "offset" configuration could be well suited for assessing ablation because the sensors are maximally separated from the injection needles that provide the therapy and so they are located where the effect of the injection would be least evident. In other words, if the nerves are appropriately damaged as reflected by sensed data that is sensed by sensors located at the points furthest from the point of fluid injection then the nerves everywhere else around the ring of ablation should be adequately ablated. Configurations with more or less than 4 penetrating structures can also be envisioned. Configurations with sensing electrodes offset longitudinally from the injection needles are also envisioned. Embodiments where the 4 needles serve both as sensor and ablation elements (at different times) are also envisioned, and further the sensing or ablation can utilize bipolar montages where the anode and cathode are located on the same conduit tip, or monopolar montages where the energy travels between needles or where the return electrode is located elsewhere within/on the patient. Embodiments where combinations of needle electrodes are activated for sensing and/or ablation in sequential order is also envisioned. Further, embodiments in which perivascular RF ablation is preceded or followed by injection of an ablative or analgesic agent will be disclosed—it may be an advantage to utilize RF ablation followed by chemical ablation since the two modalities of ablation may cover different regions of the target nerve pathways.

A PNASC integrated ablation and sensing system may also provide large advantages over other current technologies for applications other than renal denervation as the PNASC provides a highly efficient, and reproducible perivascular circumferential ablation of the muscle fibers and conductive tissue in the wall of the pulmonary veins near or at their ostium into the left atrium of the heart, or in the pulmonary arteries in the case of nerve ablation to treat pulmonary arterial hypertension. Such ablation could interrupt atrial fibrillation (AF) and other cardiac arrhythmias. For the AF application, nerve and/or cardiac myocyte electrical activity measurement could be an effective technique to provide immediate assessment of the success of an AF ablation procedure. Other potential applications of this approach, such as pulmonary artery nerve ablation, or others, may also become evident from the various teachings of this patent specification.

Like the PTAC embodiments of U.S. Pat. No. 8,740,849, the NSC/PNASC of the present application can incorporate a small diameter catheter, which includes multiple expandable injector tubes having sharpened injection needles at or near their distal ends that are advanced through guide tubes designed to support and guide the needles into and/or through the inner layers of the target vessel. While this application concentrates on manually expandable versions of the NSC and PNASC, it is envisioned that similar electrodes could be used with structures similar to the self-expandable embodiments shown in U.S. Pat. No. 8,740, 849.

Some embodiments of the PNASC can also include any one, combinations, or all of the primary features of the self-expandable and balloon expandable embodiments of the Fischell et al U.S. Pat. Nos. 8,740,849, 9,056,185, 9,179,962 and application Ser. Nos. 13/216,495, 13/294,439 and 13/342,521 including but not limited to:

Needle guiding elements/guide tubes to support the expandable injection needles.
Mechanical support structures to support the needle guiding elements,
A catheter body having less than 0.5 ml internal volume or dead space,
Radiopaque markers on the catheter, guide tubes and needles,
Penetration limiting mechanisms,
Depth of penetration adjustment mechanisms,
Proximal handle for control of catheter activation including an injection port,
Matched radii of curvature between the injector tubes and guide tubes,
Methods including injection of an anesthetic agent before the ablation.

The NSC/PNASC devices would preferably have very small gauge needles (smaller than 25 gauge) to prevent unwanted surgical complications such as extravascular blood loss following penetration and removal through the arterial wall. Also the PNASC, which includes a distal opening in one or more needles to provide egress for the ablative fluid, would have a preferred embodiment with the distal needle being non-coring (cutting). With a cutting needle the injection egress/distal opening ports could be small injection holes (pores) cut into the sides of the injector tubes or distal needle, proximal to the cutting needle tip. A Huber type needle is an example of such a non-coring needle. The PNASC would also preferably have at least 2 injector tubes with distal needles, but 3 to 8 tubes with distal needles may be more appropriate for some applications. For example, the number and spacing of needles may be set depending on the diameter of the vessel to be treated and the ability of the injected ablative fluid to spread within the perivascular space. For example, in a 5-7 mm diameter renal artery, 3 needles should typically be utilized if ethanol is the ablative fluid.

A preferred embodiment of the PNASC would use ethanol as the ablative fluid because this fluid is agrophobic, hygroscopic, lipophilic, and spreads quickly in the perivascular space. Therefore, only 3 needles are typically needed to create approximately circumferential delivery of this ablative agent for a vessel of the size of a human renal artery. This allows the use of a smaller diameter and less expensive device than would be possible with 4 or more needles. It is also envisioned that use of ethanol or another alcohol plus another neurotoxic agent could also enhance the spread of the ablative agent in the perivascular space.

While this disclosure will show both NSC and PNASC embodiments which include a fixed distal guide wire, it is envisioned that a separate guide wire could be used with the catheter designed to be either an over-the-wire configuration where the guide wire lumen runs the entire length of the catheter or a rapid exchange configuration where the guide wire exits the catheter body at a proximal guide wire port positioned at least 10 cm proximal to the distal end of the catheter and runs outside of the catheter shaft for its proximal section. It is also envisioned that one could use a soft and tapered distal tip, even without a distal guide wire, for some applications.

A fixed wire embodiment, or an embodiment with the soft tapered distal tip (without a guidewire), are preferred embodiments, as they would have the smallest distal diameter. Just proximal to the fixed wire is a tapered distal portion of the SNAC/PNASC that eliminates any sharp change in diameter that could cause the catheter to snag during advancement into the vasculature of a human.

It is also envisioned that the wires leading to two or more of the distal needle/electrodes could be attached at the proximal end of the PNASC to an electrical or RF source to deliver electric current or RF energy to perform tissue and/or nerve ablation. This could provide an ideal configuration for RF energy based renal denervation since the electrodes deliver the energy outside of the medial layer of the renal artery, and the normal intimal and medial wall structures would be cooled by blood flow. This configuration should dramatically reduce the damage to the artery, and associated clinical complications, as compared with intraluminal RF ablation. Also important in some cases is that the sympathetic nerves to be ablated are quite deep beyond the outside of the media of the artery while the pain nerves are within or close to the media. Therefore an energy based denervation from electrodes deep to the outside of the media may be much less painful than energy based ablation provided at sites inside of the renal artery. The electrical equipment may also include nerve activity sensing electronics.

It may be advantageous that the same electrodes used in a first mode to ablate nerves or other tissue, are also used in a second mode to evaluate the electrical characteristics at the treatment site. For example, one could measure nerve activity to obtain baseline data, provide ablation treatment to the nerves with energy and subsequently confirm the efficacy of the ablation by one or more post-ablation nerve activity measurements. These measurements could then compare the difference between the pre-procedure and post-procedure sensed data to at least one defined therapy efficacy criterion. If ablation was not sufficient since it did not meet the efficacy criterion then a secondary ablation treatment followed by a secondary post-ablation nerve activity measurement would be done to again assess whether the nerves are sufficiently ablated to meet at least one defined therapy efficacy criterion. This can obviously be continued until the one or more therapy criteria are met. Further, while accomplishing more than one ablation treatment the catheter can be moved distally or proximally along the vessel, or rotated, so that the ablation treatment is applied to a new region. This may be especially important in some embodiments when using electrical rather than chemical ablation since this type of ablation may be more localized in its effects.

It is also envisioned that the PNASC device could be operated according to an ablation protocol to provide one ablation substance. Alternatively, more than one neuroablative substances can be injected sequentially or simultaneously according to the ablation protocol. The ablation protocol can also define a sequence of injections configured to ablate the target nerves, in order to optimize permanent sympathetic nerve disruption in a segment of the renal artery (neurotmesis). The anticipated neurotoxic agents that could be utilized to provide ablation include but are not limited to ethanol, phenol, glycerol, local anesthetics in relatively high concentration (e.g., lidocaine, or other agents such as bupivacaine, tetracaine, benzocaine, etc.), anti-arrhythmic drugs that have neurotoxicity, botulinum toxin, digoxin or other cardiac glycosides, guanethidine, heated fluids including heated saline, hypertonic saline, hypotonic fluids, potassium chloride, cooled or heated neuroablative substances such as those listed above.

It is also envisioned that the ablative substance used for the ablation treatment according to the ablation protocol can be hypertonic fluids such as hypertonic saline (extra salt) or hypotonic fluids such as distilled water. These could cause damage to the nerves and could be as effective as alcohol or specific neurotoxins. These can also be injected hot, or cold or at room temperature. The use of distilled water, hypotonic saline or hypertonic saline with an injection volume of less than 1 ml eliminates one step in the use of the PNASC because small volumes of these fluids should not be harmful to the kidney. Accordingly, this obviates the need to completely flush the ablative fluid from the PNASC with normal saline to prevent any of the ablative fluid getting into the renal artery during catheter withdrawal. This system and method provides the advantage that there would be only one fluid injection step per artery instead of two as would occur if a more toxic ablative fluid were used during ablation.

It is also envisioned that the PNASC could be connected to a heated fluid source to deliver high temperature fluids to ablate or injure the target tissue or nerves. The heated fluid could be normal saline, hypertonic fluid, hypotonic fluid alcohol, phenol, lidocaine, or some other combination of fluids. Injection of hot or vaporized normal saline, hypertonic saline, hypotonic saline, ethanol, distilled water or other fluids via the needles could also be performed in order to achieve thermal ablation of target tissue or nerves at and around the needle injection sites.

The present disclosure also envisions use of anesthetic agents such as lidocaine before the ablation procedure begins in order to provide a local anesthetic/analgesic to reduce or eliminate the pain associated with the denervation procedure.

Various scientific articles have described methods of measurement of nerve activity, yet these have not disclosed obtaining measurements perivascularly from a catheter with sensor that pierce the vessel wall. In a preferred embodiment of this application, external equipment may be provided that interfaces with the proximal end of the catheter. The external equipment may include a display of one or more electrical characteristics of sensed nerve activity such as the peak voltage, average voltage, peak power, average power, one or more bands of power, absolute spectral power, normalized power, inter-burst interval, characteristics of a low-frequency band or a high frequency band, or the ratio between the two, relative spectral power, burst rate, burst duration, spike count, spike rate, correlation (either autocorrelation or correlation between data from 2 or more monopolar or differential sensed channels), correlation of time waveforms or one or more ranges of band-passed sensed activity, and/or coherence. The measurements can be evaluated over a time interval and summary statistics can be provided.

Further measurements may be categorized, sorted, time-locked, correlated, normalized or otherwise evaluated in relation to measures such as blood pressure, a component of the cardiac cycle, heart rate, and/or other measures of the sympathetic and parasympathetic system. The difference between measurements made before and after the provision of a renal denervation procedure can be used to assess the effectiveness of the procedure. Of these nerve measurements, the average voltage would be a preferred measurement. The external equipment could also include a graphical display of the actual sensed signals (after signal conditioning such as amplification and filtering). The electronic equipment can also allow a user to select and define at least one pair of electrodes that is being used to derive a signal that is displayed. For example, a switch control can be provided to enable a user to choose electrode-pair derivations such as 1-2, 2-3 or 3-1, where each electrode is on a different conduit, would be desirable. Other derivations where electrode 1 is referenced to an electrode located distally within a patient could also allow electrical activity to be localized to a more specific degree since the active electrode recording the activity would reflect nerve activity and the reference electrode would not.

Measurement may be made between two electrodes:
both in the perivascular space separated circumferentially,
both in the perivascular space separated longitudinally,
one in the perivascular space and one in the media of the vessel,
one in the perivascular space and one on the intimal surface of the vessel, or
one in the perivascular space and one in the blood stream on the catheter surface.

Similar to the PTAC designs of U.S. Pat. No. 8,740,849 both PNASC and NSC devices of the present application, normally include the control means in the proximal portion of the catheter that serves to limit the needle/wire penetration of the vessel wall which occurs distally. Accordingly, the PNASC and NSC would include one or more manual controllers, such as handles similar to those shown in FIG. 11 of U.S. Pat. No. 8,740,849. In an embodiment, these controllers would be used by the operator to cause first the expansion of the guide tubes and second, the advancement of the needles/electrodes. The reverse motion of these controllers would then retract the needles/electrodes back into the guide tubes and then retract the guide tubes back into the catheter body or under a sheath. Mechanical locking mechanisms can be provided in the handles or elsewhere to prevent accidental movement of the guide tubes and needles are also described by Fischell et al in U.S. Pat. No. 8,740,849 and can be incorporated into the NSC and PNASC embodiments of this disclosure.

Similarly, U.S. Pat. No. 8,740,849 includes disclosure of a proximal section with separate ports for flushing of the catheter lumen and ablative fluid injection that may also be included in the embodiments disclosed in the present application which can have similar structures and controls in the proximal section.

For both PNASC and NSC, conducting insulated wires provide conduction of electrical signals between distal electrodes/sensors and the external equipment attached to the wires near the proximal end of the catheter. The insulated wires would typically run through the body of the catheter.

The PNASC can have radiopaque markers to show, during fluoroscopy, the extension of the needles through the artery wall into the periadventitial space. The NSC also can have radiopaque markers on the sharpened wires to show under fluoroscopy the extension of the wires through the artery wall into the periadventitial space. In both PNASC and NSC, the sensor itself would likely be made of gold or platinum and serve as a radiopaque marker.

Another feature of the presently disclosed PNASC, that ties into the PTAC disclosed by Fischell in U.S. Pat. No. 8,740,849, is a design that reduces the internal volume of the injection lumens of the catheter (the "dead space"). It is anticipated that less than 0.5 ml of an ablative fluid such as ethanol will be needed to perform PeriVascular Renal Denervation (PVRD). The dead space should be less than 0.5 ml and ideally less than 0.2 ml. With certain design features it is conceived that the dead space can be reduced to less than 0.1 ml. Having the insulted wires inside of the fluid injection lumen may further reduce the dead space volume. Such features include using a small diameter <0.5 mm ID hypotube for the inner tube used for fluid injection for the PNASC, and/or designing the proximal injection port and or injection manifold at the proximal end of the PNASC to have low volume by having small <0.5 mm inner diameter and a short, <2 cm length.

In both the PNASC and NSC devices, a wire attached to each distal sensor extends the entire length of the catheter and exits at or near the proximal end. In an embodiment this can occur with the wires exiting through a connector which permits electrical connection to an electronics module. While the preferred embodiment has the insulated wires running within the catheter body, it is also envisioned that the wires could be run outside of the catheter body.

The electronics module can include amplifiers for each sensor (or differential amplifiers for pairs of sensors), filters, analog-to-digital converters to digitize the signals and a central processing unit with memory (CPU) to process the signals and present measures related to nerve activity using a nerve activity visual display. Nerve activity measurements can also be used to drive sonic transducers which provide auditory signals related to the nerve activity or the comparison of nerve activity to a treatment criterion. Auditory feedback and alarms may be provided based upon the measures and/or their assessment in relation to treatment or safety criteria such as thresholds. The electronics module can be high level and allow sensed data from defined pairs of sensors to be displayed and actual measurements of nerve activity displayed. Alternatively, basic nerve activity measurements can be reflected on a low level using a simple 5 LED display for each sensor.

A calibrate button can be used by a user in order to operate a calibration module and to normalize the sensed "nerve activity level" which occurs during or after ablation in relation to baseline measurements made during initial measurement of sympathetic nerve activity which occurred prior to ablation. In one embodiment, all 5 LEDs could be activated to show maximum activity. Following the renal denervation procedure, the user could operate the electronics module to cause a post-therapy measurement to be obtained which can then be compared to the pre-therapy measurements. The reduction in nerve activity between the pre-therapy measurement and the post-therapy measurement would be displayed by illumination of the new level as a normalized value (e.g., if 4 of the 5 LEDs were lit, then the normalized sensed activity would be in the 80% range (+/−10%) of the baseline activity that occurred prior to ablation).

The therapy criteria might be defined as a reduction of the number of diodes that are lit, for example, 0, 1, or 2 out of 5. If the post denervation level is 40% of the normalized level for one of the sensors, then only 2 of the 5 LEDs would be lit showing a 60% drop in nerve activity. An example of even simpler version would have a green, yellow and red LED for various sensors, wherein this example, green indicates normal nerve activity (e.g., in relation to the pre-ablation baseline), yellow indicates a partial reduction and red indicates a significant reduction. In another embodiment, the range used for normal does not need to be derived from a baseline sample for the patient can be a range defined as normal for the population (which can be a population norm value that is adjusted according to demographic variables such as gender and age and may also be adjusted according to physiological measurements of the patient such as blood pressure or according to medication taken by the patient). In another embodiment, instead of using lights, one can use sounds, where a characteristic of the sound (e.g. tone) is increased or decreased according to measurements made on the sense nerve activity.

In an embodiment that used a sensed baseline as a "control" level of activity a processor within the electronics can calculate an average measurement of the sensed activity over at least one specified measurement time interval. The processor could then be configured to compare the post-ablation sensed activity over a similar, or different (e.g. shorter), duration of nerve activity measurement which occurs after ablation therapy. The electronics of a sensing module can be configured to display a quantitative, numerical reduction value (e.g., "Nerve activity reduced by 64% compared to baseline nerve activity.")

As with many of the prior Fischell et al applications cited herein, it is an advantageous feature for certain embodiments of this invention that the guide tubes are needle guiding elements for the advancement of the ultra-thin injection needles or sharpened wires that are advanced outwardly through the wall of the renal artery. Specifically, prior art such as Jacobson that describes curved needles that are advanced outwardly from a central catheter to penetrate the interior wall of a target vessel, have bare needles that are advanced on their own, and without structural support, from the distal end or the side of a catheter. Without additional guiding (support) during advancement, needles that are thin enough to not cause blood loss following withdrawal from the wall of the artery are generally too flimsy to reliably penetrate as desired into the vessel wall.

It is also advantageous to have the pre-set radius of curvature of the guide tubes and injection needles be matched as disclosed in Fischell U.S. patents previously cited.

Thus it is envisioned that a key aspect of the small needle embodiments disclosed in the present application is the inclusion of needle guiding elements such as guide tubes that allow the ultra-thin injection needles to be reliably advanced into the wall of a target vessel to the desired depth. Such guiding elements need not be a tube or have a round cross-section. For example, the structure support can be realized by a half or partial tube, or they can be a structure with a slot that provides a guide for the advance-able needles. A guiding structure could be any expandable structure such as a spring that expands outwardly and provides radial support and/or a guide for the needles. The terms "expand" and "expands" are intended to refer to motion of a structure from a first position relatively closer to a longitudinal axis of the catheter to at least a second position that is relatively farther away from the longitudinal axis, whether the motion is by expansion, deflection, pivoting, or other mechanism. It is desirable that the needle guiding elements expand outwardly from the central catheter.

What is also disclosed in the present application is the use of additional structures to provide radial and lateral support for the needle guiding elements themselves as disclosed by Fischell in U.S. Pat. No. 8,740,849. This is desirable if one seeks a uniform penetration and angular spread of the multiple needles. In addition, as the needles are advanced, and guided by the "guiding elements," (e.g., the guide tubes) the guiding element can, if unsupported, back away from the desired position against the interior wall of the vessel. For this reason, the present disclosure like the PTAC of U.S. Pat. No. 8,740,849 includes the design of structures that provide radial ("backup") support for the needle guiding elements that provide resistance to the guiding elements backing away from the interior surface as the needles are advanced into the wall of the vessel.

There are other medical conditions which may be adversely affected by inappropriate (intrinsic) neurological activity. Early studies suggest that those patients who have undergone renal denervation (with radiofrequency ablation from inside the renal artery) may have improved diabetes and even decreased apnea episodes (in those that have underlying Obstructive Sleep Apnea). Some embodiments of the present invention's ablation device (PNASC) can offer more selective and complete ablation. We believe that with the addition of the sensing characteristics of the catheter that we will be able to tailor the therapy to the desired neuromodulated response.

Another potential application of the PNASC applies to COPD (Chronic Obstructive Pulmonary Disease) that has a potentially reversible component often treated with sympathomimetic agents and also those that decrease (atropine like) parasympathetic tone. Current medical therapy has significant side effects because of the systemic effects of these medications. Use of the PNASC (or PTAC of Fischell et al Ser. No. 13/752,062) to provide focal ablation of parasympathetic system and/or augmentation of the sympathetic system may allow these patients improved pulmonary function without and with fewer oral or inhaled medications.

A feature of the present application is to have a NSC that is percutaneously delivered with outwardly expandable sensors designed to penetrate into and/or through the renal artery wall into the periadvential space where the sensors can be used with associated external electronics to measure sympathetic nerve activity, including changes in the level of sympathetic nerve activity following a renal denervation procedure. Such an NSC could be used with any renal denervation system or device.

A feature of the presently disclosed PNASC is to have a percutaneously delivered catheter with expandable supported needle guiding elements through which injection needles are advanced for injection of an ablative fluid into or beyond the outer layers of the renal artery with sensing electrodes and associated external electronics to measure sympathetic nerve activity, including changes in the level of sympathetic nerve activity following a renal denervation procedure.

Another aspect of the present application is to have an electronics module external to the PNASC or NSC which amplifies the signal from the distal sensors located in the perivascular space and provides a display of nerve activity to allow the user to identify the effectiveness of the nerve ablation procedure such as a renal denervation procedure.

Still another aspect of the present disclosure is to have embodiments with at least three guide tubes/needle guiding elements in the PNASC each having a radiopaque marker. The guide tubes/needle guiding elements being manually expandable outwardly from within a set of tubular shafts which provide additional support and backup to stabilize each guide tube/needle guiding element against the interior wall of the target vessel. Expansion of the guide tubes/needle guiding elements is accomplished by manipulation of a mechanism in the proximal portion of the catheter.

Yet another aspect of the NSC and PNASC of the present disclosure is to include one or more of the following radiopaque markers to assist in positioning, opening, closing and using the PNASC. These include the following:

A radiopaque ring marking the distal end of the outer tube;

Radiopaque markers at, or very close to the ends of the guide tubes using either metal bands or plastic with a radiopaque filler such as barium or tungsten;

Radiopaque markers on the distal portion of the injection needles or sharpened wires;

Radiopaque wires inside the lumen of the injector tubes and/or injection needles;

Wires of radiopaque metals such as gold or platinum to conduct the signals from the distal sensors to the electronics module.

Making the sympathetic nerve sensing electrodes of a radiopaque material such gold or platinum.

The distal fixed guide wire of the PNASC being radiopaque (e.g., using platinum wire);

There is provided in accordance with one aspect of the present invention, a catheter for sensing the activity of nerves outside of the interior wall of a target vessel of the human body. The catheter comprises a catheter body, having a central axis extending in a longitudinal direction and also having a central lumen. At least two needle guiding elements are provided, and adapted to expand outwardly toward the interior wall of the target vessel. At least two needles, each needle having a distal electrode, are adapted to be advanced outwardly guided by the at least two needles guiding elements, to penetrate the interior wall of the target vessel and advance further into the tissue outside of the inside wall of the target vessel. At least two wires are provided for conducting signals sensed by at least two electrodes, the wires connecting the electrodes to external equipment outside of the catheter.

In one implementation of the invention, each needle guiding element is a guide tube, having a lumen, for receiving a needle therethrough. The catheter may include at least three needle guiding elements, three needles, and three insulated wires.

In accordance with another aspect of the invention, there is provided a catheter for sensing the electrical activity of extravascular tissue at a target site. The catheter comprises an elongate flexible body, and at least one flexible extendable arm having a sharpened tissue penetrating tip carried by the body. The extendable arm is movable between a first position in which the tip is positioned within the body and a second position in which the tip is displaced radially outwardly from the body to penetrate tissue and reach the target site. An electrode is carried by the extendable arm, and an electrical conductor extends through the body and is in electrical communication with the electrode.

In one embodiment the catheter comprises three flexible extendable arms. Preferably, a needle support element in the form of a support tube or guide tube is provided for each flexible extendable arm. The support tubes are movable between a first position within the body and a second position extending away from the body. The flexible extendable arms are movable through the support tubes.

In accordance with a further aspect of the present invention, there is provided a dual purpose catheter for both disrupting and evaluating the electrical conductivity of a nerve. The disruption function is provided by application of electrical voltages between at least one pair of electrodes. Such voltages can produce electroshock, electrocautery or RF ablation depending on the amplitude, duration, and frequency of the signal and the material and structure of the electrodes.

In an embodiment, the dual purpose catheter comprises an elongate flexible body, and at least two tissue penetrating probes extendable laterally from the body. A fluid effluent port is provided on each probe, each fluid effluent port in fluid communication with a fluid supply lumen extending through the body. An electrode is carried by each probe, each electrode in electrical communication with a unique conductor extending through the body. Preferably, each tissue penetrating probe is movably advanceable through a tubular support.

In accordance with a further aspect of the present invention, there is provided a method of evaluating nerve ablation in a patient using a catheter system configured to provide sensing of nerve activity and electronics configured for sensing, evaluation, and display of measures derived from sensed data. The method comprises the steps of providing a catheter having an elongate flexible body with a proximal end, a distal end and a first electrode carried by the distal end. The first electrode is movable between a retracted position within the catheter and an extended position for piercing a vessel wall. The electrode communicates signals from the distal end along an electrically conductive conduit to a connector in the proximal end of the catheter which communicates with electronics to provide sensing.

In embodiment of a method, the evaluation of sensed data includes a step wherein the distal end of the catheter is positioned at an intravascular site within the patient. The first electrode is advanced into the wall of the vessel, and an electrical characteristic of one or more nerves is measured. The measuring step may include placing the first electrode and a second electrode into electrical communication with electronics including an instrument electrically coupled to the proximal end of the catheter to receive data from at least the first electrode through the proximal end. The second electrode may be carried by the catheter and can terminate in the proximal end of the catheter, or may be routed outside of the catheter or simply be in contact with the patient's skin.

In accordance with a further aspect of the present invention, there is provided a catheter system for energy based renal denervation from two or more electrodes that are placed more than 2 mm deep to (radially outside of) the location of the pain nerves of the renal artery so as to ablate the sympathetic nerves that are radially outside of the arterial media while reducing the pain to the patient as compared with energy based denervation from inside of the renal artery.

There is provided in accordance with a further aspect of the present invention a catheter system for sensing nerve activity in the volume of tissue just outside of the vessel within the human body. The catheter system comprises electronic equipment designed to measure nerve activity, a first electrode, and a second electrode. The first and second electrodes may be incorporated near the distal end of the catheter, the catheter including a mechanism to position the distal electrodes into the volume of tissue outside of the inside wall of a vessel of the human body. The position of the electrode may be selected to be a location in the outer layer of the vessel wall, or a location in tissue that lies radially outside of the outer layer of the vessel (e.g. extravascular tissue). Conductive wires are adapted to connect the first and second electrodes to the electronic equipment.

In accordance with alternative aspects of the invention, there are provided methods and systems for treatment of extravascular/perivascular tissue such as denervation of renal nerves, while minimizing or eliminating pain to the patient from the ablation portion of the procedure. Pain associated with first generation RF renal denervation devices may be attributable to the nonspecific destruction of nerves associated with the vessel wall. Pain is believed to be associated with destruction of unmyelinated "C-fibers"

which may run in or just outside of the media (smooth muscle layer) of the vessel or in or just outside of the external elastic lamina (outer skin of the media). The sympathetic nerve fibers that affect blood pressure are predominantly the "efferent" nerves that transmit signals from the brain to the kidney and back. These nerves are believed to run almost exclusively in or outside of the outer layer of the artery (the adventitia) and deep to (outside of) the external elastic lamina. Conventional intravascular energy delivery by ultrasound or RF will ablate tissue from the endothelium (the inside layer) of the artery all the way to the adventitia, thus damaging both unmyelinated "C-fibers" causing pain as well as a portion of the sympathetic nerve fibers. Intravascular energy delivery may be limited in efficacy as it is limited in its ability to ablate the sympathetic nerves outside of the adventitia without causing irreparable damage to the artery.

As patients treated with the devices such as the PTAC of U.S. Pat. No. 8,740,849 have been found to experience minimal or no pain during injection of ethanol into or outside of the adventitia (i.e., deep to the pain fibers), delivering any type of ablative therapy (energy, chemical or other modalities) to the adventitia or outside of the adventitia should achieve both a better therapeutic ablation and do so with minimal or no pain. It envisioned that when chemical ablation is performed, a slow (>30 second) injection of the ablative fluid can prevent even the mild, short lived pain that may be felt from a faster injection because the fluid itself serves as an anesthetic. It is noteworthy that locating the distal tip of the electrodes to locations in the adventitia or outside of the adventitia not only increases the effectiveness of ablative agents or energy that is delivered, but also locates the sensing electrodes in one or more locations that are near the relevant nerves in order to measure relevant nerve activity.

Thus, one aspect of the present invention provides a catheter for preferentially denervating efferent nerves while sparing unmyelinated C-fibers adjacent a target vessel. The catheter comprises an elongate, flexible catheter body having a central axis extending in a longitudinal direction; at least two electrode guiding elements adapted to expand outwardly toward the interior wall of the target vessel; at least two electrodes, each electrode having a distal uninsulated electrode tip, the at least two electrodes adapted to be advanced outwardly, guided by the at least two electrode/needle guiding elements, to penetrate the interior wall of the target vessel and position the electrode tips beyond the external elastic lamina.

In a preferred embodiment each electrode guiding element is a guide tube having a lumen. Each electrode may be advanced outwardly coaxially through the lumen of a guide tube. At least three electrode guiding elements and three electrodes may be provided.

A catheter for localized RF ablation of extravascular tissue at a target site while sparing adjacent endothelium, comprises an elongate, flexible body; at least one flexible extendable arm having an electrically conductive tip carried by the body of the catheter, the extendable arm movable between a first position in which the electrically conductive tip is positioned within the body of the catheter and a second position in which the tip is displaced radially outwardly from the body to penetrate tissue of a target vessel and reach the target site, such that the electrically conductive tip is positioned completely beyond the endothelium of a target vessel. In a preferred embodiment, the catheter will include at least three flexible extendable arms. A support tube movable between a first position within the body and a second position extending away from the body may be provided the flexible extendable arm extends through the support tube.

One method of some embodiments of the present invention comprises operating a catheter system designed for preferentially denervating efferent nerves while sparing unmyelinated C-fibers adjacent a target vessel to treat hypertension while minimizing procedure discomfort. The method can comprise the steps of providing a catheter system having an elongate, flexible body with a proximal end, a distal end, and a first electrode carried by the distal end, the first electrode movable between a retracted position within the catheter and an extended position for piercing a vessel wall; positioning the distal end of the catheter at an intravascular site within the patient; advancing the first electrode into the vessel wall at a puncture site; and denervating tissue at a first depth deep to (outside of) the external elastic lamina to preferentially denervate efferent nerves while sparing unmyelinated C-fibers at a second depth near to or within the external elastic lamina, the second depth less than the first depth.

It is also envisioned that the method above can include using the electrodes to sense electrical activity primarily from the efferent nerves and this may occur both before and after ablation so that the sensed data may be evaluated to determine the efficacy of the ablation.

Another aspect of the method of minimizing pain during renal denervation, comprises the steps of advancing a distal end of a catheter transluminally to a site in a renal artery; advancing an ablation element from the catheter, through the media and into the adventitia; and ablating tissue within the adventitia while sparing the media. The ablation element may dispense an ablative fluid delivered from an effluent fluid port. Alternatively, the ablation element may comprise an energy delivery element including at least one of a: radiofrequency (RF), microwave, cryogenic, ultrasound, electrocautery, or heating element.

In any of the foregoing, the ablative element (e.g., conductive surface of an electrode; fluid from an effluent port) is preferably carried by the catheter such that it can penetrate the vessel wall from inside of the vessel and position the ablative element to enable it to selectively ablate tissue at a depth of at least about 3 mm, preferably at least about 5 mm and in some embodiments as far as 10 mm into the vessel wall from the endothelium in the direction of the adventitia, so that it can ablate nerves in and outside of the adventitia minimizing damage to the nerves in or near the media. Preferably the catheter permits blood perfusion through the renal artery during the ablation and/or nerve activity sensing procedures.

An additional reason perivascular energy based ablation will be more effective than intravascular is that it is less damaging to the media that will be cooled by the significant blood flow through the artery, while there is much less cooling in the perivascular space.

One additional aspect of some embodiments of the present invention PNASC that can provide both RF ablation and medication delivery, is that an anesthetic such as lidocaine could be injected before the RF ablation procedure to also provide minimal or no pain to the patient during nerve ablation.

The terms sensor and electrode may be used interchangeably here to describe a conducting electrical contact which forms the distal end of the conduit 20. The terms sharpened wire and needle may be used interchangeably to refer to a sharpened distal portion that penetrates the through a vessel or artery.

The catheter based system of the present disclosure can, in some embodiments, be varied, either by using hollow or solid conduits, and also by adjusting the equipment (e.g., to provide delivery of ablative or anesthetic fluid) and electronics (e.g., for proving sensing, stimulation, and or ablation) that are operated at the proximal end of the catheter. In various implementations the catheter system can serve as, in some embodiments, at least one of the following novel embodiments to provide advantages over the prior art:

a sensing catheter system that can provide sensing that is used to assess ablation provided by a treatment catheter configured to provide ablation such as by RF, ultrasound, or ablative fluid;

the catheter system of (a), further configured to provide non-ablative stimulation in order to provide a stimulus for obtaining sensing of evoked data that is time-locked to the stimulus;

the catheter system of (a) configured with hollow, rather than solid, conduits in order to provide local anesthetic such as lidocaine;

a catheter system that can provide both sensing and ablation, wherein the ablation treatment is provide by RF, ablation fluid, or ultrasound;

the catheter system of (d), further configured to provide non-ablative stimulation in order to provide a stimulus for obtaining sensing of evoked data to measure the health of the sympathetic nerve that is time-locked to the stimulus;

a catheter system configured with hollow rather than solid conduits in order to provide local anesthetic such as lidocaine and also energy based ablation by ultrasound or RF based ablation;

a catheter system of a to f, configured to provide at least one of sensing, stimulation, and ablation in a monopolar or bipolar fashion using at least one distal tip of a conduit;

a catheter system of a to f, configured to provide at least one of sensing, stimulation, and ablation using conduits that pierce the inner wall to reside in the perivascular space outside of a renal artery of a patient; and, a catheter system configured to provide ultrasonic stimulation using a stimulation element residing, at least in part, in the perivascular space outside of a renal artery of a patient.

In order to realize these features and advantages, there will be disclosed a number of main embodiments of the catheter systems including:

Nerve Sensing Catheter (NSC) 10, which utilizes solid conduits at the distal tip of the catheter;

Nerve Sensing Catheter NSC 100, which utilizes hollow conduits at the distal tip of the catheter;

perivascular Nerve Ablation and Sensing Catheter PNASC 200;

perivascular Nerve Ablation and Sensing Catheter PNASC 400; and,

Ultrasound Nerve Ablation catheter UNAC 600. In some embodiments, also disclosed herein is a catheter for sensing the activity from nerves outside of the lumen of a target vessel of a human body. The catheter can include a catheter body having a distal end for insertion into a patient, a proximal end for controlling the movement of at least one needle, and a central axis extending in a longitudinal direction. The catheter can also include a connector configured to connect to external electronic equipment outside of a proximal end of the catheter. The equipment can have a sensing subsystem configured for sensing local nerve activity within a patient, and can be configured to be connected to at least one additional electrode in electrical contact with the patient. The catheter can also include at least one needle guiding element adapted to expand outwardly from the catheter body toward the interior wall of the target vessel. The catheter can also include at least one needle, the needle having at least one distal electrode, the needle adapted to be advanced outwardly, guided by the at least one needle guiding element to penetrate and advance through the interior wall of the target vessel into the tissue outside of the vessel lumen. The catheter can also include at least one wire for conducting electrical signals between the at least one electrode and the connector for communicating with said external electronic equipment.

In the specification that follows, the term conduit will mean a structure in a catheter that can be utilized to transmit electrical energy and/or fluid between a proximal end of the catheter and tissue within a human body.

Throughout this specification the terms injector tube with distal injection needle is used to specify a tube with a sharpened distal end that penetrates into tissue and is used to inject a fluid into that tissue. Such a structure could also be called a hypodermic needle, an injection needle or simply a needle. In addition, the terms element and structure may be used interchangeably within the scope of this application.

The term Luer fitting may be used throughout this application to mean a tapered Luer fitting without a screw cap or a Luer Lock fitting that has a screw cap.

The term needle will be used throughout this disclosure to characterize a small diameter sharpened wire or tube designed to penetrate through the wall of a target vessel, its primary characteristic being a sharpened tip. Thus the distal portion of the sharpened wire as disclosed herein is also a needle.

Any of the terms ablative fluid, ablative solution and/or ablative substance will be used interchangeably to include a liquid, gel, suspension, or a gaseous substance delivered into a volume of tissue in a human body with the intention of damaging, killing or ablating nerves or tissue within that volume of tissue.

Also throughout this specification, the term inside wall or interior surface applied to a blood vessel, vessel wall, artery or arterial wall mean the same thing which is the inside surface of the vessel wall, or the "intimal" surface of the vessel lumen.

Also the term injection egress is defined as the distal opening in a needle from which a fluid being injected will emerge. With respect to the injection needle, either injection egress or distal opening may be used here interchangeably.

The terminology "deep to" a structure is defined as beyond or outside of the structure so that "deep to the adventitia" refers to a volume of tissue outside of the adventitia of an artery.

These and other features and advantages of this invention will become obvious to a person of ordinary skill in this art upon reading of the detailed description of this invention including the associated drawings and the claims.

BRIEF DESCRIPTION OF THE DRAWINGS

FIG. 9 is an enlargement of region S9 of FIG. 8.

FIG. 10 is a transverse cross section at 10-10 of FIG. 9.

FIG. 12 is a longitudinal cross section of another embodiment of the distal portion of the artery penetration portion of the NSC.

FIG. 13 shows a modification of the distal portion of FIG. 12 that modifies the NSC design into a PNASC design by the addition of side holes for fluid injection into the perivascular space.

FIG. 20b is a schematic view of an alternative method for using the PNASC.

DETAILED DESCRIPTION

Figure 1:
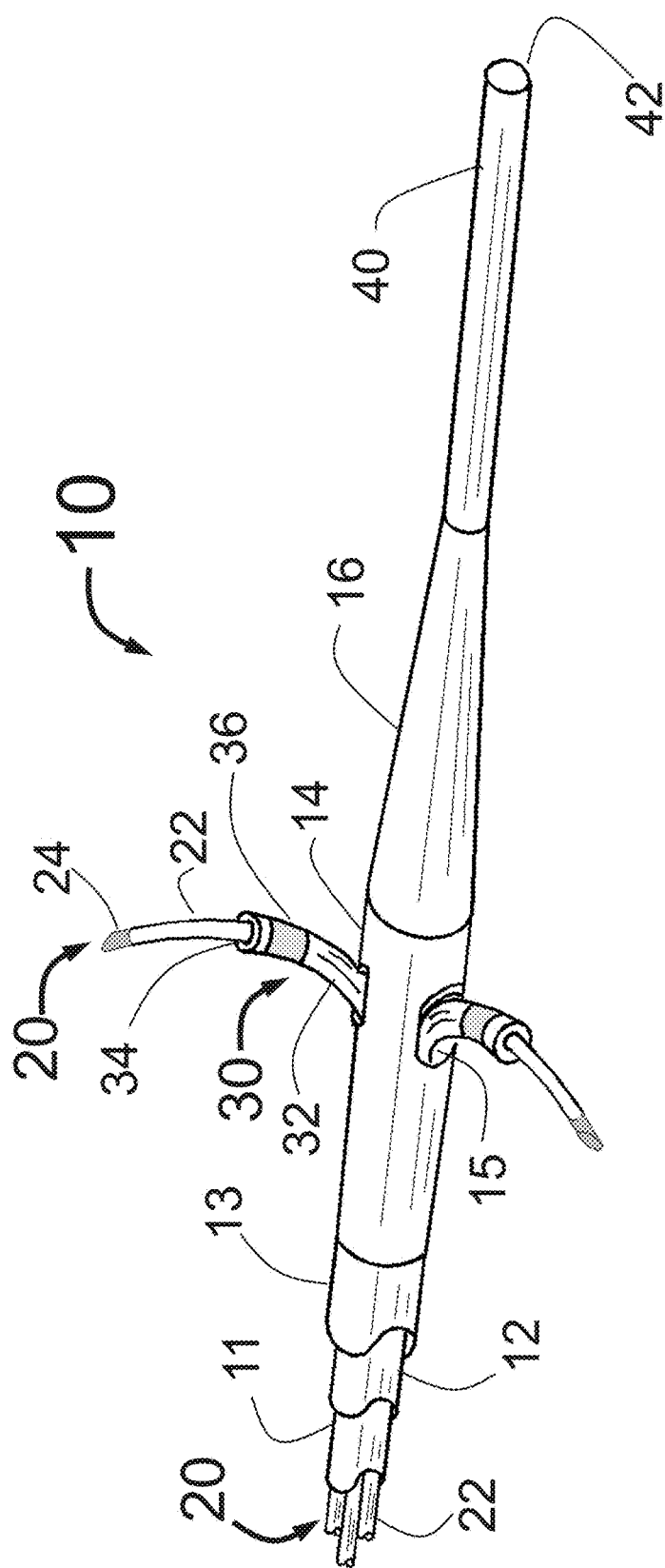
FIG. 1 is a schematic view of the distal portion of an NSC which uses three expandable sharpened wires in its open position as it would be when manually expanded for measurement of the activity of nerves such as the sympathetic nerves outside of the renal artery.

FIG. 1 is a schematic view of the distal portion of a Nerve Sensing Catheter (NSC) 10 that is designed to sense electrical energy (currents or voltages) from extra-vascular tissue within a human body. In some embodiments the NSC may also deliver electrical energy to tissue, for example, to provide for obtaining and assessing evoked activity. The NSC 10 is shown in its open position, showing an inner tube 11, middle tube 12, outer tube 13, outer tube extension 14 having distal openings 15 through which the guide tubes 30 with radiopaque markers 36, distal tip 34 and outer layer 32 are advanced outwardly from the body of the NSC 10. Also shown is the tapered section 16 and fixed guide wire 40 with distal tip 42. The NSC includes three conduits 20 with outer insulation 22, and sharpened wire 24, with 2 of the three guide tubes and conduits shown in their fully deployed positions (the third is not shown). Ideally the sharpened wires 24 are made from or coated with a radiopaque material such as gold or platinum.

Figure 21:
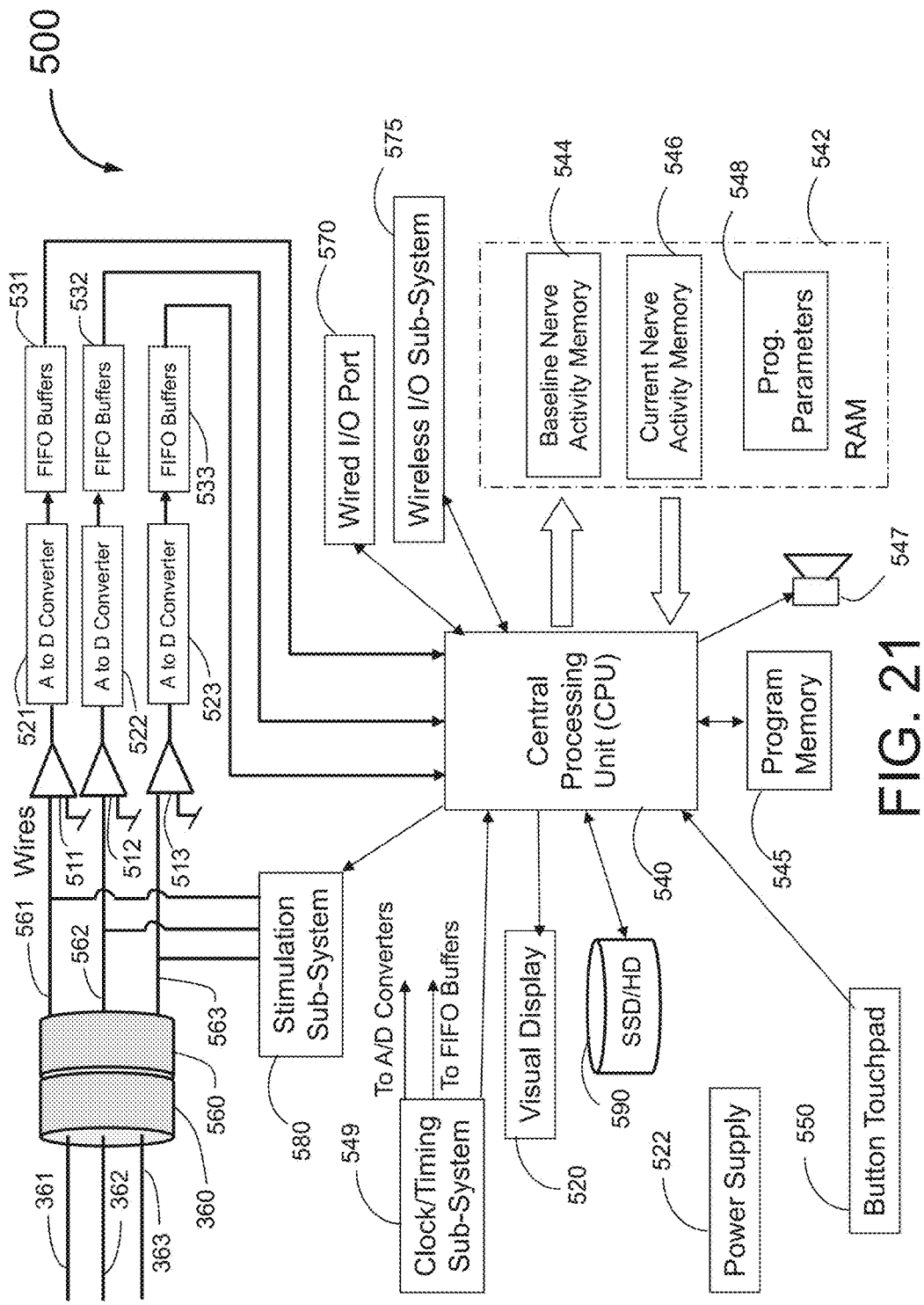
FIG. 21 is a schematic view of the electronics that provide stimulation and/or sensing at the proximal portion of the NSC/PNASC.

The conduits 20 run all the way to the proximal end of the NSC 10 where they interface with electronic equipment 500 that provides sensing (as shown in FIG. 21). The distal tips 24 of the conduits 20 are shown here in the distal portion of the NSC 10. The conduits 20 extend through the catheter body within the lumen of the inner tube 11. The insulation 22 that insulates the conduits within the catheter body does not extend around the most distal portion of the conduit 20 since this portion terminates as a sharpened wire/needle 24 which will penetrate the vascular wall and act as an electrode for sensing nerve activity from a perivascular location.

For purposes of illustration, the conduits 20 of FIGS. 1-5 are realized as solid insulted wires, while the conduits of FIGS. 6-11 are realized as hollow tubes, with the understanding that the two variations of the embodiments should not be considered limiting and may be realized approximately interchangeably, or both may be incorporated into various embodiments, to realize advantages disclosed herein without departing from the scope of the invention.

The openings 15 in the distal portion of the catheter support the guide tubes 30 as the guide tubes 30 are advanced outwardly in order to provide structural support during the subsequent deployment of the conduits 20. Although the NSC 10 of FIG. 1 has three guide tubes 30, it is envisioned that other embodiments could have as few as one or as many as eight guide tubes with an optimum number typically being three or four in the case of renal denervation. A larger diameter target vessel might suggest the use of as many as 4 to 8 guide tubes 30 and conduits 20.

As the different embodiments of the present invention are disclosed, it will become evident that in addition to providing electrical conductivity from the proximal end of the NSC to the distal sharpened wires 24, the conduits 20 may be adapted to be hollow to also provide a passageway for fluid injection near the tip of the sharpened wires 24. A modified version of the NSC is disclosed herein, that provides both nerve sensing and nerve ablation capabilities. This dual function catheter will be called a Perivascular Nerve Ablation and Sensing Catheter (PNASC). In embodiments, the modifications can include:

Providing both electrical sensing and stimulation using the sharpened wires 24 which act as electrodes to both sense nerve activity and provide energy to tissue;

Providing electrical energy such as RF to the sharpened wires 24 that act as electrodes provide energy based ablation;

Having a fluid passageway in the conduits 20 with an egress near the distal end of the sharpened wires 24 for injection of an ablative fluid for chemical nerve ablation and or dispensing an anesthetic/analgesic agent such as lidocaine; or Providing an ultrasound transducer either within the body of the PNASC or in the distal portion of the conduits 20 to provide energy based ablation, such as ablation at perivascular sites that is delivered by the conduits 20.

Different shapes are envisioned for the distal openings (or windows) 15 in the outer tube extension 14 where the guide tubes 30 exit. These possible shapes include and oval or round shapes such as a racetrack design with curved (e.g., round) proximal and distal ends and straight sides in the axial direction. It is also envisioned that there could be a movable flap (not shown) covering each opening 15, or a slit that could be opened to make the outer surface of the NSC smooth for better delivery through a guiding catheter into the renal artery. Such a moveable flap could be operated under the control of the catheter handle in the proximal section of the catheter. The mechanical operation of the catheter can function so that the flaps are retracted prior to the guide tubes 30 being deployed. Alternatively the flaps may be made flexible and soft enough that these are simply pushed aside by the guide tubes 30 upon deployment.

It is a feature of this invention that the guide tubes 30 serve as needle (i.e., conduit) guiding elements that provide structural support for the ultra-thin conduits 20. Specifically, prior art such as Jacobson that describe curved needles that are advanced outwardly from a central catheter to penetrate the wall of a target vessel, have needles that are advanced on their own (naked) from the distal end or side of a catheter. Without additional guiding and support during advancement, needles/sharpened wires that are thin enough to essentially eliminate the risk of bleeding following penetration and withdrawal from the wall of the artery are generally too flimsy to reliably penetrate as desired into the vessel wall. Thus it is envisioned that the NSC 10 of the present application preferably includes needle-guiding elements such as the guide tubes 30 that allow the ultra-thin conduits 20 to be reliably supported and advanced into the wall of a target vessel to the desired depth. The guiding elements also serve to center the catheter within the vessel and to promote reliable, similar, and measured deployment of all three sharpened wire tips 24 through the vessel wall.

As shown in FIG. 1, the three conduits 20, sensors 24 and guide tubes 30 are spaced uniformly around the circumference of the catheter 10 at approximately 120 degrees separation. The uniform spacing improves the sensing performance of the NSC 10. It is also envisioned that the spacing might be non-uniform for example two might be 50 degrees while the third could be 155 degrees from either of the first two.

In an alternative embodiment to that shown in FIG. 1, a catheter for sensing the activity from nerves outside of the lumen of a target vessel of a human body can only include one conduit 20. For the single conduit 20 embodiment, a portion of the body of the NSC 10 such as the outer tube extension 14 will typically be pushed against the inside wall of the artery diametrically opposed to the contact point where the needle guiding element/guide tube 30 expands outward to contact the wall of the artery.

Figure 2:
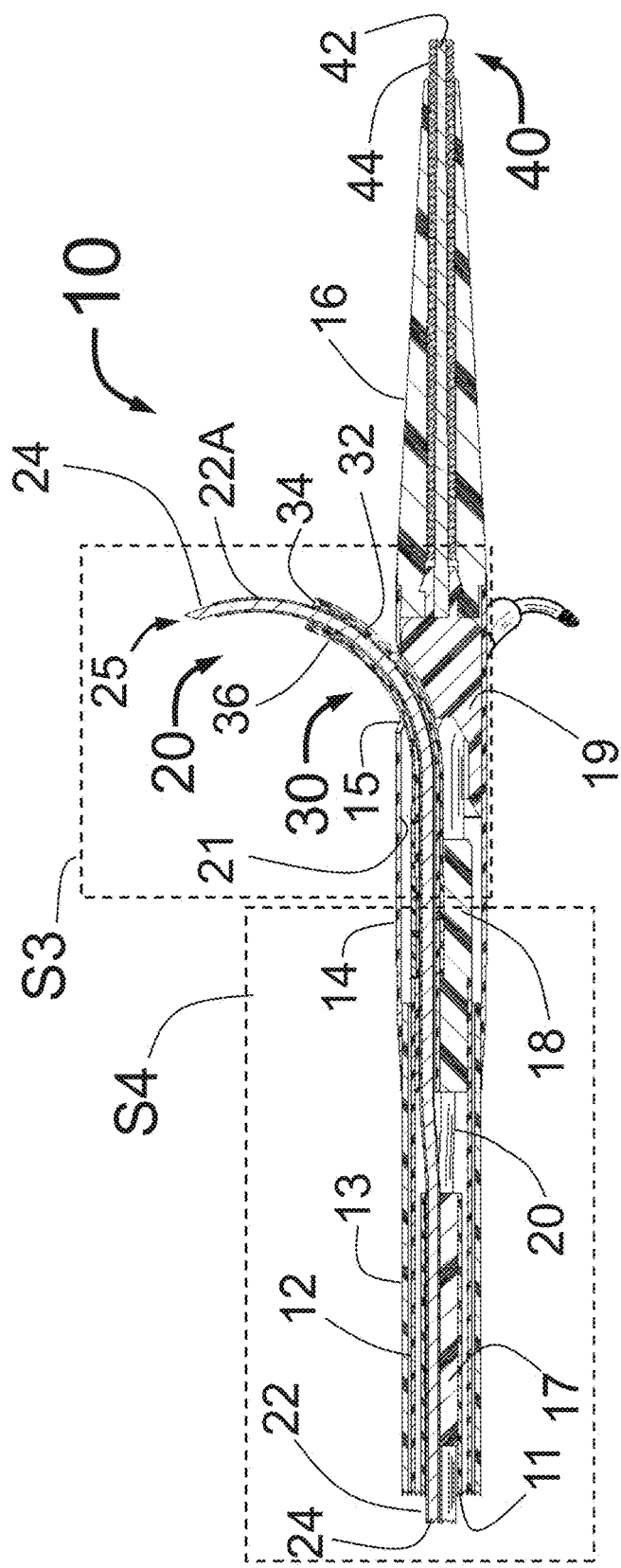
FIG. 2 is a longitudinal cross-section of a distal portion of the NSC of FIG. 1 in its open position.
Figure 3:
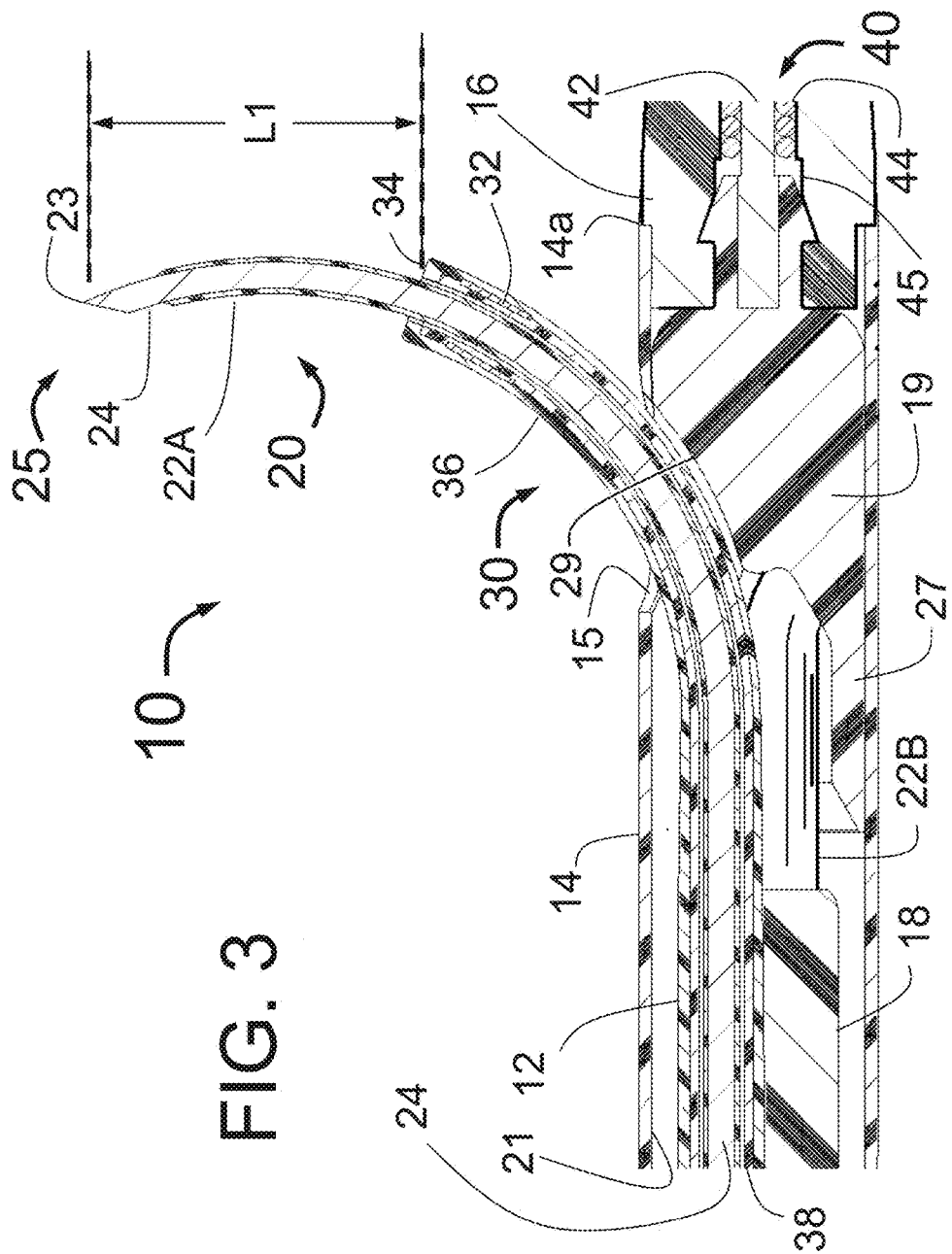
FIG. 3 is an enlargement of region S3 of the NSC of FIG. 2.
Figure 4:
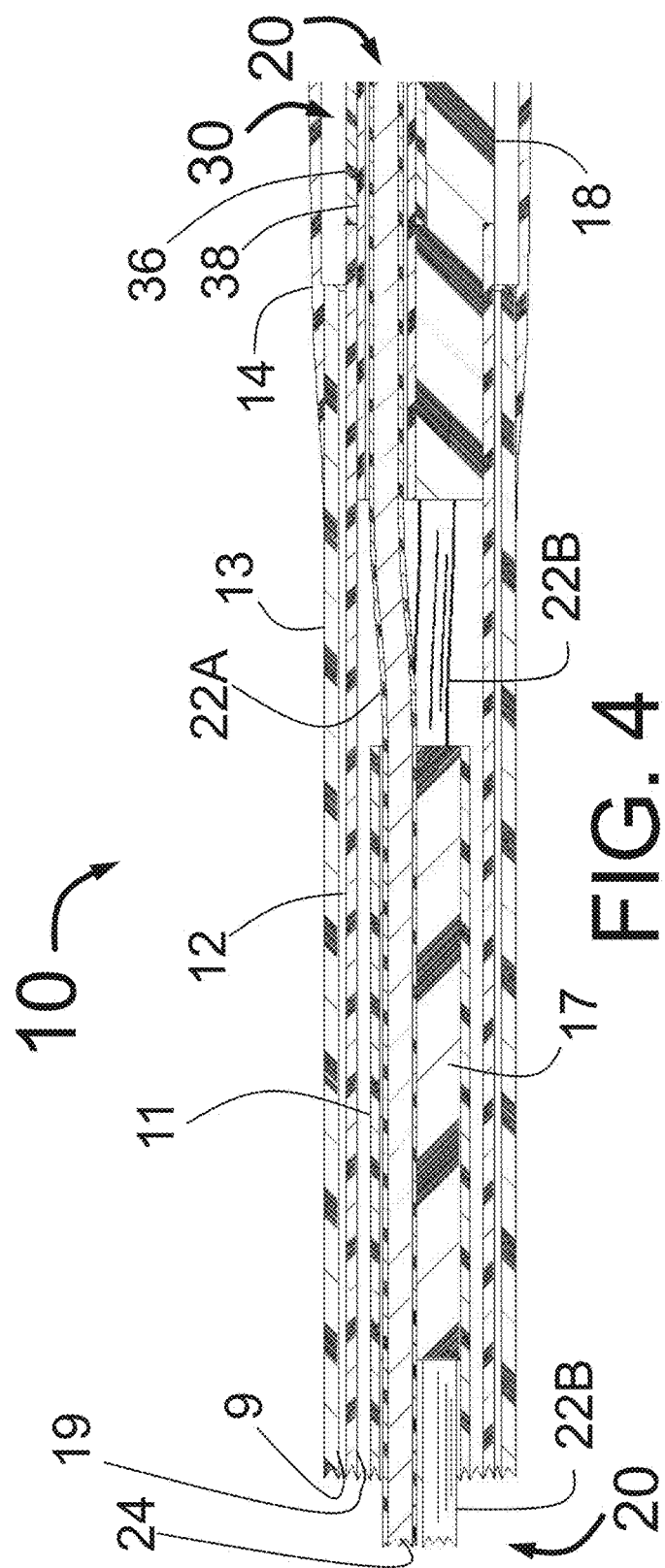
FIG. 4 is an enlargement of region S4 of the NSC of FIG. 2.

FIG. 2 is a longitudinal cross-section of a distal portion of the NSC 10 as shown in FIG. 1. The proximal portion of this figure shown on the left side shows the three concentric tubes, the outer tube 13, middle tube 12 and inner tube 11 which form the central portion of the NSC 10. The outer tube 13 is attached at its distal end to the outer tube extension 14 which is in turn attached to the tapered section 16. The fixed guide wire 40 with core wire 42 and outer layer 44 extends past the distal end of the tapered section 16. It should be noted that only part of the length of the guide wire 40 is shown in FIG. 2, its full length is shown in FIG. 1. Enlargements of the sections S3 and S4 of FIG. 2 are shown in FIGS. 3 and 4 respectively.

FIG. 2 shows two of the three guide tubes 30 with outer layer 32, distal tip 34 and radiopaque marker 36 in their fully deployed positions as advanced through the openings 15 in the outer tube extension 14. The interior surface of the outer tube extension 14 forms part of the tubular shaft 21 that lies within the outer tube extension 14 and which is preferably made from a stiff material such as a high durometer plastic or metal so that the shaft 21 will be relative rigid as the guide tubes 30 are advanced and retracted.

Coaxially within the lumen of the guide tube 30 is the conduit 20 comprising an insulated outer layer 22A and core wire 24 with the exposed sharpened distal tip portion 24. The uninsulated distal portion of the core wire 24 forms the electrode 25 which acts as a sensor. A sensor may operate either in combination with either or both of the other two electrodes 25 at the ends of the other two conduits 20, for example, the first electrode/sensor 25 can be active and can be referenced to the second or third electrode 25 using a differential amplifier of the electronics. The electronics may be used to select which combination of sensors is used during sensing or for stimulation to measure evoked nerve activity as well as whether other sensors (not shown) in other areas may be used to obtain sensed data. The core wires 24 are ideally made from a memory metal such as NITINOL or a stiff springy material such as stainless steel or "L605" which is a cobalt chromium alloy. While L605 is a fairly radiopaque material, if NITINOL or stainless steel is used, the distal portion of the wire 24 should be coated, at least in part, in a radiopaque material such as gold, platinum or tantalum.

A sensor 25 may be referenced to a distally located electrode that is in electrical communication with the patient in order to provide monopolar sensing in relation to the renal nerve activity recorded from the distal tip sensor 25. It is well known to those skilled in the art that various sensing montages may be implemented, but the advantage of the current invention is that one or more sensors can be used to measure nerve activity of the sympathetic nerves while located in the perivascular space outside of a renal artery of a patient after being deployed from an intravascular location.

In one configuration of the NSC, nerve sensing is performed in a responsive method where one or more electrodes 25 may be used to provide both non-ablative electrical stimulation and also sensing in order to assess evoked, "time-locked", or "synchronized" nerve activity, or to provide nerve stimulation in order to evoke a different type of change which may be assessed, for example, by a distally located sensor (e.g., a blood pressure or distally located ECG sensor).

When the catheter system is configured as a PNASC for electrical ablation, then the electrodes 25 can be configured to provide either bi-polar or monopolar electrical energy delivery.

Figure 5:
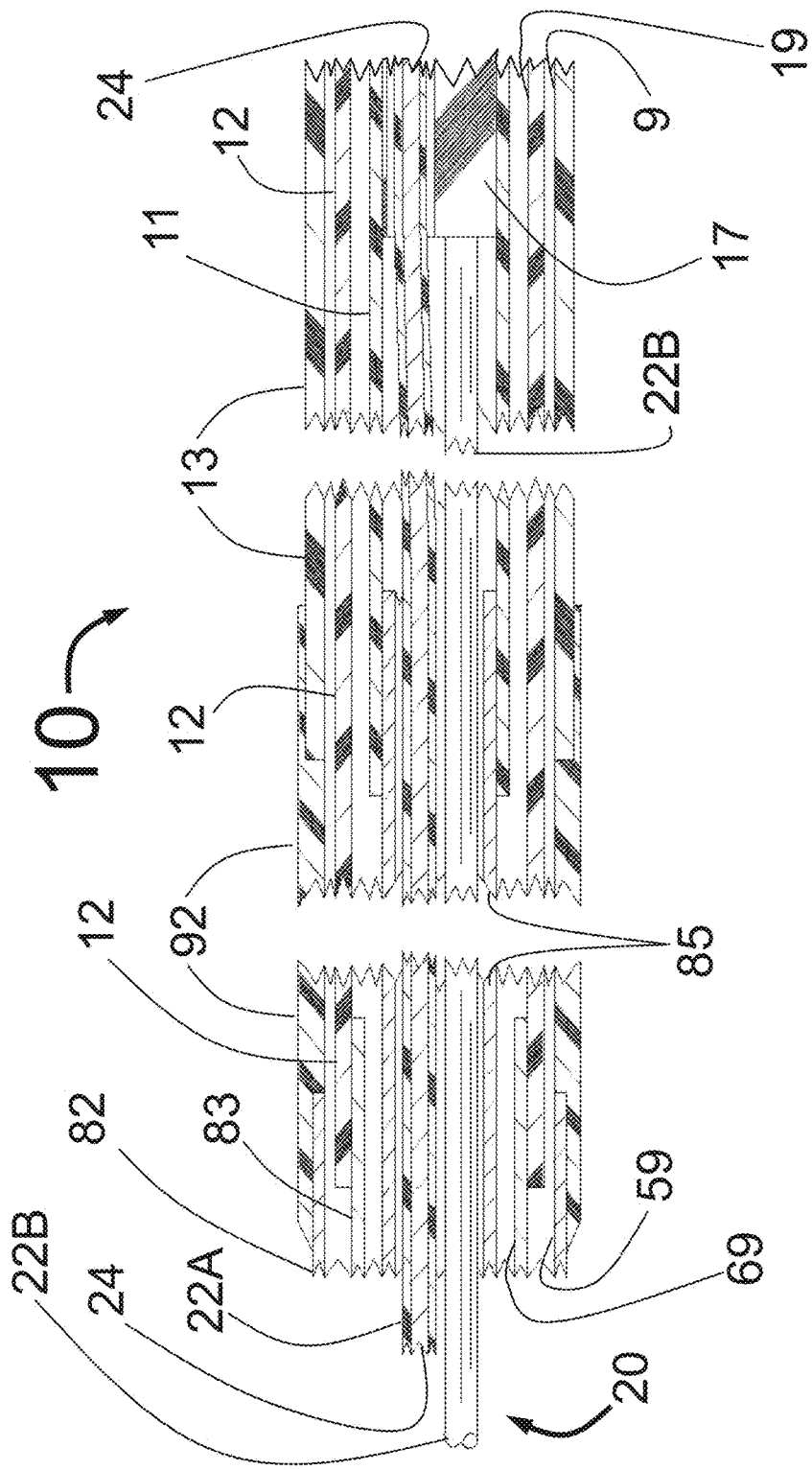
FIG. 5 is a longitudinal cross-section of the central portion of the NSC showing the three proximal hypotubes.

The central portion of the NSC 10, which is more proximal than the portion labeled S4, is shown in FIG. 5.

As shown in FIG. 3, the central buttress 19 shown in FIG. 2 supports the guide tubes 30 both as these are pushed distally and after they are fully deployed. This central buttress 19 also provides radial support for the advanced guide tubes 30 that prevents the guide tubes 30 from backing away from the interior wall of the target vessel as the conduits 20 are advanced through the guide tubes 30 forward and the electrodes 24 arrive at their desired positions such as in the periadventitial space 2-10 mm beyond the interior wall of the target vessel. Additional lateral support for the guide tubes 30 are provided by the sides of the openings 15 that, in combination with the central buttress 19, provide both radial and circumferential/lateral support. The support can in some embodiments be advantageous both during guide tubes 30 advancement and their outward expansion as well as providing additional support during delivery of the injection needles of the conduits 20 through the interior wall of the target vessel. The buttress may comprise a deflection surface such as a curved or linear ramp, which may, in a curved embodiment, correspond to the curvature of the outer surface of the guide tubes 30.

In one configuration, another feature of the NSC 10 (or the PNASC modified versions) is that each conduit 20 is biased to have a central axis with the same, or nearly the same, radius of curvature as the central axis of its corresponding guide tube 30 when measured in an unconstrained state. In addition, the length of the guide tubes 30 is preferably at least as long as the distal curved portion of the conduits 20. This design constrains the curved portion of each conduit 20 within the lumen of the guide tube 30 so that the conduit 20 cannot twist or change position.

Figure 17:
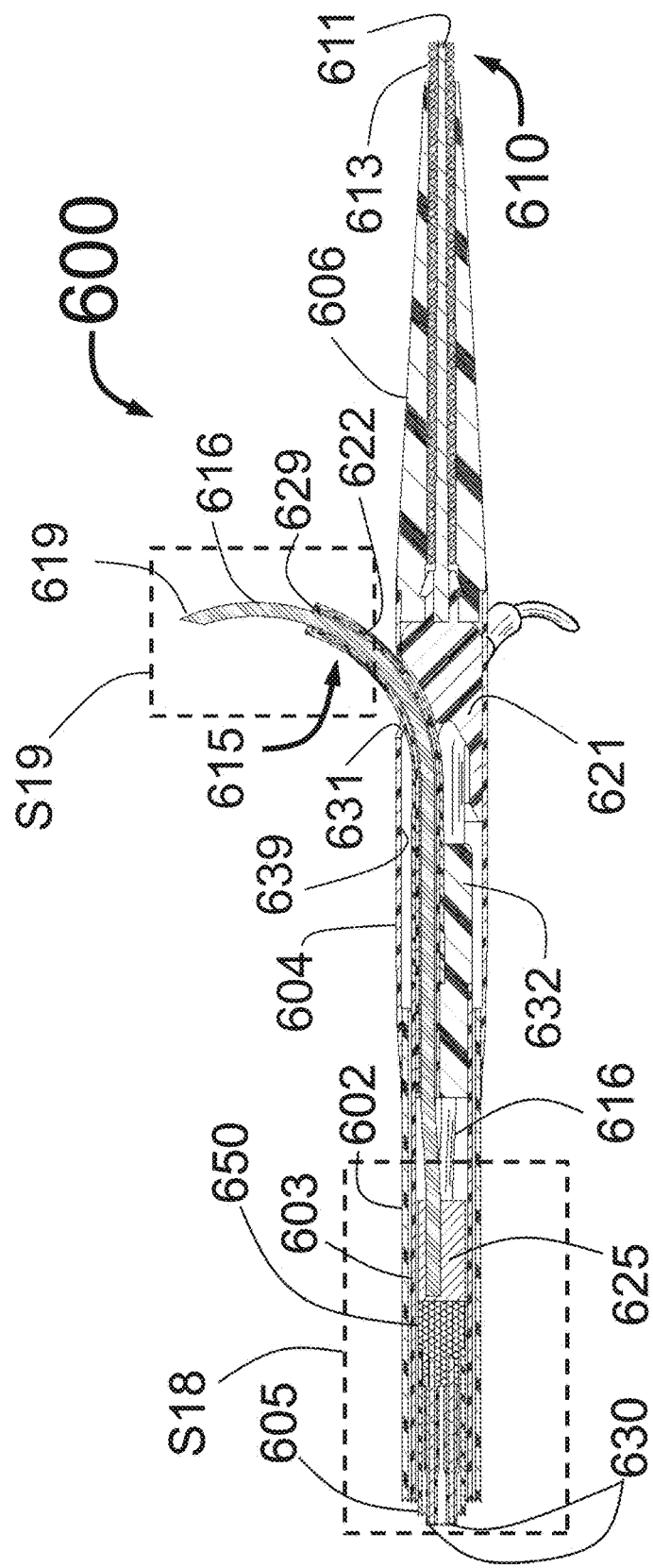
FIG. 17 is a longitudinal cross section of the PNASC configured for providing ultrasound-based nerve ablation.

An example of a design for the distal portion of the central buttress 19 is shown in greater detail in FIG. 17 of U.S. Pat. No. 8,740,849.

As seen in FIG. 2 the plastic cylinder 17 attaches the inner tube 11 to the three conduits 20. The inner tube 11 and plastic cylinder 17 can slide along the longitudinal axis of the NSC 10 inside of the middle tube 12 which is shown with uniform diameter over its length including the portion coaxially outside of the plastic cylinder 17. The middle tube 12 attached to the guide tube connectors 18 under the control of the catheters handle mechanisms to cause the advancement and retraction of the guide tubes 30. The inner tube 11 attached to the plastic cylinder 17 under the control of the catheters handle mechanisms to cause the advancement and retraction of the conduits 20.

FIG. 3 is the enlargement of section S3 of the longitudinal cross-section of the NSC 10 as shown in FIG. 2. FIG. 3 shows the details of the guide tubes 30 with interior layer 38, outer layer 36, distal end 34 and radiopaque marker 32. Coaxially within the lumen of the guide tube 30 is the conduit 20 with insulated outer layer 22A and core wire 24 with needle tip 23. The uninsulated distal portion of the conduit 20 which is the core wire 24 forms the electrode 25 for sensing nerve activity such as sympathetic nerve activity in the perivascular space outside of the renal artery. The other two of the three conduits 20 also have their own respective insulated layers 22B (shown in cross section for a different injection needle) and 22C (not shown). Radiopacity of the tip of each of the conduits 20 can in some embodiments be important so that it can clearly be seen that the needle tips 23 are situated in an intended location such as in the perivascular space. This can be accomplished by using a dense metal such as gold or platinum for the core wire 24 or by attaching a radiopaque marker at or near the tip 23 of the core wire 24. Plating the needle tip 23 with gold could also be effective.

The guide tubes 30 are advanced out of, and retracted back into, the tubular shaft 21 through distal openings 15. In one embodiment, the three guide tubes 30 are attached to each other near their proximal ends by the guide tube connector 18. FIG. 3 also clearly shows how the guide tube 30, when advanced against the central buttress 19 is forced outwardly and is supported by the curved ramp 29 of the central buttress 19 as well as the sides of the opening 15 of the tubular shaft 21. The central buttress 19 also has proximal fingers 27 that provide additional lateral support for the guide tubes 30.

The outer tube extension 14 connects at its distal end 14a to the tapered section 16 which in turn lies coaxially around the guide wire 40 with core wire 42 and outer layer 44.

Figure 16:
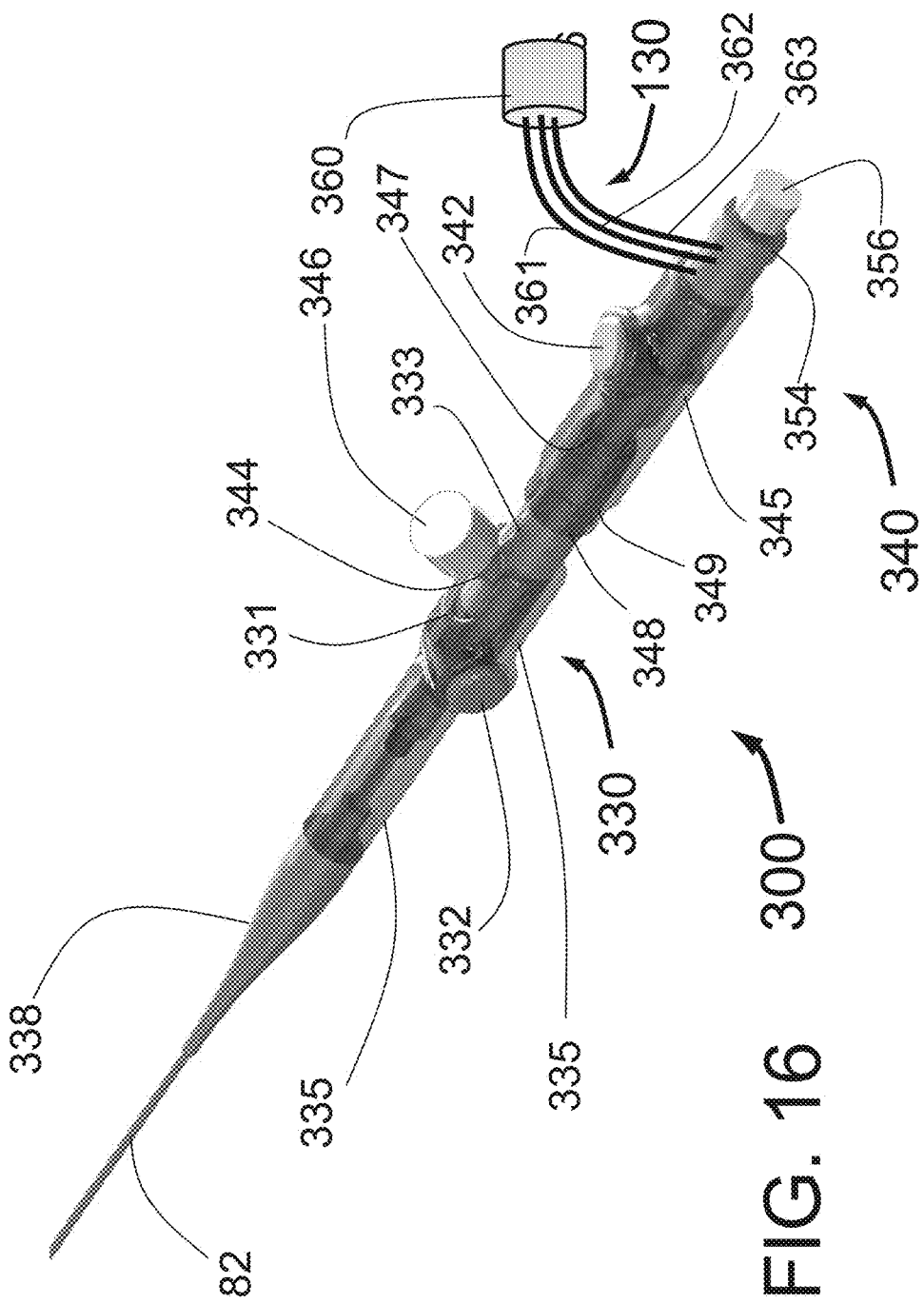
FIG. 16 is a schematic view of the mechanisms at the proximal portion of the NSC/PNASC.

Also shown in FIG. 3 is the penetration depth L1 which is the distance from the distal end of the guide tube 34 to the distal end 23 of the core wire 24. Mechanisms at the proximal section of the NSC 10 (e.g., the proximal handle 300, as shown in FIG. 16) control the motion of the distal components of the NSC 10 including the guide tube 30 and the conduits 20. In one embodiment, the proximal section also includes the mechanisms to limit and/or adjust the penetration depth L1 of the distal end 23 of the conduits 20. In another embodiment the proximal section also includes mechanisms to adjust the deployment length of the guide tubes 30 similar to the mechanisms used to adjust or limit the depth of penetration of the conduits 20 beyond the distal end of the guide tubes 30.

It is envisioned that the central buttress 19 and distal openings 15 can, as shown in FIG. 3, be separate components of the NSC 10 or they can be formed as a single molded or machined part as is shown in FIG. 17 of Fischell et al U.S. Pat. No. 8,740,849. The distal tip 45 of the central buttress 19 provides the attachment to secure the buttress 19 to the tapered section 16. Additionally, the buttress 19, distal openings 15 and tapered section 16 could be a single molded or machined component.

While a preferred embodiment of the NSC 10 has the guide tubes 30 with a pre-formed curved shape, flexible naturally straight guide tubes are also envisioned where the buttress 19 forces the straight guide tubes to curve outwardly for extension through the interior wall of the target vessel.

While the term "central buttress" will be used herein, the key function of the buttress 19 is the deflection surface such as ramp 29 that provides both radial and lateral support for the deployed guide tubes 30. Specifically, the curved ramp 29 of the buttress 19 supports and guides the outward motion of the guide tubes 30 as they exit though the distal openings 15 and also provides radial support for the guide tubes 30 and conduits 20, as they come into contact with (engage) and then pierce through the interior wall of the target vessel. Additional lateral support is provided by the fingers 27 of the central buttress 19 and the sides of the tubular shaft 21 and sides of the openings 15. Such lateral support ensures that the guide tubes move radially outward without deflections in the circumferential (transverse to the longitudinal axis of the catheter) direction.

While the central buttress 19 shown in FIG. 3 is a plastic part, a radiopaque metal part, such as stainless steel, or a coating, or a plastic material that includes radiopaque filler such as tungsten could be advantageously employed for showing the exact location where the guide tubes 30 will exit the NSC 10. It is also envisioned that a radiopaque marker could be attached to a portion of the openings 15 or buttress 19 or outer tube extension 14 to show the likely spot where the guide tubes 30, and thus the conduits 20, would engage the interior wall of the target vessel.

Many of the components of the NSC 10 are typically made from plastic materials such as polyamide, polyurethane, nylon or tecothane. These include the outer tube 13, middle tube 12 and inner tube 11, the outer tube extension 14, inner layer 38 and outer layer 36 of the guide tubes 30, the tapered section 16, the buttress 19, the guide tube connector 18 and the plastic cylinder 17. The plastic cylinder 17 (shown in FIG. 2) can be a molded part or be epoxy or another resin that is injected to affix the conduit wires 20 together within the lumen of the inner tube 11.

It is also envisioned that any or all of the inner tube 11, middle tube 12 or outer tube 13 could also be a metal hypotube or a metal reinforced plastic tube.

The conduits 20 would typically be made of a springy or shape memory metal such as nitinol or a denser metal such as the cobalt chromium alloy L605. It is also envisioned that to enhance radiopacity, the uninsulated distal ends 23 of the wires 24 could be plated in gold or other radiopaque material. Another way could be to have a gold cap attached to the distal end needle tip 23 of the core wire 24. The insulated layers 22A, 22B and 22C are of a plastic material or any insulating coating. The guide tube 30 radiopaque marker 32 could be made of a radiopaque material such as gold, platinum or tantalum or an alloy of these or similar metals. The core wire 42 of the fixed guide wire 40 would typically be stainless steel and the outer layer 44 would be wrapped platinum or platinum iridium wire. The outer layer could also be a polymeric material. Any or certain portions of the outside of the NSC 10 could be lubricity coated to provide improved performance. In typical embodiments for renal nerve ablation, the conduits 20 should be smaller than 0.5 mm in diameter and preferably less than 0.3 mm in diameter to avoid any blood loss or leakage as the conduits 20 penetrate into the wall of the target vessel and are then removed.

While a solid wire 24 is shown in FIG. 3, it is clear that a wire tube could be used in its place that would allow fluid injection as well as sensing or stimulation to occur from this embodiment. In an embodiment, if fluid is to be injected through the conduits 20 then the inside of the conduit lumen could be coated to provide electrical insulation and deter or dampen any potential interaction between the fluid and the electrical signal that are both transmitted along the wire tube.

FIG. 4 is the enlargement of section S4 of FIG. 2 showing the transition from the central portion of the NSC 10 to the distal portion of the NSC 10, including the outer tube 13, middle tube 12 and inner tube 11. Also shown is the connection between the outer tube 13 and the outer tube extension 14.

The guide tube connector 18 connects the three guide tubes 30 to the middle tube 12 that provides the impetus for advancement and retraction of the three guide tubes 30. The motion of the middle tube 12 is produced by the motion of control mechanisms at the proximal end of the NSC 10. The plastic cylinder 17 lies inside of the distal portion of the inner tube 11 and connects together the three conduits 20 with core wires 24 and insulated layers 22A, 22B and 22C (not shown), so that advancement and retraction of the inner tube 11 provides simultaneous advancement and retraction of the conduits 20. Also shown in FIG. 4 are the flushing spaces between the several tubes. Specifically shown is the outer annular space 9 between the middle tube 12 and the outer tube 13 and the inner annular space 19 between the inner tube 11 and the middle tube 12. Each of these spaces 9 and 19 are to be flushed through with normal saline solution prior to insertion of the NSC 10 into the patient's body.

FIG. 4 also shows how the conduit 20 with insulating layer 22A extends from the distal end of the plastic cylinder 17 inside the distal end of the inner tube 11 and then enters the lumen of the inner layer 38 of the guide tube 30 at the proximal end of the guide tube 30. The guide tubes 30 and guide tube connector 18 are attached coaxially within the distal section of the middle tube 12. Thus longitudinal motion of the middle tube 12 will cause longitudinal motion of the guide tube connector 18 and guide tubes 30 thus allowing the mechanism at the proximal section of the NSC 10 to advance and retract the guide tubes 30 with respect to the outer tube 13 and outer tube extension 14.

The penetration depth limitation advantage of the catheter system 10 could be realized in various manners. In one embodiment, this is accomplished using a mechanism that limits the forward motion of the distal end of the inner tube 11 with respect to the guide tube connector 18. For example, a ring or other structure situated between the distal end of the inner tube 11 or plastic cylinder 17 and the proximal end of the guide tube connector 18 would limit the forward (towards distal end of the catheter) motion of the distal end of the inner tube 11 and thus limit penetration of the conduits 20 beyond the distal ends 34 of the guide tubes 30. Such an extension limiting structure could be unattached, or attached to at least one internal structure of the NSC 10 shown in FIG. 4 such as the inner tube 11, plastic cylinder 17, conduits 20, guide tube connector 18, proximal ends of the guide tubes 30 or the middle tube 12. Such an extension limiting structure could also have a length adjustment such as screw threads that would allow it to be used by a user prior to, or after, insertion in a patient to adjust or calibrate the penetration depth L1 of the conduits 20 beyond the distal ends 34 of the guide tubes 30. The structure of the NSC 10 shown in FIG. 4 is similar to that of FIG. 5 of Fischell et al U.S. Pat. No. 8,740,849. While U.S. Pat. No. 8,740,849 shows transverse cross sections for clarity they will not be shown here as they are nearly identical except that in the illustrated embodiments the injector tubes with a platinum core wire are now the conduits 20. As will be discussed, in some embodiments, the insulated conduits 20 may be realized as either solid wires or hollow wires which allow fluid to be provided at the distal tips 23 such as to provide, for example, fluid-based ablation (when embodied as an PNASC), an ablative fluid, saline, or anesthetic fluid as part of the procedure. Accordingly, in addition to the distal tips 23 serving as sensors, the conduits 20 may be configured to provide fluid related to a sensing procedure.

FIGS. 8-11 of U.S. Pat. No. 8,740,849 also show a set of schematic views that illustrate how the PTAC 100 disclosed therein is used for perivascular renal denervation. The same schematic views are applicable in embodiments of the NSC 10 of the current invention with conduits 20 replacing the injector tubes with sharpened distal needles of the PTAC 100.

FIG. 5 illustrates longitudinal cross-sections of the three portions of the central section of the NSC 10 of FIGS. 1 through 4 representing its proximal, central and distal portions. At the proximal end of the proximal portion of the NSC 10 are three concentric metal hypotubes, an outer hypotube 82, middle hypotube 83 and inner hypotube 85. These are typically made from thin walled metallic tubing such as stainless steel, L605, cobalt chromium or nitinol and provide the mechanical means for moving the distal guide tubes 30 and conduits 20 with respect to the outer tube extension 14. The outer hypotube 82 of the NSC 10 attaches at its distal end to a proximal portion of the plastic outer tube 92 typically made from a relatively high durometer plastic, for example polyimide. As seen in the central portion of FIG. 5, the proximal plastic tube 92 attaches at its distal end to the proximal end of the outer tube 13 also shown in FIGS. 1 through 4. The outer tube 13 is typically made from a lower durometer/more flexible plastic than the proximal plastic tube 92. As shown in the proximal section of FIG. 5, the middle hypotube 83 is attached at its distal end to the middle tube 12. As shown in the central section of FIG. 5 the inner hypotube 85 is attached at its distal end to the proximal end of the inner tube 11. Thus the NSC 10 from proximal to distal goes from relatively inflexible metal hypotubes 82, 83 and 85 to more flexible plastic tubes 13, 12 and 11. This allows the distal section of the NSC 10 to be more easily advanced through a guiding catheter in the aorta whose distal end is positioned near the ostium of a renal artery.

Also shown in distal section of FIG. 5 is the plastic cylinder 17 that connects the inner tube 11 to the conduits 20 as shown in FIG. 4. The plastic cylinder 17 allows movement of the inner tube 85 that in turn moves the tube 11 to move all three conduits 20 in the proximal and distal directions FIGS. 6 through 11 show an alternative embodiment of the NSC 100 which is different than that shown in FIGS. 1, 2 and 3 in that the conduits 120 are configured to be hollow while the conduits 20 of FIGS. 1-5 were disclosed mainly as solid insulted wires. The conduits 120 include a sensor tube 116. Inside the sensor tube 116 is an insulated wire 133 (of FIG. 7) that connects to a distal electrode 117. The sensor tube 116 is in certain embodiments will be an electrode when it is connected to the electrical equipment at the proximal end of the PNASC.

Like the NSC 10 of FIGS. 1-5, the embodiments of FIGS. 6-11 may be used for purely sensing nerve activity, non-ablative electrical stimulation of nerves and/or as a Perivascular Nerve Ablation and Sensing Catheter (PNASC). Ablation may occur using electrical (e.g. RF) or fluid ablation of nerves. The primary difference between the NSCs 10 and 100 is that the hollow metal sensor tubes 116 can act as a reference for the electrode tip 117 allowing bipolar sensing and stimulation to occur at each of the conduits 120.

Figure 6:
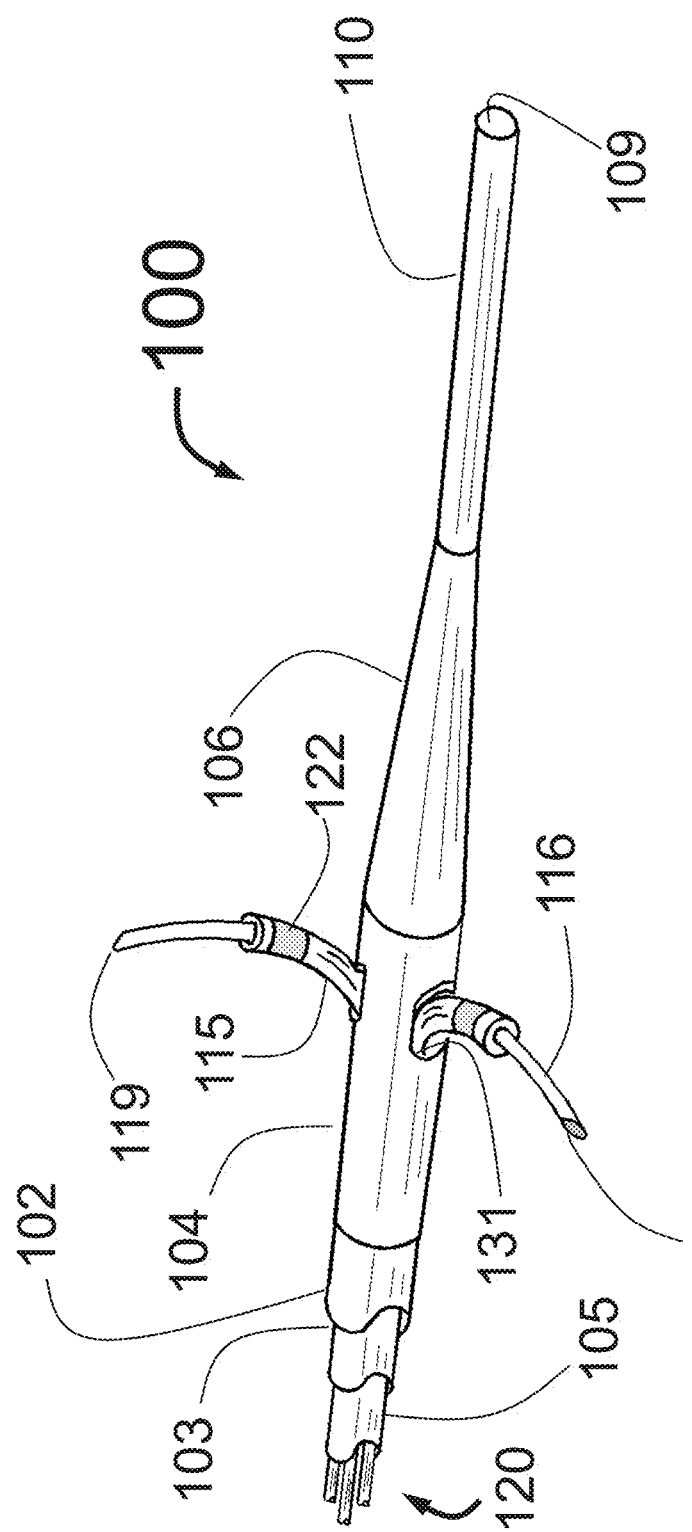
FIG. 6 is a schematic view of the distal portion of either the NSC or PNASC both of which use three expandable NITINOL tubes with distal electrodes that act as sensors for nerve activity. The view shows the NSC or PNASC in the open position following manual expansion.

FIG. 6 is a schematic view of the distal portion of a NSC 100 in its open position, showing an inner tube 105, middle tube 103, outer tube 102, outer tube extension 104 having distal openings 131 through which the guide tubes 115 with radiopaque markers 122 are advanced outwardly from the body of the NSC 100. Also shown is the tapered section 106 and fixed guide wire 110 with distal tip 109. The conduits 120 with central wires 133 with insulation 134 of FIG. 7 and distal electrodes 117 carry the signals sensed by the electrodes to an electronics module for monitoring and measuring the activity of the sympathetic nerves, or providing current for electrical stimulation and/or nerve ablation.

The sensor tubes 116 with distal sharpened sensing needles 119 and sensing electrode 117 are shown in their fully deployed positions. The sensor tubes 116 are ideally made from a memory metal such as NITINOL or a stiff springy material such as stainless steel or L605 a cobalt chromium alloy.

The openings 131 in the outer tube extension 104 support the sides of the guide tubes 115 as the guide tubes 115 are advanced outward against the wall of a vessel before the advancement of the conduits 120. The NSC 100 of FIG. 6 has three guide tubes with the third tube hidden behind the catheter and not visible in this schematic view. Although the NSC 100 of FIG. 6 has three guide tubes 115, it is envisioned that other embodiments could have as few as one or as many as eight guide tubes with a typical number being three or four when provided for renal nerve ablation. A larger diameter target vessel might suggest the use of as many as 4 to 8 guide tubes 115 and sensor tubes 116. The primary structure of the NSC 100 is based on the design of the PTAC 100 of FIG. 2 of U.S. Pat. No. 8,740,849 except that the NSC 100 may be used to sense nerve activity instead of deliver ablative fluid into the peri-adventitial space. In the embodiment shown, the open position may be approximately that which places the sensors in the periadventitial space to allow measurement the activity, or used for energy or chemical based ablation of the sympathetic nerves outside of the renal artery.

Different shapes are envisioned for the distal openings (or windows) 131 in the outer tube extension 104 where the guide tubes 115 exit. These possible shapes include a racetrack design with curved (e.g., round) proximal and distal ends and straight sides in the axial direction, and oval or round shapes. It is also envisioned that there could be a movable flap covering the opening 131 or a slit that could be opened to make the outer surface of the PTAC smooth for better delivery into the renal artery.

It is a feature of some embodiments of this invention that the guide tubes 115 act as needle guiding elements for the ultra-thin conduits 120. Specifically, prior art such as Jacobson that has curved needles that are advanced outward without a guiding element from a central catheter to penetrate the wall of a target vessel. Without additional guiding and backup support during advancement, needles that are thin enough to essentially eliminate the risk of extravascular bleeding following penetration and withdrawal from the wall of the artery are generally too flimsy to reliably penetrate as desired into the vessel wall.

Figure 7:
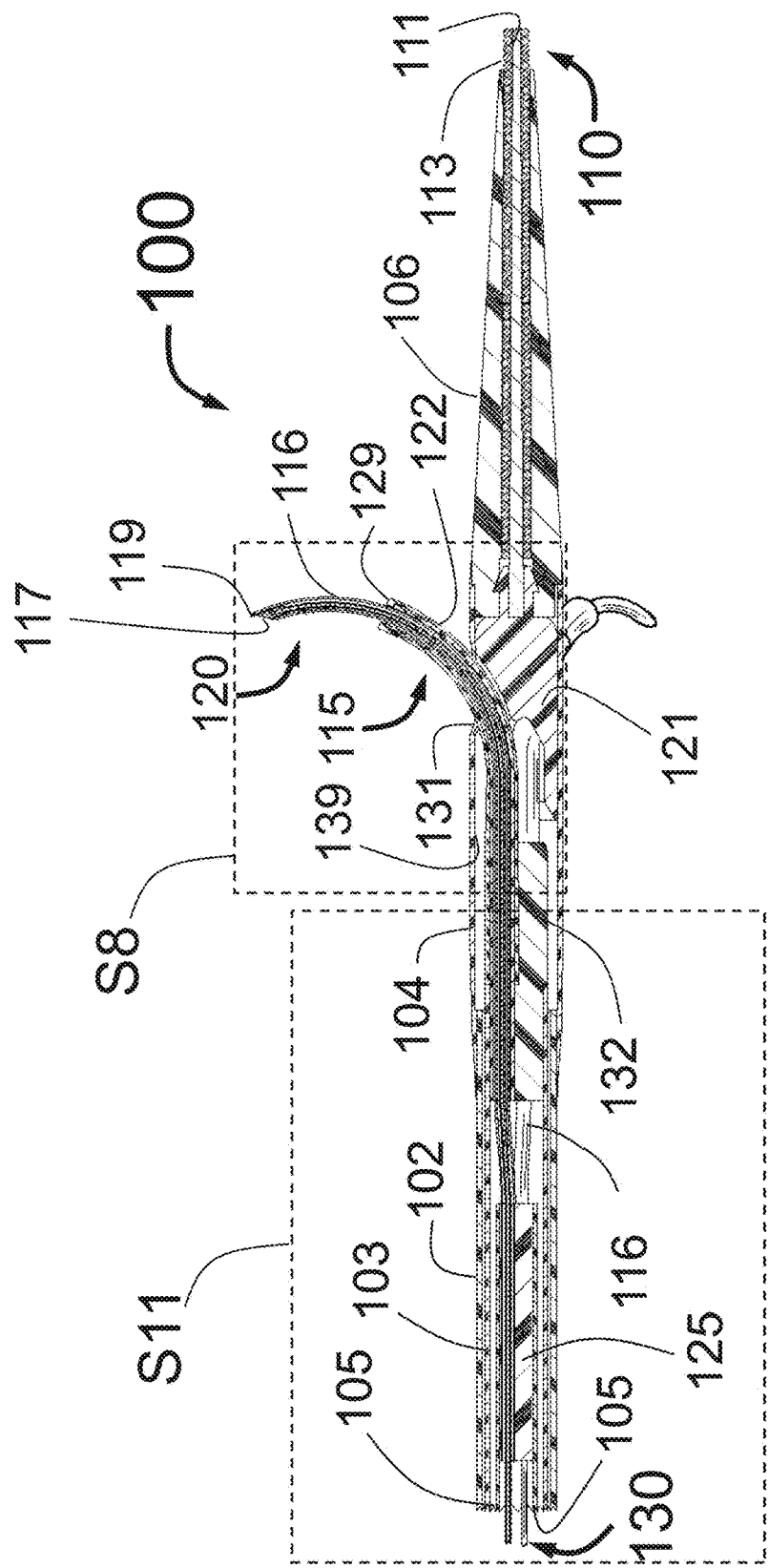
FIG. 7 is a longitudinal cross-section of a distal portion of the NSC of FIG. 1 in its open position.
Figure 8:
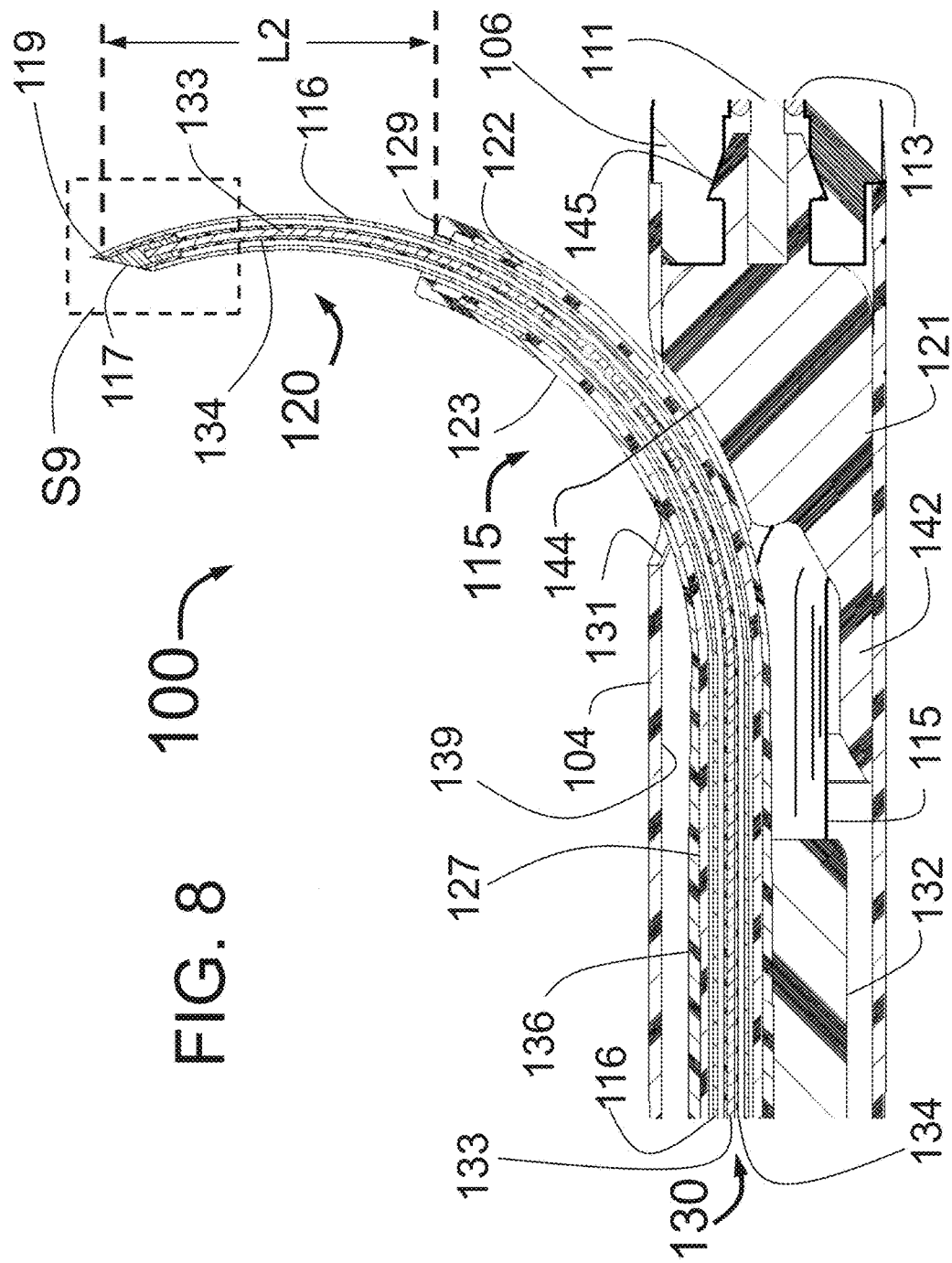
FIG. 8 is an enlargement of region S8 of the NSC of FIG. 2.
Figure 11:
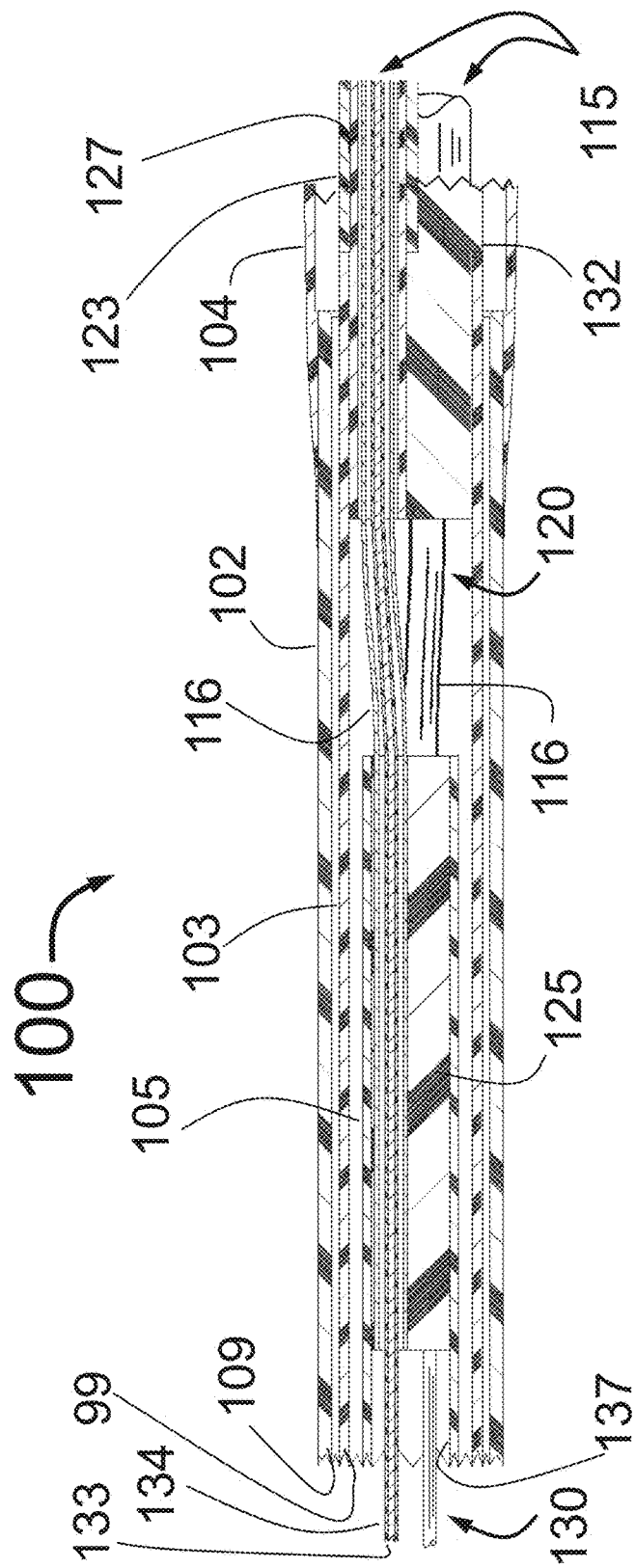
FIG. 11 is an enlargement of region S11 of the NSC of FIG. 7.

FIG. 7 is a longitudinal cross-section of a distal portion of the NSC 100 as shown in FIG. 6. The proximal end of FIG. 7 shows the three concentric tubes, the outer tube 102, middle tube 103 and inner tube 105 which form the central portion of the NSC 100. The outer tube 102 is attached to the outer tube extension 104 which is in turn attached to the tapered section 106. The fixed guide wire 110 with core wire 111 and outer layer 113 extends distally from the distal end of the tapered section 106. It should be noted that only part of the length of the guide wire 110 is shown in FIG. 7, its full length is shown in FIG. 6. Enlargements of the sections S8 and S11 of FIG. 7 are shown in FIGS. 8 and 11 respectively. The conduits 120 have outer sensor tubes 116, distal needles 119 and distal sensor electrodes 117.

FIG. 7 shows the guide tube 115 with radiopaque marker 122 in its fully advanced position placed through the opening 131 in the outer tube extension 104. The interior surface of the outer tube extension 104 forms part of the tubular shaft 139 should be made from a stiff material such as a metal or high durometer plastic so that it will be relative rigid as the guide tubes 115 are advanced and retracted.

Figure 15:
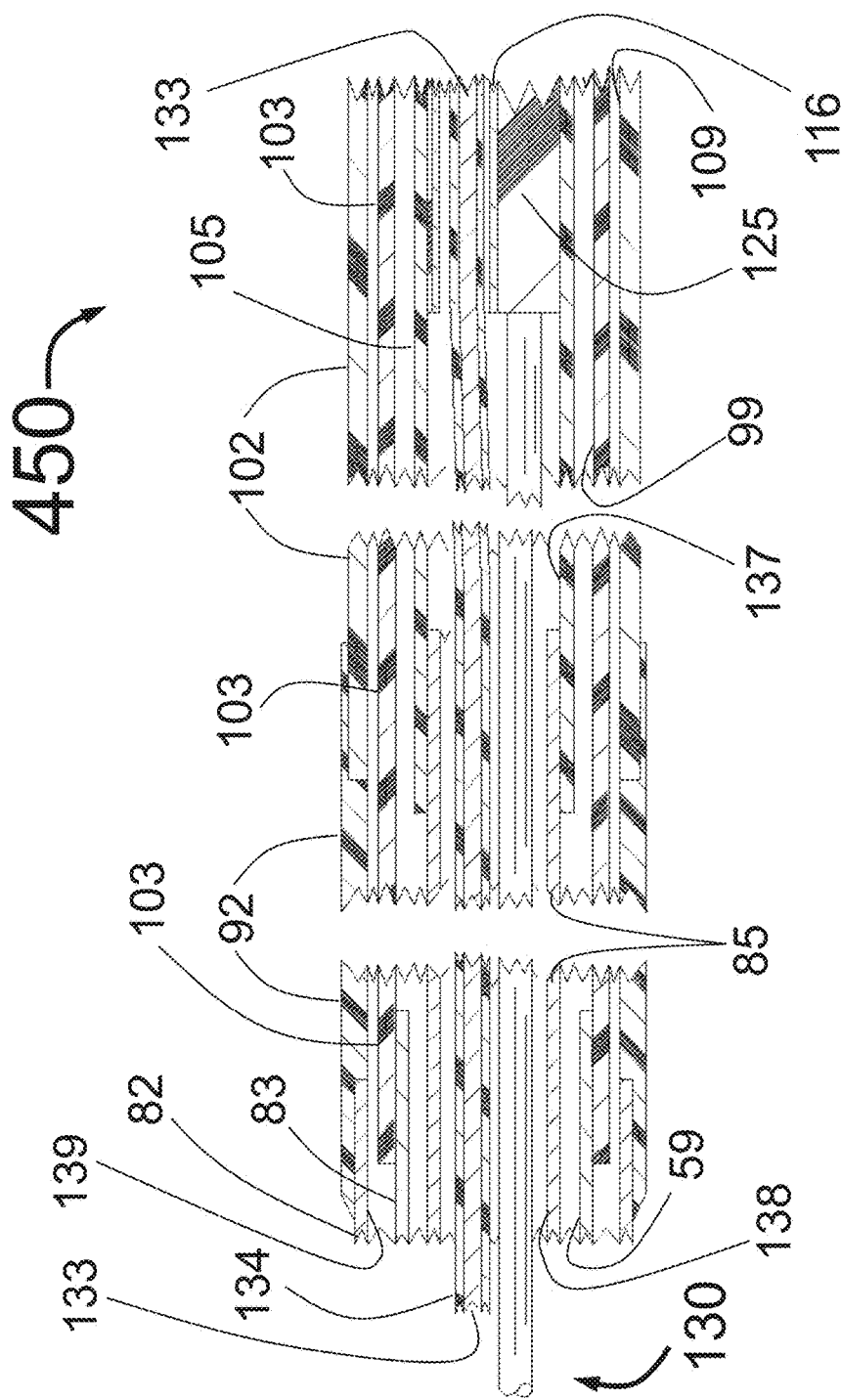
FIG. 15 is a longitudinal cross-section of the central portion of the NSC/PNASC showing the three proximal hypotubes.

While the inner tube 105, middle tube 103 and outer tube 102 could extend proximally to the proximal handle 300 of FIG. 16, an alternative embodiment of the central portion of the NSC is shown in detail in FIG. 15.

The central buttress 121 shown in FIG. 7 supports the guide tube 115 both as it is pushed distally, and after it is fully deployed. This central buttress 121 also provides radial support for the guide tubes 115 after they are advanced against the interior wall of the target vessel. This prevents the guide tubes 115 from backing away from the interior wall of the target vessel as the conduits 120 are advanced through the guide tubes 115 penetrating the vessel wall then forward to their desired position such as 2-6 mm beyond the interior surface of the wall of the target vessel. In some cases, the injection needles 119 at the distal ends of the conduits 120 might be advanced as deep as, for example, 10 mm beyond the interior surface of the target vessel. Additional lateral support for the guide tubes 115 is provided by the sides of the openings 131 that in combination with the central buttress 121 provide radial and circumferential/lateral support both during guide tube 115 advancement and outward expansions, and as backup during delivery of the needles 119 through the interior wall of the target vessel. The buttress may comprise a deflection surface such as a curved or linear ramp, which may in a curved embodiment correspond to the radius of curvature of the distal surface of the guide tube 115.

Preferably the radius of curvature of the distal portion of the conduits 120 have a central axis with the same, or nearly the same, radius of curvature as the central axis of the guide tubes 115 and of the central axis of the distal portion of the tubular shaft 139 that is formed within the central buttress 121 when measured in an unconstrained state. In addition, the length of the guide tubes 115 are preferably at least as long as the distal curved portion of the conduits 120 with distal needles 119. This would constrain the curved portion of each conduit 120 within the lumen of the guide tube 115 so that the conduit 120 cannot twist or change position.

As seen in FIG. 7 the inner tube 105 attaches through the plastic manifold 125 to the outer sensor tubes 116 of the conduits 120, thus the lumens of the sensor tubes 116 are in fluid communication with the lumen of the inner tube. This allows longitudinal movement of the inner tube 105 to advance and retract the conduits 120 coaxially through the guide tubes 115. The inner tube 105 and manifold 125 can slide along the longitudinal axis of the NSC 100 inside of the middle tube 103 which is shown with uniform diameter over its length including the portion coaxially outside of the manifold 125.

It is clear from the drawing of FIG. 7 that the manifold 125 is located within the lumen of the inner tube 105 in a portion of the tube 105 that is proximal to the distal end of the tube 105. The inner tube 105 and manifold 125 are both located coaxially within the outer tube 102 of the NSC 100 at a position proximal to the outer tube extension 104 which is the distal end section of the outer body of the NSC 100. This differs significantly from the embodiment shown in FIG. 3 of the Jacobson U.S. Pat. No. 6,302,870 where the manifold that connects the tube to the needles is attached to the distal end of the tube (instead of being inside it and proximal to the distal end).

The insulated wires 130 including a core wire 133 and insulation 134, as shown in FIG. 8, connect the sensor electrodes 117 to the proximal end of the NSC 100 where they exit near the proximal end as shown in FIG. 16. The wires 130 may there be connected to the external electronics located outside of the proximal end of the NSC 100. Different example configurations of the sensor electrodes 117 envisioned are shown in FIGS. 9, 10, 12, 13 and 14, which illustrate some preferred embodiments.

FIG. 8 is the enlargement of section S8 of the longitudinal cross-section of the NSC 100 as shown in FIG. 7. FIG. 8 shows the details of the guide tubes 115 with interior layer 123, outer layer 127, distal end 129 and radiopaque marker 122. Coaxially within the lumen of the guide tube 115 is the conduit 120 with sensor tube 116, distal sensing needle 119, sensor electrode 117 and insulted wire 130 with core wire 133 and insulation 134. Radiopacity of the distal end of the sensor tubes 116 with distal needles 119 can in some embodiments be important so that the operator can confirm under fluoroscopy that the needles 119 have properly deployed into the wall of the target vessel. The present embodiment uses the electrode 117 which would typically be formed from a dense and highly conducting metal such as gold or platinum to provide this radiopacity. It is envisioned however, that other embodiments of the present disclosure may use coatings, plating or markers on the outside and/or inside of the sensor tube 116 and needle 119 or the sensor tube 116 with distal needle 119 could be made from a two layer clad material.

The guide tubes 115 are advanced and retracted through the tubular shaft 139 with distal opening 131. The three guide tubes 115 are attached to each other near their proximal ends by the guide tube connector 132. FIG. 8 also clearly shows how the guide tube 115, when advanced against the central buttress 121 is forced outwardly and is supported by the curved ramp 144 of the central buttress 121 as well as the sides of the opening 131 of the tubular shaft 139. The central buttress 121 also has proximal fingers 142 that provide additional lateral support for the guide tubes 115.

The outer tube extension 104 connects at its distal end to the tapered section 106 which in turn lies coaxially around the guide wire 110 (of FIG. 6) with core wire 111 and outer layer 113.

Also shown in FIG. 8 is the penetration depth L2 which is the distance from the distal end 129 of the guide tube 115 to the distal tip of the sensor needle 119. Mechanisms at the proximal end of the NSC 100 (as shown in FIG. 16) control both the motion of the distal components such as the sensor tubes 116 and guide tubes 115 as well as to limit and/or adjust the penetration depth L2 of the needles 119.

It is envisioned that the central buttress 121 and distal openings 131 can, as shown in FIG. 8, be separate components of the NSC 100 or they can be formed as a single molded or machined part. The distal tip 145 of the central buttress 121 provides the attachment to secure the buttress 121 to the tapered section 106. Additionally, 121,131, and 106 could be a single molded or machined component.

While the preferred embodiment of the NSC 100 has the guide tubes 115 with a pre-formed curved shape, flexible naturally straight guide tubes are also envisioned where the buttress 121 forces the straight guide tubes to curve outward against the interior wall of the target vessel.

The term "central buttress" as used herein includes the, ramp 144 or other deflection surface that provides radial and some lateral support for the deployed guide tubes 115. Specifically, the curved ramp 144 of the buttress 121 supports and guides the outward motion of the guide tubes 115 as they exit though the distal openings 131 and also provide radial support for the guide tubes 115 and injection tubes, as they engage the interior wall of the target vessel. Additional lateral support is provided by the fingers 142 of the central buttress 121 as well as the tubular shaft 139 and the sides of the opening 131. A schematic view of such a central buttress is shown in FIG. 17 of Fischell et al U.S. Pat. No. 8,740,849.

While the central buttress shown in FIG. 8 is a plastic part, a radiopaque metal part, such as stainless steel, or a plastic material that includes radiopaque filler such as tungsten could be advantageously employed for showing the exact location where the guide tubes 115 will exit the NSC 100. It is also envisioned that a radiopaque marker could be placed or attached to a portion of the openings 131 or buttress 121 or outer tube extension 104 to show the likely spot where the guide tubes 115 and thus the needles 119 would engage the interior wall of the target vessel.

Many of the components of the NSC 100 are typically made from plastic materials such as polyamide, polyurethane, nylon or tecothane. These include the outer tube 102, middle tube 103 and inner tube 105, the outer tube extension 104, inner layer 127 and outer layer 123 of the guide tubes 115, the tapered section 106, the buttress 121, the guide tube connector 132 and the manifold 125. The manifold 125 can be a molded part or be epoxy or another resin that is injected to glue the sensor tubes together within the lumen of the inner tube 105.

It is also envisioned that any or all of the inner tube 105, middle tube 103 or outer tube 102 could also be a metal hypotube or a metal reinforced plastic tube.

The sensor tubes 116 would typically be made of a springy or shape memory metal such as nitinol. The guide tube radiopaque marker 122 would be made of a radiopaque material such as gold, platinum or tantalum or an alloy of these or similar metals. Any or certain portions of the outside of the NSC 100 could be lubricity coated to provide improved performance. The sensor tubes 116 and needles 119 should typically be smaller than 0.5 mm in diameter and preferably less than 0.3 mm in diameter to avoid any blood loss or leakage as the needles penetrate into the wall of the target vessel and are then removed.

FIG. 9 is a longitudinal cross section showing an enlargement of section S9 of FIG. 8 detailing the distal portion of the conduit 120 with sharpened needle 119 at the distal end of the sensor tube 116. Attached inside of the distal portion of the sensor tube 116 is the electrode 117 with insulation 139 that prevents the electrode 117 from coming into electrical contact with the metal sensor tube 116 in order to keep the two components from shorting out. The insulation 139 may also be configured to extent over the outside of the distal portion of the sensor tube 116 to reduce the potential for shorting further. The configuration shown in FIG. 9 would allow the electrodes 117 to be used for sensing and/or stimulation as a dipole referenced to the sensor tube 116 or a monopole referenced to another of the 3 conduits or a separate reference on another portion of the catheter or within the body or on the skin of the patient. The insulated wire 130 with core wire 133 and insulation 134 is attached to the electrode 117 as shown with a distal portion of the core wire 133 fixedly attached to the electrode 117. This can be done using any of a number of mechanical or other techniques including welding, brazing and crimping. Thus voltages sensed by the electrode 117 will be transmitted by the conduits 120 to the proximal end of the NSC 100 where external equipment 500 of FIG. 21 can measure and analyze these signals to provide information relating to nerve activity (e.g., sympathetic nerve activity), or the lack thereof, to the user. When used either for ablation or to provide stimulation of the nerve that may be related to the sensing paradigm (e.g., assessing ablation using evoked activity), then the external equipment may also send electrical signals to the core wire 133. In this embodiment with 3 bipolar sensors, sensing evoked nerve activity can be accomplished by using two electrodes on different conduits (or an electrode 117 and sensor tube 116) for stimulation and the other electrode 117 on the third conduit for sensing (the sensing would typically occur after the stimulation is provided). In another embodiment, sensing, stimulation, or ablation can be provided using any of the electrodes 117 by selecting the circuitry of the electronics 500 that is attached to the sensor/stimulator at the proximal site of the catheter system.

One technique for manufacturing the sensing tip configuration of FIG. 9 is to adhesively attach a cylindrical electrode 117 with insulation inside the distal end of a cylindrical sensor tube 116. Allow the adhesive to fix and then cut or grind the distal end of the sensor tube 116 with electrode 117 until the sharpened shape seen in FIG. 9 is produced. Alternatively, one could assemble the parts already sharpened as seen in FIG. 9.

It is also envisioned that the electrode 117 could be substituted by a thermocouple or thermistor with the objective of using the NSC as a temperature sensor to know the periadventitial temperature during an energy or cryo based ablation procedure. This temperature sensing could be used to guide the operation of a secondary device or could be used to guide operation of the PNASC itself. It is also envisioned that a thermocouple or thermistor may be attached to the guide tubes 115 and could be used for measuring the temperature of the intimal tissue using the external electronic equipment 500 to ensure that the temperature from energy based ablation does not overheat the media and intima of the artery.

FIG. 10 is a transverse cross section of the distal portion of the sensor tube 116 at 10-10 of FIG. 9. Shown are the sensor tube 116, the insulation 139, electrode 117 and core wire 133.

FIG. 11 is the enlargement of section S11 of FIG. 7 showing a preferred embodiment of the transition from the central portion to the distal portion of the NSC 100 including the outer tube 102, middle tube 103 and inner tube 105 with lumen 137. Also shown is the connection between the outer tube 102 and the outer tube extension 104. While the manifold 125 in FIG. 11 shows the proximal end of the sensor tubes 116 at a position distal to the proximal end of the manifold 125, it may be preferable to manufacture the NSC 100 with the proximal end of the sensor tube 116 located at or proximal to the proximal end of the manifold 125.

The guide tube connector 132 connects the three guide tubes 115 to the middle tube 103 that provides the impetus for advancement and retraction of the three guide tubes 115 of which two are visible in this view. The motion of the middle tube 103 is produced by the motion of control mechanisms at the proximal end of the NSC 100. The manifold 125 lies inside of the distal portion of the inner tube 105 and connects together the three sensor tubes 116 so that advancement and retraction of the inner tube 105 provides simultaneous advancement and retraction of the sensor tubes 116. Also shown in FIG. 11 are the flushing spaces between the several tubes. Specifically shown is the outer annular space 109 between the middle tube 103 and the outer tube 102 and the inner annular space 99 between the inner tube 105 and the middle tube 103. In typical use, each of these spaces 109 and 99 are to be flushed through with normal saline solution prior to insertion of the NSC 100 into the patient's body.

FIG. 11 also shows that the proximal end of the sensor tube 116 is in fluid communication with the lumen 137 of the inner tube 105. This can in some embodiments be important when the conduit distal portion includes an opening for delivering an ablative fluid to the perivascular tissue for chemical tissue ablation such as shown in FIG. 13 for the embodiment of a Perivascular Nerve Ablation and Sensing Catheter (PNASC) 200 with openings in the distal portion of a conduit.

The embodiment of the PNASC 100 of FIGS. 6 through 11 when connected to appropriate external equipment 500 of FIG. 21 can provide electrical stimulation and sensing and may also, be used for energy based tissue ablation as a perivascular Nerve Ablation and Sensing Catheter (PNASC) when sufficient energy is delivered through the wires 130 and electrodes 117.

Returning to FIG. 11, the wires 130 (for sensing/stimulation/ablation) with core wires 133 and outer insulation 134 run coaxially within the lumens of the sensor tubes 116 extend proximally from the proximal end of the sensor tube 116 within the lumen of the inner tube 105 all the way to the proximal end of the NSC 100 where they exit as the wires 361, 362 and 363 and terminate in the connector 360 of FIG. 16 that allows the wires 130 to connect to external electronics 500 shown in FIG. 21 for measurement of nerve activity and/or for providing stimulation signals to achieve stimulation and/or ablation. Although in the example configuration that is shown there are three wires 130 each of which terminate in a different electrode 117 of FIG. 9. In this configuration with only three wires, the NSC would act as a monopolar device with each electrode referenced to another electrode or an independent reference electrode.

In other embodiments a single wire may conduct electricity to two or more electrodes 117 which have an electrical bridging means incorporated into the catheter design in order to decrease the number of wires 130 that are carried along the length of the catheter. In this alternative embodiment, the same signal is provided to two or more electrodes 117 by a single wire 130.

It is also envisioned that a fourth reference wire could be added that can be bridged to the three sensor tubes 116 to act as the reference for the bipolar electrodes 117. It is still further envisioned that separate reference wires could be run to each of the three sensor tubes with six wires now running to the length of the catheter providing fully independent bipolar sensing from each of the three electrodes 117 referenced to their own sensor tube 116.

Longitudinal motion of the inner tube 105 within the uniform diameter middle tube 103 causes the manifold 125 and attached sensor tubes 116 to also move longitudinally. This longitudinal motion caused by control mechanisms near the proximal end of the NSC 100 will advance and retract the sensor tubes 116 through the lumens of the guide tubes 115 to expand outwardly to penetrate the inner wall of the target vessel to position the sensing/stimulation electrodes 117 of FIGS. 6 through 10 at a desirable perivascular location. For renal denervation applications, this would position the electrodes to sense activity as well as stimulate and/or electrically ablate the sympathetic nerves that lie outside of the renal artery.

FIG. 11 also shows how the three sensor tubes 116 extend from the distal end of the inner tube 105 and manifold 125 and then enter the lumen of the inner layer 127 of the guide tube 115 at the proximal end of the guide tube 115. The guide tubes 115 and guide tube connector 132 are attached coaxially within the distal section of the middle tube 103. Thus longitudinal motion of the middle tube 103 will cause longitudinal motion of the guide tube connector 132 and guide tubes 115 thus allowing the mechanism at the proximal section of the NSC 100 to advance and retract the guide tubes 115 with respect to the outer tube 102 and outer tube extension 104.

It is also envisioned that the penetration depth limitation could be realized by a limiting mechanism that limits the forward motion of the distal end of the inner tube 105 with respect to the guide tube connector 132. For example, a ring or other structure situated between the distal end of the inner tube 105 or manifold 125 and the proximal end of the guide tube connector 132 would limit the forward (distal) motion of the distal end of the inner tube 105 and thus limit penetration of the needles 119 beyond the distal ends 129 of the guide tubes 115. Such a structure could be unattached, or attached to an internal structure of the NSC 100 shown in FIG. 11 such as the inner tube 105, manifold 125, sensor tubes 116, guide tube connector 132, proximal ends of the guide tubes or the middle tube 103. Such a structure could also have a length adjustment such as screw threads that would allow it to be used to calibrate the penetration depth of the needles 119 beyond the distal ends 129 of the guide tubes 115.

FIG. 12 shows an alternative embodiment of the NSC 100 of FIGS. 7 and 8, labelled 100', with the distal portion of a conduit 150. Except for the conduit 150, the remainder of the NAC 100' is identical to the NSC 100 of FIGS. 6, 7, 8 and 11. In this embodiment the electrode 154 with sharpened needle tip 159 is attached within the distal end of a cylindrical sensor tube 152 with insulation 159 to prevent electrical contact between the electrode 154 and the sensor tube 152. The distal end of the electrode 154 can be pre-sharpened or it could be sharpened by cutting or grinding following attachment into the distal end of the sensor tube 152. This configuration has advantage over the tip of FIG. 9 as it provides an electrode with significantly more surface area for sensing nerve activity voltage signals (and for providing stimulation or ablation when the external electronics are configured to provide such functionality). It also provides a greater distance between the electrode 154 and sensor tube 152 for use as a bipolar electrode. The same wire 130 with core wire 133 and insulation 134 as shown in FIGS. 7 through 11 is attached to the electrode 154.

FIG. 13 is an embodiment of the distal portion of the conduit 160 of the PNASC 200 integrated ablation and nerve sensing catheter. Except for the conduit 160, the remainder of the PNASC 200 is identical to the NSC 100 of FIGS. 6, 7, 8 and 11. The tip 160 differs from the tip 150 of FIG. 12 in that side holes 165A and 165B have been placed into the sides of the sensor tube 162 to allow ablative fluid injected at the proximal end of the PNASC 200 to flow through the lumen 137 of the inner tube 105 of FIG. 11 into the lumens 167 of the sensor/injection tubes 162 and then out of side holes 165A and 165B into the tissue of the media, adventitia or periadventitial space depending on the depth of penetration of the needles 169. In this embodiment, the electrode 164 with needle tip 169 and insulation 159 are identical to that of the electrode 154 and insulation 159 of the conduit 150 of FIG. 12. The sensor wire 130 is also the same as in FIG. 12 with core wire 133 and insulation 134.

The conduits 120, 150 and 160 of the NSC 100 and PNASC 200 devices would preferably be very small gauge (smaller than 25 gauge) to prevent blood loss following penetration and removal through the vessel wall. Also the PNASC 200 which includes a distal opening in one or more of the conduits 160 to provide egress for the ablative fluid, as shown in FIG. 13 typically has a non-coring (cutting) needle 169. The PNASC 200 would also preferably have at least 2 conduits 160 with distal electrodes 164, but 3 to 8 tubes with distal needles may be more appropriate, depending on the diameter of the vessel to be treated and the ability of the injected ablative fluid to spread within the perivascular space. For example, in a 5-7 mm diameter renal artery, 3 conduits 160 should be utilized if ethanol is the ablative fluid.

A PNASC 200 integrated ablation and sensing system may provide large advantages over other current technologies for applications in addition to renal denervation. For example, the PNASC 200 can provide a highly efficient, and reproducible perivascular circumferential ablation of the muscle fibers and conductive tissue in the wall of the pulmonary veins near or at their ostium into the left atrium of the heart to treat atrial fibrillation (AF). Additionally, this system could benefit denervation of the pulmonary arteries in the case of nerve ablation to treat pulmonary arterial hypertension. For the AF application, operating the catheter system to obtain nerve and/or cardiac myocyte electrical activity measurements could be an effective technique to provide immediate assessment of the success of an AF ablation procedure during the actual procedure. Other potential applications of this approach, such as pulmonary artery nerve ablation, or others, may also become evident from the various teachings of this patent specification.

The embodiments shown in FIGS. 12 and 13 could also be adapted to deliver ultrasonic energy to with an ultrasonic transducer replacing the electrodes 154 and 164 with the voltage to activate the transducer provided between the core wire 133 and the electrodes 154 and 164 and the removal of the insulation layer 159.

Figure 14:
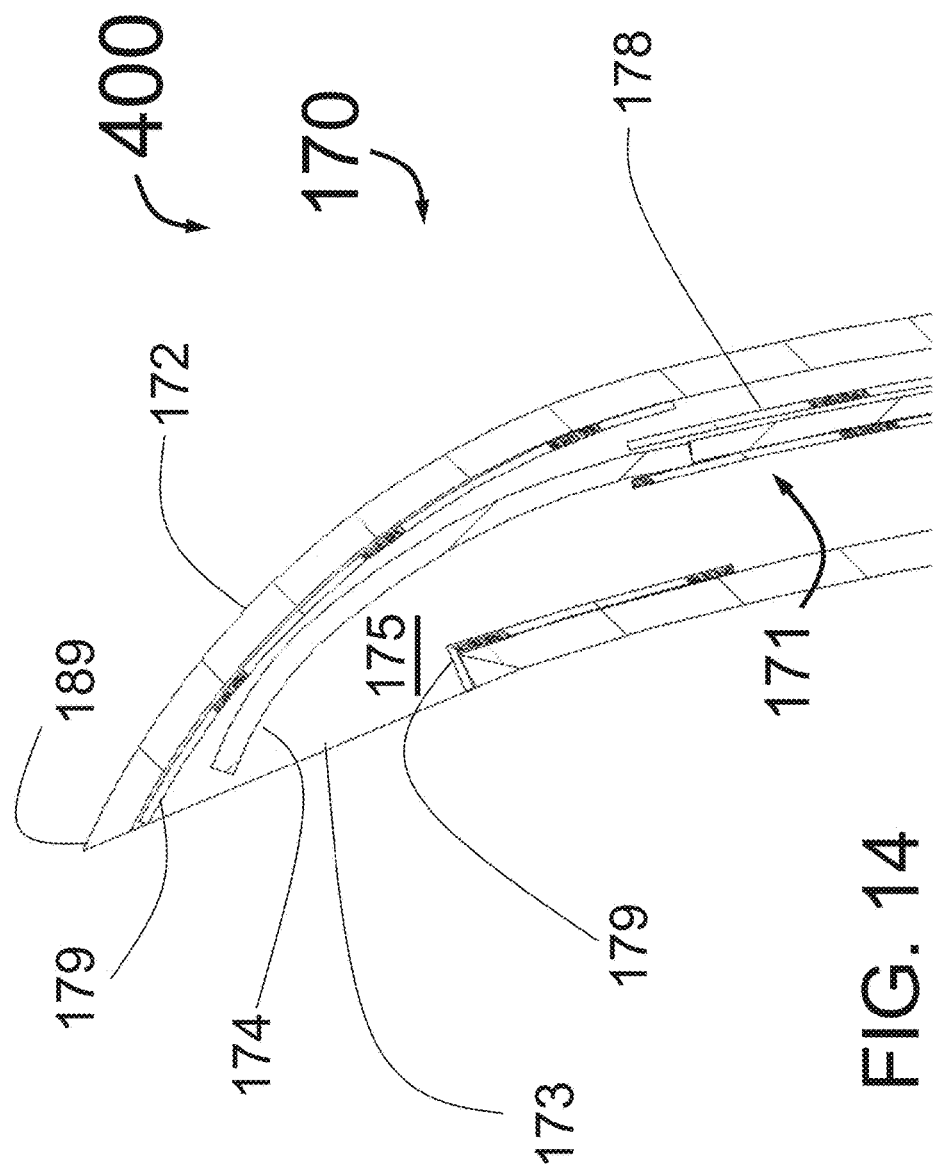
FIG. 14 is a longitudinal cross section of yet another embodiment of the distal portion of the PNASC of FIG. 8 that would replace the embodiment of the distal needles shown in FIG. 9.

FIG. 14 is another embodiment of the distal portion of the conduit 170 of the PNASC 400 which can both inject ablative fluid and sense nerve activity. Except for the distal portion of the conduit 170, the remainder of the PNASC 400 can be identical to the NSC 100 of FIGS. 6, 7, 8 and 11. This embodiment uses a non-coring Huber type needle configuration with sharpened needle tip 189 with a turn in the distal end of the sensor/injector tube 172 to prevent coring during penetration. A radiopaque wire 171 with core wire 174 and insulation 178 connects proximally to external equipment replacing the wires 130 of FIGS. 7 through 11. The distal portion of the wire 171 has the insulation removed to allow for the sensing of nerve voltages. To make this work it is necessary to insulate the sensor wire 172 except for the distal portion and also the proximal side where it connects to the external equipment shown in FIG. 21 and also insulate the inside of the distal portion 170 of the PNASC 400 to prevent electrical shorting between the sensor/injection tube 172 and the core wire 174. The core wire 174 would typically be made from gold or platinum or an alloy of gold or platinum. It is also envisioned that only the distal portion of the wire 171 would be radiopaque with the more proximal portion being a standard wire material such as copper.

FIG. 15 is a the longitudinal cross-sections of three portions of the central section of the catheter 450 that can be integrated into the NSC 100, PNASC 200 and PNASC 400 of FIGS. 6 through 14. At the proximal end of the proximal portion of the catheter 450 are three concentric metal hypotubes, an outer hypotube 82, middle hypotube 83 and inner hypotube 85. These are typically made from thin walled metallic tubing such as stainless steel, L605, cobalt chromium or nitinol. The outer hypotube 82 attaches at its distal end to a proximal plastic outer tube 92 typically made from a relatively high durometer plastic, for example polyimide. As seen in the central cross-section of FIG. 15, the proximal plastic tube 92 attaches at its distal end to the proximal end of the outer tube 102 also shown in FIGS. 6 through 8. The outer tube 102 is typically made from a lower durometer/more flexible plastic than the proximal plastic tube 92.

As shown in the proximal section of FIG. 15, the middle hypotube 83 is attached at its distal end to the middle tube 103. As shown in the central section of FIG. 15 the inner hypotube 85 is attached at its distal end to the proximal end of the inner tube 105.

Also shown in distal section of FIG. 15 is the manifold 125 that connects the inner tube 105 to the sensor tube 116 as also shown in FIG. 11. Thus the wires 130 with core wire 133 and insulation 134 exit the proximal end of the sensor tubes 116 and continue in the proximal direction through the inner tube 105 and then proximally to that through the lumen 133 of the inner hypotube 85.

For the embodiment where the catheter 450 is utilized to inject a fluid into the perivascular space, the lumen 138 of the inner hypotube 85 is in fluid communication with the lumen 137 of the inner tube 105 which is in fluid communication with the lumens of the sensor tubes 116 of FIGS. 6-11, or the sensor tubes 152, 162 or 172 of FIGS. 12, 13 and 14 respectively. The 162 and 172 being for the PNASC 200 and 400 where injection of an ablative fluid moves from the injection port 354 in the handle 300 of the catheter and through the inner hypotube 85 into the inner tube 105 through the tubes 162 or 172 and into the perivascular space through openings in the distal portions of the tubes 162 or 172. The inner hypotube 85 runs longitudinally to the fluid port or connector at the proximal end of the catheter 450 to allow injection of fluids.

While it is envisioned that the outer tube 102, middle tube 103 and inner tube 105 could run all the way to the proximal end of the NSC 100 or PNASC 200 or 400, the configuration of FIG. 15 is the preferred embodiment as it provides flexibility where needed near the distal end of the catheter with better control of the motion of the inner and middle tubes 105 and 103 as the metal hypotubes do not compress as they move longitudinally while plastic may.

FIG. 16 is a schematic view of one embodiment of the proximal portion (handle) 300 of the NSC 10, NSC 100 or PNASC 200 or PNASC 400. The terms proximal portion 300 and handle 300 will be used interchangeably here. The handle 300 includes the mechanisms for advancing and retracting the needle guiding elements/guide tubes 30/115 and sensor/injector tubes 22/116 with distal needles 24/119 during the procedure to position the electrodes 117, 154, 164 and 174 of the various embodiments of the NSC 10, 100, PNASC 200 and PNASC 400 within the perivascular space. Similarly the handle 300 will do the same to position the distal tips of the conduits 20 of the SNASC 10 of FIGS. 1 through 5 and PNASC 200 of FIG. 13 in the perivascular space. Such positioning allows for sensing, stimulation and energy based ablation of sympathetic nerve activity as well as injection of ablative fluid for the PNASC 200 and 400 embodiments of FIGS. 13 and 14.

The handle 300 also has locking mechanisms activated by first and second control mechanisms such as press-able buttons 332 and 342. Specifically, button 332 when depressed unlocks the motion of the guide tube control cylinder 333 with respect to the outer tube control cylinder 335. The outer tube cylinder 335 is attached to the outer hypotube 82 which is in turn connected to the tube 92 that connects to the outer tube 102 as seen in FIG. 15 or the outer tube 13 of FIG. 5. The transition section 338 provides strain relief to avoid kinks at the connection between the outer tube control cylinder 335 and the outer hypotube 82.

The guide tube control cylinder 333 is attached to the middle hypotube 83 that in as shown in FIGS. 5 and 15, connects to the middle tube 12 of the NSC 10 of FIGS. 1-4 or the middle tube 103 of FIGS. 6-8 that in turn is connected to the guide tubes 30 of FIGS. 1-4 or guide tubes 115 of FIGS. 6 through 8. The guide tube control mechanism 330 allows the user of the NSC/PNASC to control the distal and proximal motion of the guide tubes 30 or 115 with respect to the outer tube 82 and includes the button 332 and the guide tube control cylinder 333. The needle control mechanism 340 allows the user of the NSC/PNASC to control the distal and proximal motion of the conduits 20 of the NSC 100 of FIGS. 1-5 or the conduits 120 of the NSC 100 of FIGS. 6-8. The needle control mechanism includes the button 342 and the needle control cylinder 345.

The button 342 when depressed, unlocks the motion of the needle control cylinder 345 with respect to the guide tube control cylinder 333. The needle control cylinder is attached to the inner hypotube 85 of FIG. 15. Moving the needle control cylinder 343 with respect to the guide tube control cylinder 333 will move the inner hypotube 85 which in turn will cause the relative longitudinal motion of the inner tube 105 of FIGS. 6-8 with respect to the middle tube 103 of FIGS. 6 through 8 which causes the advancement and retraction of the sensor tubes 116 with distal needles 119 though the guide tubes 115. This mechanism advances and retracts the conduits 120 with distal electrodes 117 of FIGS. 6-10, as well as the electrodes 154, 164 and 174 of the distal tips shown in FIGS. 12, 13 and 14. Similarly this mechanism would advance and retract the conduits 20 of FIGS. 1-5 by the controlling the relative motion of the inner tube 11 with respect to the middle tube 12.

The handle 300 shown in FIG. 16 has the flushing port 344. Port 344, which would typically have a Luer fitting, is shown with a cap 346. Port 344 is used to flush with saline the annular spaces 139 and 59 as shown in FIG. 15 and in turn will flush the lumens 109 and 99 shown in FIGS. 11 and 15. The injection port 354 which typically has an ablative fluid connector fitting is shown with cap 356. For the PNASC 200 or 400 embodiments, port 354 allows injection of ablative fluid into the lumen 138 of the inner hypotube of FIG. 15 which then will flow into the inner tube 105 and then into the sensor tubes 162 of the conduit 160 of the PNASC 200 of FIG. 13 and the sensor tube 172 of the conduit 170 of the PNASC 400 of FIG. 14. The tubes 162 and 172 have openings near or at their distal end to allow flow of the ablative fluid into the perivascular space.

Although FIG. 16 shows one flushing port 344, it envisioned that two or more flushing ports could be used to flush the internal spaces (other than the injection lumen) within the various embodiments of the NSC and PNASC. It is also envisioned that a single button and cylinder mechanism could replace the two buttons 332 and 342. If this is the case, then a telescoping mechanism, internal to the proximal portion of the handle 300 would, upon advancement of the single button, first advance the guide tubes 115 then advance the conduits 120 with distal electrodes 117. Retraction of the single button would first retract the conduits 120 and then retract the guide tubes 115.

While a standard Luer or Luer lock fitting could be used for the ablative fluid connector fitting for the injection port 354, Fischell et al. in U.S. Pat. No. 8,740,849 describes a non-standard fitting that would be advantageous for injection of the ablative fluid. Because of the ablative/toxic nature of the ablative fluid, having a non-standard fitting for the port 354 would reduce the chance of accidentally injecting the ablative fluid into one of the other ports (e.g. 344) or into the standard Luer fitting in the "Y" adapter typically used with a renal guiding catheter. It would also prevent the operator from the potential error of injecting flushing solution or other agents contained in a conventional Luer lock syringe, through the lumen of the injection tubes. It would also be an advantage for the non-standard fitting port 354 to have a smaller lumen than a standard Luer fitting so as to minimize the catheter dead space/internal volume.

The handle 300 also includes a gap adjustment cylinder 348 that when rotated in one direction reduces the penetration depth L1 of FIG. 3 or L2 shown in FIG. 8 which is the distance the needle tip 23 or needles 119 extend beyond the distal ends 34 and 129 of the guide tubes 30 and 115. Rotation in the other direction of the cylinder 348 will increase the penetration depth L1 or L2. It is envisioned that the gap adjustment cylinder 348 could be accessible to the user of the handle 300 with markings on the handle 300 to indicate the distance that will be achieved. This has advantages for use with the NSC 100 which is a purely diagnostic catheter so that the depth of electrode placement can be set and then adjusted of more than one depth is desired. A handle that uses a gap to limit needle penetration depth is disclosed in U.S. Pat. Nos. 8,740,849 and 9,056,185, which are incorporated by reference in their entireties.

In another embodiment of the handle 300, the gap adjustment cylinder 348 could be accessible only during assembly and testing of the handle 300 at the factory. This fabrication method is designed to ensure a properly calibrated penetration depth L1/L2 that is preset in the factory during manufacturing and testing of each NSC 10/100 or PNASC 200/400. This ability to calibrate the penetration depth L1/L2 is useful to achieving a good yield during manufacturing. In other words, even with variation of a few millimeters in the relative lengths of the components of the NSC 10/100 or PNASC 200/400 such as the inner tube 105 and middle tube 103 of the NSC 100, the distance L1/L2 can be dialed in exactly using the gap adjustment cylinder 348. In this preferred embodiment, the NSC 10/100 or PNASC 200/400 would be labeled according to the penetration depth L1/L2. For example, the NSC 100 might be configured to have three different depths L2 of 3 mm, 4 mm and 5 mm. It is also envisioned that a set screw or other mechanism (not shown) could be included to lock the gap adjustment cylinder 348 at the desired penetration depth setting after calibration. While a gap adjustment cylinder 348 is shown here, it is envisioned that other mechanisms such as a sliding cylinder could also be used to adjust the depth L1/L2.

The wires 130 of FIGS. 6 through 13 and the wires 171 of FIG. 14 exit through the side of the most distal portion of the handle 300 as seen in FIG. 16. These three wires 130 (more wires could be used if more electrodes/needles are used, or one-to-many electrical bridging could be implemented in the distal portion of the catheter in order to provide electrical communication to these additional electrodes without the bulk that would be associated with a larger set of individual wires) are connected to an electrical connector 360 which in turns connects to the electronics 500 of FIG. 21 where the voltages between pairs of wires 130 can be measured, processed, and displayed as sensed data measurements. In the embodiment of the NSC 10 or 100, where there is no fluid injection, the wires 130 may exit the proximal section of the handle 300 through the lumen of the fitting 354 where the cap 356 has been removed.

A primary function of the handle 300 is to operate the NSC 10/100 for measurement of the activity of the sympathetic nerves outside of the renal artery before, during and after a renal denervation procedure. With the integrated PNASC 200 or 400, the handle 300 also allows for injection of an ablative fluid to be delivered to the perivascular space. For example, the electrical signals communicated with the distal end of the catheter are transmitted along the wires 361, 362, and 363 which exit the handle 300 to communicate with the external electronic equipment 500 that provides, for example, sensing. Additionally, the hypotubes communicate fluid from the injection port 344 toward the distal tip.

Figure 18:
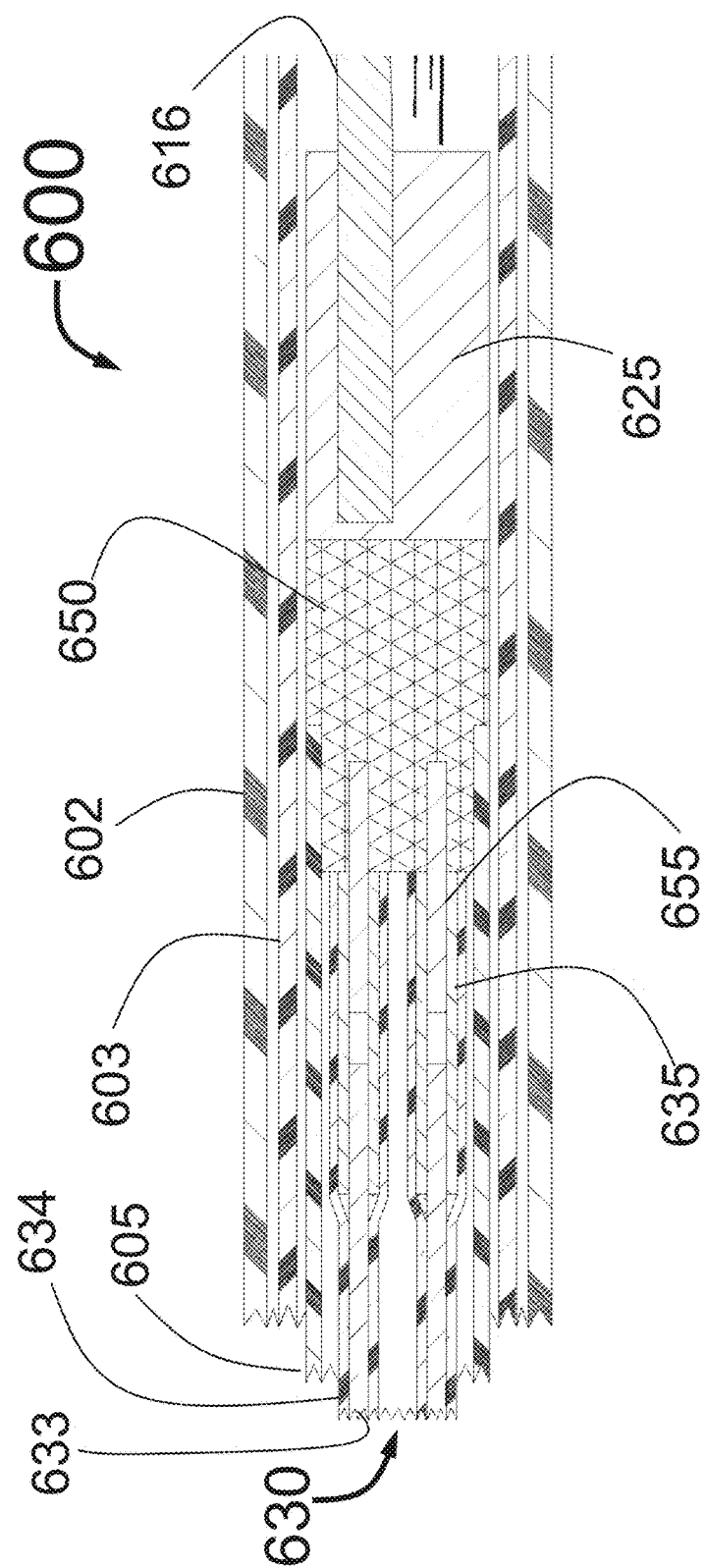
FIG. 18 is an enlargement of section S18 of FIG. 17.
Figure 19:
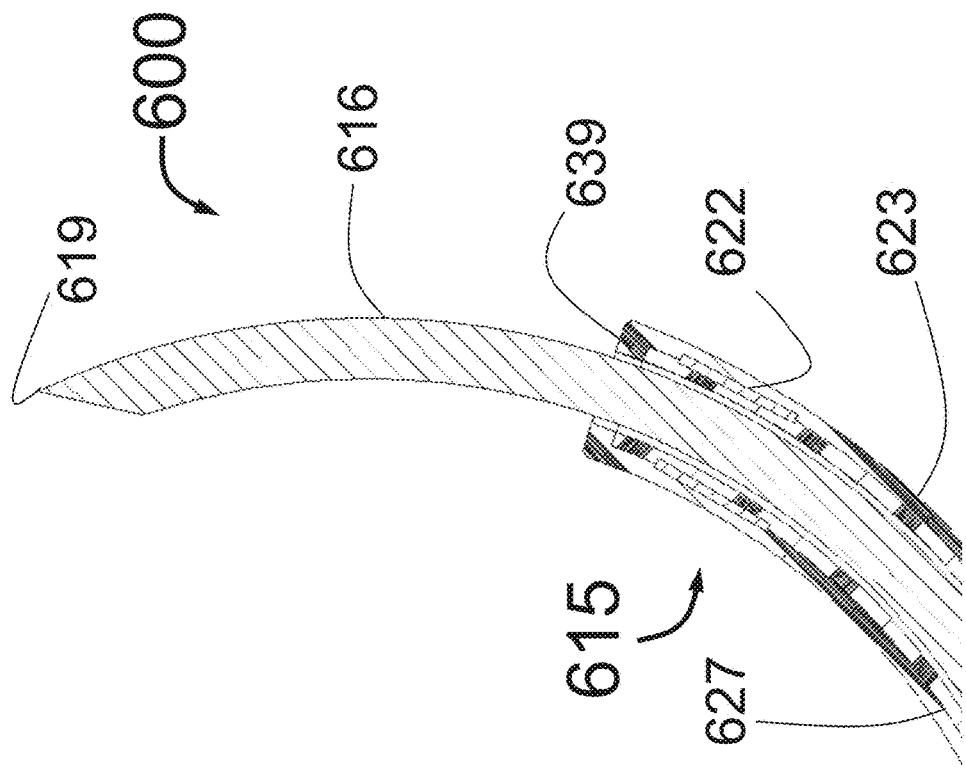
FIG. 19 is an enlargement of section S19 of FIG. 17.

FIG. 17 shows an alternative embodiment a longitudinal cross-section of a distal portion of an Ultrasound Nerve Ablation catheter (UNAC) 600. The primary structure of the UNAC 600 is similar to that of the NSC 100 of FIG. 7. The proximal end of FIG. 17 shows the three concentric tubes, the outer tube 602, middle tube 603 and inner tube 605 which form the central portion of the UNAC 600. The outer tube 602 is attached to the outer tube extension 604 which is in turn attached to the tapered section 606. The fixed guide wire 610 with core wire 611 and outer layer 613 extends distally from the distal end of the tapered section 606. It should be noted that only part of the length of the guide wire 610 is shown in FIG. 17, its full length is similar to that shown for the guide wire 110 of the NSC 100 in FIG. 6. Enlargements of the sections S18 and S19 of FIG. 17 are shown in FIGS. 18 and 19 respectively.

FIG. 17 shows the guide tube 615 with radiopaque marker 622 in its fully advanced position placed through the opening 631 in the outer tube extension 604. The interior surface of the outer tube extension 604 forms part of the tubular shaft 639 and can in some cases be made from a stiff material such as a metal or high durometer plastic so that it will be relatively rigid as the guide tubes 615 are advanced and retracted.

While the inner tube 605, middle tube 603 and outer tube 602 could extend proximally to a handle such as the proximal handle 300 of FIG. 16, the central portion of the UNAC can be constructed similar to that shown in the embodiment of the central portion of the NSC 100 of FIG. 15.

The UNAC 600 utilizes an ultrasound transducer 650 coupled by the coupler 625 to three distal wires 616 with sharpened needle distal tips 619. Thus, vibration from the transducer 650 is conducted to through the wires 616 into the perivascular tissue near the tips 619 of the wires 616. With sufficient intensity the vibration will cause ablation of the perivascular tissue. Perivascular delivery of energy by ultrasound for renal denervation can be advantageous in some cases over intravascular delivery as the pain nerves are in the media of the renal artery and the nerves to be ablated are in the perivascular space.

The central buttress 621 shown in FIG. 17 supports the guide tube 615 both as it is pushed distally, and after it is fully deployed. This central buttress 621 also provides radial support for the guide tubes 615 after they are advanced against the interior wall of the target vessel. This prevents the guide tubes 615 from backing away from the interior wall of the target vessel as the needles 619 are advanced through the guide tubes 615 penetrating the vessel wall then forward to their desired position 2-10 mm beyond the interior surface of the wall of the target vessel. Additional lateral support for the guide tubes 615 is provided by the sides of the openings 631 that in combination with the central buttress 621 provide radial and circumferential/ lateral support both during guide tube 615 advancement and outward expansions, and as backup during delivery of the needles 619 through the interior wall of the target vessel. The buttress may comprise a deflection surface such as a curved or linear ramp, which may in a curved embodiment correspond to the radius of curvature of the distal surface of the guide tube 615.

Preferably the radius of curvature of the distal portion of the wires 616 have a central axis with the same, or nearly the same, radius of curvature as the central axis of the guide tubes 615 and of the central axis of the distal portion of the tubular shaft 639 that is formed within the central buttress 621 when measured in an unconstrained state. In addition, the lengths of the guide tubes 615 are preferably at least as long as the distal curved portion of the wires 616 with distal needles 619. This would constrain the curved portion of each conduit 620 within the lumen of the guide tube 615 so that the wires 616 cannot twist or change position.

As seen in FIG. 17 the inner tube 605 attaches to the ultrasound transducer 650 that connects through the coupler 625 to the wires 616. This allows longitudinal movement of the inner tube 605 to advance and retract the wires 616 coaxially through the guide tubes 615. The inner tube 605, ultrasound transducer 650 and coupler 625 can slide along the longitudinal axis of the NSC 600 inside of the middle tube 603. Two insulated wires 630 provide power for the ultrasound transducer 650 from external equipment (not shown) beyond the proximal end of the UNAC 600.

FIG. 18 is the enlargement of section S18 of the longitudinal cross-section of the UNAC 600 as shown in FIG. 17. FIG. 18 shows the details of the ultrasound transducer 650 with connector pins 655 that connect through the wire connectors 635 to the inner conductors 633 of the wires 130. FIG. 18 also shows in detail how the inner tube 605 attaches to the outside of the ultrasonic transducer 650 that is attached to the coupler 625 that transmits the ultrasonic energy to the wires 616. Also shown is the middle tube 603.

FIG. 19 is a longitudinal cross section showing an enlargement of section S19 of FIG. 17 of the UNAC 600. FIG. 19 shows the detail of the distal portion of the guide tube 615 with distal end 639 and the wire 616 with sharpened distal needle 619. The guide tube 615 has radiopaque marker 622, outer layer 623 and inner layer 627. The radiopaque marker 622 is a band made from a radiopaque metal such as gold, platinum or tantalum. The guide tube 615 is similar in construction to the guide tube 115 of FIGS. 7 and 8. The wire 616 should either be made from a radiopaque metal or its distal portion could be plated or coated with a radiopaque material. It is also envisioned that the wire 616 could be a thin tube with a radiopaque wire through the center.

Figure 20A:
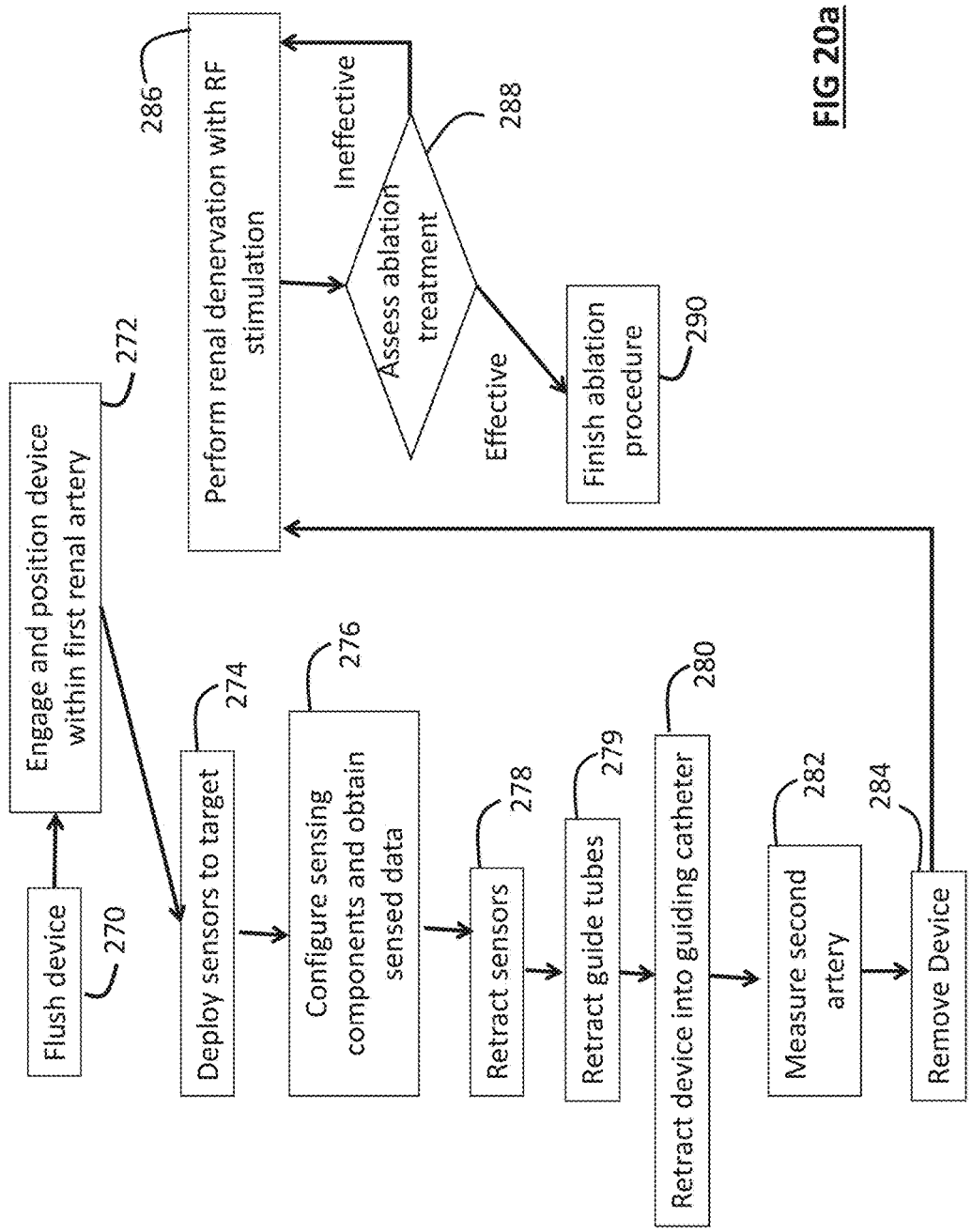
FIG. 20a is a schematic view of a method for using the PNASC.

FIG. 20a shows an embodiment of a procedure to first assess the perivascular nerve activity prior to a renal denervation procedure, then perform a renal denervation procedure followed by a post denervation assessment of nerve activity. For FIGS. 20a and 20b, the element numbers referenced in the 100s are shown in FIG. 8 and element number 82, and those in the 300s, are shown in FIG. 16.

As show in FIG. 20a, the procedure using the NSC 100 of FIGS. 6-11 would include the following steps although not every step is essential and steps may be, excluded, simplified or modified as will be appreciated by those of skill in this art. The distal portion element numbers will reference the NSC 100 of FIGS. 6 through 11 although they also apply to the other similar embodiments shown of the NSC 10 (FIGS. 1-5) and 100' (FIG. 12) as well as the PNASC 200 and 400 of FIGS. 13 and 14.

a1. The procedure begins by preparing the NSC 100 for insertion into a human body by flushing the device in step 270 which would typically include flushing all of the internal volumes of the NSC 100 with normal saline or another fluid through the ports 344 and 354 of the handle 300 of FIG. 16.

a2. Engage and position device within first renal artery in step 272 which by inserting the distal end of the NSC 100 through a previously placed guiding catheter with the guiding catheter distal end engaged into the ostium of the renal artery where it attaches to the aorta and positioning the distal portion of the NSC 100 as at the desired location in the renal artery.

a3. Deploy sensors to target in step 274 which may include depressing the button 332 (of FIG. 16), and while holding the outer tube control cylinder 335 which is locked to the guide tube control cylinder 333, push the guide tube control cylinder 335 in the distal direction advancing the guide tubes 115 until the distal end of the guide tubes 129 come into contact with the inside wall of the renal artery limiting the advance of the middle tube 103 of FIG. 8 and deploying the guide tubes 115 from inside the tubular shafts 120 and out through the openings 31. The notch 331 will otherwise stop the distal motion of the guide tube control cylinder 333 when it engages the tube 344 at the maximum allowable diameter for the guide tubes 115.

Still in step 274, releasing the button 332 which relocks the relative motion of the outer tube control cylinder 335 with respect to the guide tube control cylinder 333.

Still in step 274, depressing the button 342 that allows relative motion of the needle control cylinder 345 with respect to the guide tube control cylinder 333 and while holding the outer tube control cylinder 335 (which is now locked to the guide tube control cylinder 333) advance the needle control cylinder 345 with distal end 349 until the internal gap 347 is closed against the proximal end of the gap adjustment cylinder 348 inside the needle control cylinder 345 stopping the motion at the preset depth L2 for the needle tips 119 with respect to the distal ends 129 of the guide tubes 115.

Still in step 274, releasing the button 342, which relocks the motion of the needle control cylinder 345 to the guide tube control cylinder 333. This places the NSC 100 in a configuration where the needles 119 penetrate through the internal elastic lamina (IEL) of the renal artery and penetrate to a preset distance (typically between 2 to 8 mm) beyond the IEL into the perivascular space outside of the media of the renal artery.

a4. Configuring sensing components and obtaining sensed data in step 276 which may include attaching the connector 360 to the external nerve activity measurement equipment 500 of FIG. 21 and measuring the amplitude or level of sympathetic nerve activity between at least one pair of electrodes 117 of FIGS. 6-8.

Rather than measure the nerve activity between distal electrodes of the NSC 100, the nerve activity may be measured between individual electrodes 117 and a separate reference electrode with a conducting wire that is attached to the external equipment 500 of FIG. 21 and also to the patient. Such a separate wire/electrode may be part of the NSC system. As another example, a wire connected to the catheter surface or fixed guide wire 110 of FIG. 6 may be attached to the external electronic equipment 500. The wire could communicate from the catheter body to the electronic equipment by way of the connector 360 of FIG. 16. The separate reference wire with distal electrode could also be on the skin surface such as used for an electrocardiogram or percutaneously inserted into tissue within the patient. Finally, the separate reference could be a wire attached to a skin surface electrode. The level of nerve activity can be noted manually by the user and or might be saved in memory of the external equipment 500.

a5. Retract the sensors/electrodes in step 278 which by depressing the button 342 and while holding the outer tube control cylinder 335, pulling the needle control cylinder 345 back in the proximal direction until the needles 119 are fully retracted back into the guide tubes 115. It is envisioned that a click or stop would occur when the needle control cylinder 345 reaches the correct position so that the needles 119 are fully retracted. Then releasing the button 342 locking the motion of the injection needle control cylinder 345 to the guide tube control cylinder 333.

a6. Retract the guide tubes in step 279 by depressing the button 332 releasing the relative motion of the outer tube control cylinder 335 with respect to the guide tube control cylinder 333 and retracting the guide tubes 115 back into the tubular shafts 139 then releasing the button 332 locking the NSC 100 in its closed pre-deployment position.

a7. Retract the catheter system back in to the guiding catheter in step 280 and then reposition the distal end of the guiding catheter into the ostium of the second renal artery.

a8. Measure nerve activity outside of the second renal artery in step 282 by repeating steps a1 through a7. The measurement of nerve activity can include sensing at least one interval of nerve activity for a selected duration in order to obtain sensed data, processing the sensed data to obtain at least one baseline dataset which can include raw data and/or at least one summary statistic. The measurement of nerve activity can also include at least one of displaying and storing at least one baseline value related to the baseline dataset. The summary statistic related to the baseline dataset can include values such as mean, median, and standard deviation of a measure; variance, peak amplitude, average amplitude, peak frequency, average frequency, burst duration, guard-bands, and other measures as disclosed herein.

a9. In step 284 remove the entire NSC 100 and guiding catheter from the body.

a10. Perform a renal denervation in step 286 on one (unilateral) or both (bilateral) arteries using energy based devices such as the Simplicity™ catheter from Medtronic or the PTAC of Fischell et al U.S. Pat. No. 8,740,849 and then remove the treatment device from the body.

a11. Assess the efficacy of the renal denervation in step 288, by reinserting the NSC 100 through the guiding catheter and repeat steps a2 through a9. Using the difference in nerve activity between before and after the renal denervation procedure, assess the effectiveness of the renal derivation for each artery. Alternatively, when steps 270 to 284 are excluded, step 288 may simply entail measurement and assessment of post-ablation nerve activity such as comparing the sensed nerve activity to an appropriate population normative threshold value or otherwise appropriate determined quantitative or qualitative treatment criterion to determine if the treatment criterion was met or failed to be met.

12. If the denervation was not sufficiently effective (treatment criterion was not met), repeat the denervation in step 286 by repeating steps a10 and a11 as needed until sufficient loss of sympathetic nerve activity is seen.

a12. Finish the renal denervation procedure in step 290 by standard methods at the end of a renal catheterization procedure.

In an alternative embodiment, the steps related to sensing nerve activity outside of the first artery (either in steps 276 or 288) can be replaced by steps which include stimulation of the nerves outside of the first artery as part of an assessment of the treatment in order to determine if the ablative treatment met a treatment criterion. For example, a surgeon could measure the change in blood pressure resulting from the stimulation in order to determine if the nerves were sufficiently ablated (where no evoked change in blood pressure, or other type of evoked response, might fail to be evoked when ablation was successful).

In an alternative embodiment, steps 270 to 280 can be followed by steps 286 to 290, whereby the first artery ablation therapy is assessed. Following successful treatment of the first artery the steps can be repeated for the second artery by performing steps 282 and 284 followed by steps 286 to 290, whereby the second artery ablation therapy occurs and is then assessed.

Finally, if insufficient drop in blood pressure is seen at follow-up several days, weeks, or years after the initial ablation occurred, the NSC 100 can be used to assess sympathetic nerve activity as a follow up diagnostic tool. For example, the NSC 100 can be used to assess whether nerve activity is below a threshold level of activity. For example, the threshold amount of activity can be defined based upon population normative criteria (with appropriate adjustment for gender, age, and medication) or the activity recorded at the beginning or end of the earlier procedure carried out on the patient and this comparison can determine whether repeat treatment is required.

Further, the NSC 100 can be used as a screening device to screen candidate ablation patients and assess whether they are suitable or unsuitable renal denervation candidates. The screening can occur before a renal denervation procedure to assess sympathetic nerve activity of a patient to determine if the patient is a good candidate for renal nerve ablation therapy. For example, the NSC 100 can be used to assess whether nerve activity is within some normal range (defined by looking at a lookup-table that corresponds to ranges of activity that have been found for patients who are successfully treated with ablation therapy) that has been found to indicate that ablation therapy may be successful. Additionally, the NSC 100 can be used as a screening device to screen candidate ablation locations. This may occur by obtaining a baseline of sensed data and evaluating the sensed data in order to determine if sufficient nerve activity is sensed at that location. For example, nerve density may vary with respect to how far the catheter is positioned within the arterial vessel. For example, the nerve density/distribution may vary as a function of the circumference of the artery, which tends to get bigger as one moves proximally along the renal artery. Further the target nerves may be clumped on one side of the artery rather than surrounding it in a relatively balanced manner. If the baseline nerve sensing at a first candidate ablation location does not record sufficient activity then the NSC (after the distal needles are retracted) may be moved to a second candidate location, or rotated, and then the activity can be sensed again. A comparison of the sensed data at the first candidate ablation location can be compared to that in the second candidate ablation location, and the surgeon can then use the result to determine the next step of the ablation procedure. The NSC 100 may also be used to stimulate the sympathetic nerves outside of a renal artery and the evoked change, for example, a change in blood pressure or other cardiac-related measure can be an indication of the patient's suitability for a renal denervation procedure.

FIG. 20b, shows the steps associated with the procedure using the PNASC 200 or 400 for the combination of renal denervation and subsequent assessment (e.g., via sympathetic nerve activity measurement with or without stimulation to time-lock a response from the patient) would include the following steps although not every step is essential and steps may be simplified or modified as will be appreciated by those of skill in this art:

a13. Flush the device to remove air from the lumens in step 470 which may include flushing the injection lumen with ablative fluid or an anesthetic such as lidocaine through the port 354 shown in FIG. 16 leaving ablative or anesthetic fluid in the dead space within the PNASC 200 or 400. Also flush all of the internal volumes of the PNASC 200 OR 400 with normal saline through the ports 344.

a14. Engage and position the device within the first renal artery, in Step 472, which can include inserting the PNASC 200 OR 400 through a previously placed guiding catheter, positioning the distal portion of the PNASC 200 OR 400 at the desired location in one patient's renal artery.

a15. Deploy the needles into/through the vascular wall in step 473, which can include depressing the button 332 shown in FIG. 16, and while holding the outer tube control cylinder 335 which is locked to the guide tube control cylinder 333, push the guide tube control cylinder 335 in the distal direction advancing the guide tubes 115 of FIG. 8 until the distal end of the guide tubes 129 come into contact with the inside wall of the renal artery limiting the advance of the middle tube 103 of FIG. 8 and deploying the guide tubes 115 from inside the tubular shafts 120 and out through the openings 131. The notch 331 will otherwise stop the distal motion of the guide tube control cylinder 333 when it engages the tube 344 at the maximum allowable diameter for the guide tubes 115. Release the button 332 which relocks the relative motion of the outer tube control cylinder 335 with respect to the guide tube control cylinder 333.

a16. Configure the sensing components and obtain sensed data in step 474, which can include depressing the button 342 that allows relative motion of the injection needle control cylinder 345 with respect to the guide tube control cylinder 333 and while holding the outer tube control cylinder 335 (which is now locked to the guide tube control cylinder 333) advance the needle control cylinder 345 with distal end 349 until the penetration limiting mechanism stops the motion and the preset depth L2 of the needles 169 or 189 with respect to the distal ends 129 of the guide tubes 115. There are two ways this can be done: 1) The distal end 349 of the needle control cylinder 345 is pushed forward until it engages the guide tube flush port 344 or 2) the internal gap 347 is closed against the proximal end of the gap adjustment cylinder 348 inside the needle control cylinder 345

Release the button 342, which relocks the motion of the needle control cylinder 345 to the guide tube control cylinder 333. This places the PNASC 200 or 400 in the configuration where the needles 169 or 189 with electrodes 164 or 174 penetrate through the internal elastic lamina (IEL) and penetrate to a preset distance (typically between 2 to 6 mm) beyond the IEL into the perivascular space outside of the media of the renal artery. The depth of 2-6 mm will minimize intimal and medial renal artery injury. After the electrodes are in an acceptable position then obtain sensed data and also process the data and display sensed data measurements to a surgeon. The sensing can also be used to confirm the position/depth of the needles in this step. For example, if the sensed data is too weak (e.g., the amplitude of the sensed nerve activity is small) then the surgeon may increase or decrease the depth of the needles in order to position these in an improved position for providing nerve ablation. Additionally, if the sensed nerve activity remains weak then the surgeon may retract the needles and move the catheter more distal or proximal or rotate the catheter before re-deploying the needles. In this second position the sensed data can again be evaluated in order to determine if the second candidate ablation location offers any advantage over the first. In this manner the surgeon can increase the likelihood that the needles are in a location with nerve activity (and possibly a greater density or more appealing distribution of nerves). This step 476 may therefore have a subcomponent set of steps that are related to selecting a promising ablation location/depth prior to carrying out the ablation to provide renal denervation.

Because the electrodes are situated outside of the media of the artery, nerves can be ablated without harming the media of the artery as compared with intraluminal RF ablation where direct contact of the electrode(s) with the intima can seriously damage the media.

a17. In step 476, attach the connector 360 to the external nerve activity measurement equipment and measure the amplitude or level of sympathetic nerve activity between at least one pair of electrodes 164 of FIG. 13, or electrodes 174 of FIG. 14. Alternately, if a common ground wire is included in the PNASC 200 or 400 or provided by a skin surface electrode then a measurement between a distal electrode and the common ground can be made. The level of nerve activity should be noted by the user and or might be saved in memory of the external equipment.

a18. Perform renal denervation in step 480, such as performing a renal denervation procedure on the first artery using the PNASC 200 of 400. If it is a chemical renal denervation procedure then a syringe or manifold with syringes (not shown) can be attached to the port 354 of FIG. 16 and the desired volume of ablative fluid is injected. The ablative agent which can be an ablative fluid, such as ethanol (ethyl alcohol), distilled water, hypertonic saline, hypotonic saline, phenol, glycerol, lidocaine, bupivacaine, tetracaine, benzocaine, guanethidine, botulinum toxin, glycosides or other appropriate neurotoxic fluid. This could include a combination of 2 or more neuroablative fluids or local anesthetic agents together or in sequence (local anesthetic first to diminish discomfort, followed by delivery of the ablative agent) and/or high temperature fluids (or steam), or extremely cold (cryoablative) fluid into the vessel wall and/or the volume just outside of the vessel. A typical injection would be 0.1 to 5 ml. This should produce a multiplicity of ablation zones (one for each injection needle 169 or 189) that will intersect to form an ablative ring around the circumference of the target vessel. The local anesthetic can be at injected at the primary site of injection of ablative fluid, distal or proximal to the primary site. There may be some advantages of injecting an anesthetic proximal to the ablation site.

If an energy-based renal denervation procedure is to be used one may still wish to inject a local anaesthetic first. Then the PNASC 200 or 400 would be connected to an appropriate source of electrical energy and the energy based renal denervation procedure would be performed using a stimulation protocol that is designed to be sufficient to provide an approximately circumferential ablation.

Use of proximal or distal anesthetic can also apply to prior art devices such as the PTAC of Fischell application Ser. No. 13/752,062. Contrast could be added to the injection either during a test injection before the neuroablative agent or during the therapeutic injection to allow x-ray visualization of the ablation zone. With ethanol, as an ablative agent, a volume of less than 0.6 ml is sufficient for this infusion as it will not only completely fill the needed volume including the sympathetic nerves, but is small enough that if accidentally discharged into the renal artery, would not harm the patient's kidneys. Ideally, a volume of 0.1 ml to 0.3 ml of ethanol should be used. The amount used could be the same for all renal arteries or it could vary depending on the diameter of the renal artery into which the ethanol is to be injected. The agrophobic, hygroscopic and lipophilic nature of ethanol enhances the spread allowing such a small volume to be effective. It is desirable to fluoroscopically verify the deployment of the needles 169 or 189 of FIGS. 13-14 into the vessel wall of the target vessel before injecting the ablative agent or fluid.

A19. Access the ablation treatment in step 482, such as after waiting up to 30 minutes for the ablative fluid to affect the nerves or the heat from the energy based denervation to dissipate, measuring the nerve activity across at least one interval after the selected post-ablation duration has occurred and compare the post-ablation sensed activity to a selected value (prior baseline activity of the patient, population normative threshold value, etc. as has been disclosed) in order to assess the difference in nerve activity between before and after the renal denervation procedure. The difference can be assessed in relation to at least one treatment criterion in order to determine the effectiveness of the renal derivation. Based upon the sensed data failing to meet the treatment criterion (e.g., if insufficient decrement of nerve activity is seen) then repeat steps 8 and 9, and if the assessment meets the treatment criterion then the ablation was effective and move to step 484.

a20. Once sufficient nerve damage is determined, in step 484 the sensing/stimulation components (e.g., needles and guide tubes) are retracted into the device, such as by depressing the button 342 of FIG. 16 and while holding the outer tube control cylinder 335, pull the needle control cylinder 345 back in the proximal direction until the injection needles 169 or 189 are fully retracted back into the guide tubes 115. Release the button 342 locking the motion of the injection needle control cylinder 345 to the guide tube control cylinder 333.

Then depress the button 332 releasing the relative motion of the outer tube control cylinder 335 with respect to the guide tube control cylinder 333 that is now locked to the injection needle control cylinder 345. Retract in the proximal direction the guide tube control cylinder 333 with respect to the outer tube control cylinder 335. This will retract the guide tubes 115 of the configuration of FIG. 9 back inside the openings 131 in the outer body extension 104 the PNASC 200 OR 400.

In step 484 Retract the PNASC 200 OR 400 back into the guiding catheter 140.

a21. If in step 485, both arteries have been treated, go to a21 and step 490 to finish the procedure. Otherwise, in step 488, move the guiding catheter 140 to the other renal artery and advance the PNASC 200 or 400 into position. Repeat steps 473 through 484 for the other renal artery.

a21. In step 490, finish the ablation procedure such as by removing the guiding catheter with the PNASC 200 OR 400 from the body.

Fischell et al U.S. Pat. No. 8,740,849 discloses multiple techniques for use of saline pre and intermediate flushing of the injection lumens of the PTAC 100 which can also be used here.

While the buttons 332 and 342, as described above, release the motion of control cylinders when depressed and lock when released, it is also envisioned that they could also be interlocked as follows:

1. The first interlock allows the injection needle control cylinder 345 to be unlocked only when the guide tube control cylinder 333 is in its most distal position where the outer tube 102 is pulled back and the guide tubes 115 are fully deployed.

2. The second interlock allows the guide tube control cylinder 333 to be unlocked only when the injection needle control cylinder 345 is in its most distal position where the needles 169 or 189 are retracted within the guide tubes 115.

These same interlocks can be applied to the NSC 10 or 100 of FIGS. 1-12. However, the interlocks can be advantageous in some embodiments when associated with the injection of a neurotoxic ablative fluid.

The combination of the buttons 332 and 342 with the control mechanisms described above should make the use of the NSC 10 or 100 and the PNASC 200 or 400 reasonably simple and straight forward. The operator basically presses button 332 and pushes the guide tube cylinder 333 forward causing the guide tubes 30 or 115 to expand outward, then presses button 342 and advances the needles 23, 119, 169 or 189 forward to penetrate the wall of the renal artery. Nerve activity measurements and/or injections are performed then the reverse procedure is done with button 342 depressed and the needles 23, 119, 169 or 189 retracted, then button 332 is depressed and the guide tube cylinder 333 is retracted in the proximal direction retracting the guide tubes 30 or 115 within the body of the catheter.

While a push-button activated handle where sections are pushed and pulled in the longitudinal direction to cause guide tube and needle deployment is shown in FIG. 16, it is envisioned that other techniques such as rotational mechanisms for locking or longitudinal motion can also be used. The Fischell et al U.S. patent application Ser. No. 13/643,070 filed Oct. 23, 2012, which is hereby incorporated by reference in its entirety, shows such a rotational locking mechanism in FIG. 33.

It should also be noted that in one variation of the procedure having the cap 356 locked onto to the fitting for the injection port 354 prior to placing the PNASC 300 or 400 into the patient's body will certainly prevent any ablative solution from entering the renal artery during insertion of the PNASC 200 or 400 into the renal artery. Additionally, replacing that sealing cap 356 onto the fitting for the injection port 354 as the PNASC 200 or 400 is moved from one renal artery to the opposite renal artery will also prevent any ablative solution from entering the second renal artery.

The cap 356 would also be locked onto the fitting for the injection port 354 as the PNASC 200 or 400 is removed from the patient's body. During the renal denervation procedure, the cap 356 would be removed only to inject ablative solution into the perivascular space of the treated vessel.

A stopcock attached to the port 354 could also be used such that when closed, it would prevent leakage of ablative fluid out of the needle distal openings of the PNASC 200 or 400. In reality of course, if there were no cap 356 attached as the PNASC 200 or 400 is moved within the arterial system of the body, the blood pressure within the arterial system would if anything force any fluid within the injection lumens of the PNASC 200 or 400 back out of port 354.

The NSC 100 and the PNASC 200 or 400 can be packaged with the guide tubes 30 or 115 and the sensor tube 20, 116, 152, 162 or 172 fully extended. The reason for this is that the preferred embodiment of the guide tubes are made from plastic such as polyimide formed into a curve shape. Such a plastic material may lose its shape over extended periods of time if it were packaged retracted back into the tubular shaft 21 or 120 which would straighten it. In this case, the device would be shipped in a protective packaging to ensure handlers do not receive needle sticks.

It is also possible to ship the device with the needles 23, 119 159, 169 or 189 retracted within the guide tubes 30 or 115 for safety. The guide tubes could be coated with a brightly colored dye or formed from a material that is brightly colored in order to serve as a visual deterrent when the needles are in their deployed position.

While this specification has focused on use of the NSC 100 and the PNASC 200 or 400 for use in the measurement of nerve activity outside of the renal artery, it is also clearly envisioned that the apparatus and methods of FIGS. 1-16 inclusive can be applied to measure electrical activity outside of any vessel or duct of the human body and in the case of the PNASC 200 or 400, inject any fluid for any purpose including that of local drug delivery into a specified portion of a blood vessel or the volume of tissue just outside of a blood vessel, or into prostatic tissue via the prostatic urethra. For example these devices could be used to assess electrical activity in the wall of the left atrium outside of the Pulmonary vein, and ablate the tissue there to diagnose and treat atrial fibrillation. It could also be used to assess nerve activity around a pulmonary artery, to assist in the treatment of pulmonary hypertension.

While the embodiments shown in FIGS. 1 through 16 show three distal electrodes, the presently disclosed structure can also be applied to designs with one needle, two needles or 4 or more needles.

FIG. 21 is a block diagram of the external electronics equipment 500 with power supply 522. The wires 361, 362 and 363 that exit the handle 300 of the NSC/PNASC of FIG. 16 terminate in the connector 360. The connector 360 connects to the connector 560 of the electronics 500 providing electrical conductivity from the NSC/PNASC wires 361, 362 and 363 to the wires 561, 562 and 563 respectively of the electronics 500

The wires 561, 562 and 563 connect to each of the amplifiers (each of which may have high, low, notch filters, and/or band pass filters) of the 3 A-D converters 521, 522, 523. The amplifiers can be referenced to a common ground 511, 512 and 513 respectively. Alternatively, although not shown here, the amplifiers can be differential. For example, wires 561 and 562 can be routed to differential inputs of a first amplifier (in one embodiment 563 can serve as ground or a separate wire attached to the subject can serve as com/ground). In other embodiments, 562 and 563 can be routed to the second amplifier, and 561 and 563 to the third amplifier. In this manner it is possible to provide 3 differential amplified signals. Further, a multiplexor may be used to route the different signals to different amplifiers. The routing can occur in a user selected manner (e.g. by adjusting a controller that determines the electrode montage, or can be controlled according to a sensing protocol implemented by the processor 540. In addition to the amplification shown in the figure further amplification modules may be incorporated into the circuitry such as isolated amplifiers, and pre-amplifiers).

The amplified signals from the amplifiers 511, 512 and 513 are converted to digital signals by the analog to digital converters 521, 522 and 523 respectively. The digital signals from the analog to digital converters 521, 522 and 523 are stored in the circular First-In-First-Out Buffers 531, 532 and 533 respectively that are read by the Central Processing Unit (CPU) 540 with RAM 542 and program memory 545.

In one embodiment the amplification and signal processing can be achieved using commercially available bioamplifiers and data acquisition systems (e.g. a Model 15LT Bipolar Portable Physiodata Amplifier System operating in conjunction with a national instruments NI USB-6212 BNC multifunction data acquisition unit or AD Instruments Bio Amps operating with a Powerlab system for recording extracellular potentials) which feed into a computer that is operating as part of the electronics equipment. The CPU is connected to a Visual display 520 and a sonic transducer or loudspeaker 547 and receives input from a button touchpad 550 or touch sensitive screen of the visual display. The visual display 520 may be as simple as a set of LEDs or it can be a full graphic display such as an LCD screen of a laptop, tablet or smartphone. The button touchpad can be a limited or custom set of buttons or a full numeric or alphanumeric (e.g. QWERTY) keyboard for obtaining user input.

A clock/timing circuit 549 provides timing for the electronics 500 including the analog to digital converters 521, 522 and 523, the FIFO buffers 531, 532 and 533 and the central processing unit (CPU) 540. The electronics 500 can be connected to a computer(s), equipment, accessories and electronic systems through the wired Input/Output (I/O) port 570, for example an RS-232 serial port or USB 1, 2, or 3 type port. The wired Input/Output (I/O) port 570 can also be used to obtain input from an amplifier that senses patient data from one or more electrodes or other sensor located outside of the patient (e.g., ECG or blood pressure meter). A wireless I/O sub-system 575 is also connected to the CPU 540 allowing wireless communication to and from other electronics, computer systems, and wireless local area network of a hospital, for example a Bluetooth or Wi-Fi protocol wireless circuit may be used.

The RAM 542 includes the storage for baseline data 544 and "current" nerve activity sensed data 546 that are captured at points during the ablation procedure. The data can include raw waveforms summary, and trend data. The RAM 542 can also contain as well as program protocols (for providing stimulation, sensing, or ablation), parameter values, criterion used during the treatment, and other values for settings that are used during screening, processing sensed data, and assessment of sensed data as can occur for the detection of significant changes in nerve activity indicative of effective denervation. The values of the RAM can be accessed by the stimulation subsystem 580 or the sensing subsystem which is realized, at least in part, by the combination of amplifiers, A-to-D converters, FIFO buffers, and CPU.

A Hard Disk (HD) or Solid State Disk (SSD) provides non-volatile data storage for the electronics 500 including recorded nerve activity and pre-set programs for operation.

A stimulation sub-system 580 contains signal generators related to providing stimulation and/or ablation signals and is controlled by the CPU 540. The stimulation sub-system 580 is connected to the wires 561, 562 and 563 that are in turn connected through the connectors 560 and 360 to the wires 361, 362 and 363. The connections of wires from the stimulation sub-system to the wires 561,562,563 can include multiplexor circuitry and other electronics in order to isolate and/or protect the amplifiers 511,512,513 during the provision of stimulation and/or ablation. This allows the stimulation sub-system to provide electrical energy for energy based ablation. In one configuration, the stimulation sub-system 580 would deliver the electrical energy sequentially to pairs of wires. In another embodiment, the sub-system 580 would deliver energy between any individual pair of the three electrodes 117 of FIG. 7, two of the three electrodes to the third as a reference return electrode or any combination of the three electrodes to a common reference return electrode either using a skin surface electrode or a portion of the catheter such as the guide wire 110.

The electrical energy delivered to a patient may take different forms. In a preferred configuration, the stimulation sub-system 580 may generate RF energy as is now used by devices such as the Medtronic Simplicity device. For the PNASC 600 embodiment of FIG. 17 with ultrasound energy delivery, the stimulation sub-system 580 would provide the electrical energy to drive the ultrasound transducer 650.

The wired I/O port 570 and/or wireless I/O port 575 may allow for another stimulator (not shown) to be used under control of the CPU 540 with the electronics 500 used for sensing only. The ports 570 and 575 also can be used to control an external pump that may be further configured to heat or cool a liquid such as saline, so that a temperature controlled liquid can be provided to the proximal section of the PNASC 200/400 of FIG. 13 or 14 for chemical or heated or cooled fluid delivery for renal denervation.

Additionally, rather than stimulators, the ports 570 and 575 can be connected to systems of sensors to record data related to, for example, ECG, heart rate, or blood pressure. This may be essential as time-locked nerve activity measurement may require synchronization with the heartbeat.

The electronics 500 would typically connect to the wires 361, 362 and 363 connected to distal PNASC electrodes for both stimulation and sensing at different moments in time. It is also envisioned that stimulation and sensing could occur simultaneously. For example, using wire 561 as a common, stimulation could be provided to wire 562 with sensing from wire 563. This would typically be a stimulation signal followed by sensing although it is envisioned that simultaneous stimulation and sensing would be possible.

Figure 22:
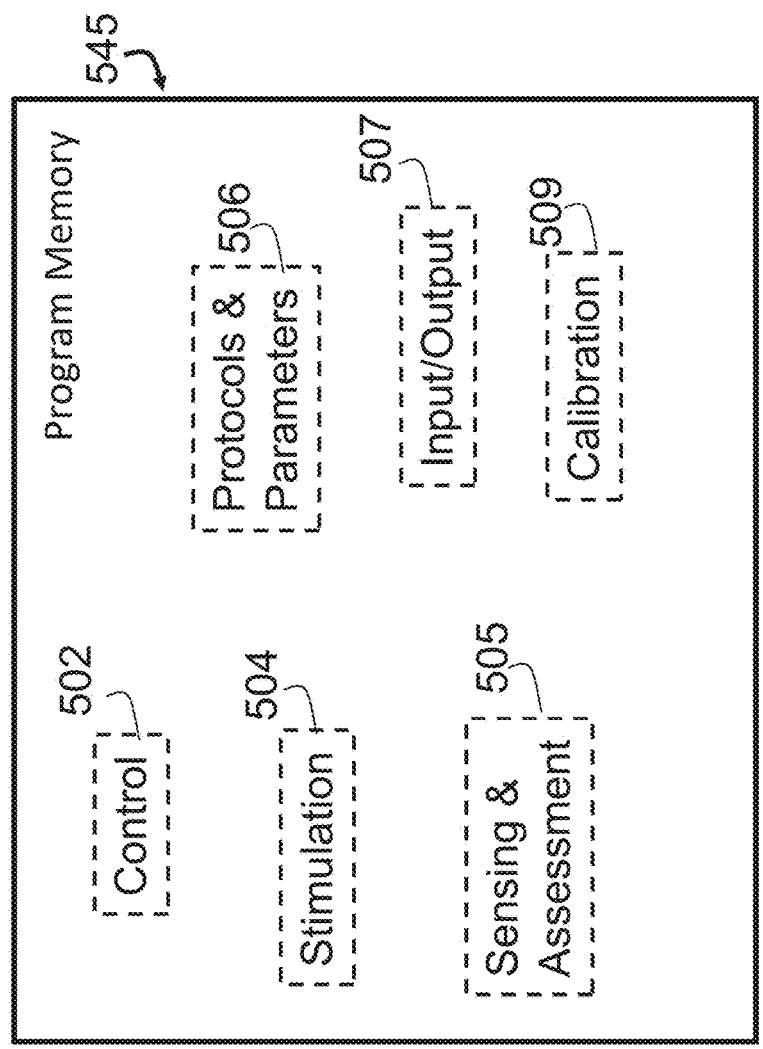
FIG. 22 shows the modules through that may be included in the program memory of the electronics.

FIG. 22 shows the modules 504 through 524 that may be included in the program memory 545 of the electronics 500.

The modules contain software, electronics, and/or firmware, for accomplishing the functions disclosed. Modules can share resources and be controlled by other modules or components. The electronics system 500 includes a control module 502 for controlling the overall function of the electronics 500. The stimulation module 504 provides control of the stimulation sub-system 580 for providing electrical stimulation and/or energy based ablation through the electrodes such as the electrodes 117 of FIG. 7 that are positioned beyond the interior wall of the renal artery for the renal denervation application. The stimulation module 504 control of the stimulation sub-system 580 of FIG. 21 controls the generation of stimulation signals which can include RF signals, pulses, or arbitrary waveforms for output including alternating current (AC) and/or direct current (DC) signals to be used by electrical, stored in the protocols and parameters module 506. Treatment protocols that are stored in the protocols magnetic, optical, sonic, ultrasonic or other types of stimulators that are provided within catheter device with which it is configured to operate.

The sensing and assessment module 505 (which may also be termed a sensing subsystem) provides control for the measurement of nerve activity collected by the CPU 540 from signals coming through the amplifiers 511, 512 and 513, A to D converters 521, 522 and 523 (which can include analog or digital filtering, processing, additional amplification, isolation, and safety circuitry) and FIFO Buffers 531, 532 and 533. The sensing and assessment module 505 controls the comparison of current nerve activity stored in the RAM 542 (e.g., in the RAM portion 546) with reference values or data such as previously recorded baseline nerve activity (e.g., stored in RAM location 544). The module 505 can determine if one or more selected treatment criteria have been met or not and therefore determine whether one of effective nerve ablation or ineffective nerve ablation has occurred. The Control module 502 can operate both stimulation module 504 and sensing module 505 according to treatment protocols and parameters and parameters module 506 can include nerve stimulation protocols, sensing protocols, ablation protocols, and evaluation protocols that enable the electronics system 500 to allow a medical practitioner to responsively adjust the catheter system operation in relation to the evaluation of sensed data, doctor input, time intervals, detection of events, and other triggers that can cause the selection, provision, and adjustment of therapy. In one embodiment, the control module can operate in a semi-automatic or fully automatic closed-loop manner to adjust the ablation treatment provided based upon the assessment of sensed data.

The sensing and assessment module 505 can also be used to calculate various quantitative measurements that can be derived from sensed data. The assessment of sensed data may also include allowing a user to retrieve and display at least one of raw, summary, and trend results of sensed data for a patient that were collected at different moments in time. Assessment of data and modification of the ablation treatment may occur in a closed loop manner in which the stimulation is adjusted in relation to an evaluation of sensed data. Additionally or alternatively such assessment may cause information (information about the sensed data) or status signals displayed on the visual display 52 of FIG. 21 to be presented to a user of the electronics system 500. Sensing circuitry and sensors can be configured to allow the catheter system to measure such aspects as temperature. For example, at least one thermocouple or other temperature sensor for measuring the temperature of the monitored tissue or of the RF energy delivery element can be provided at the distal tip of the catheter. The catheter system can be configured to acquire temperature or impedance measurements inside of, along, within, or outside of the wall of the vessel that is in the vicinity of the treatment target area.

Nerve stimulation can include stimulation that is provided, for example, in order to assess evoked cardiac activity or evoked activity of the sympathetic nerve that is triggered by stimulation or may include electrical nerve ablation such as RF ablation or electrocautery. The stimulation protocol can determine which of one or more stimulators or sensors on the catheter are used for stimulating, ablation, and sensing. The electronics system 500 can also simply provide stimulation, ablation, or sensing under the manual control of a doctor. The control module 502 has access to the clock/timing sub-system 549 including a real time clock and a timer.

The protocols module 506 can include, for example, a subroutine for processing data as part of steps such as step 288 of FIG. 20a. For example, sensed data can be evaluated according to at least one treatment criterion, and if the criterion is passed then the ablation procedure is finalized, and if the treatment criterion is not passed, then ablative stimulation is adjusted, repeated, or otherwise provided, as defined by the treatment protocol as per step 286 of FIG. 20a.

In one embodiment a characteristic of the sensed data is evaluated before and after treatment in order to determine if a reduction in the characteristic has occurred due to therapy. In one embodiment the characteristic is the peak (or mean) amplitude or frequency of energy within at least one selected frequency range, and reflects the energy within a selected frequency band. The energy may be assessed by providing at least one band-pass, low-pass, or high-pass filter implemented with digital signal processing and allows the CPU 540 of FIG. 21 to filter the sensed data prior to its measurement of nerve activity. A ratio may be calculated related to energy in a first frequency range (spectral band) compared to energy in a second band.

In another embodiment, the CPU 540 can perform spectral analysis on the data to derive frequency, time-frequency, or time-locked time-frequency results. In yet another embodiment, a signal characteristic can be measured for 2 or more electrodes and can assess inter-electrode coupling. For example, prior to ablation the sensed data sensed from 2 or more electrodes may be more largely correlated due to the nerve signals being transmitted along the renal artery. After successful ablation a decrease in the post-ablation correlation or coherence (for one or more frequency ranges) should decrease relative to the baseline correlation or coherence. Successful ablation can be defined to have occurred when at least one characteristic of the sensed activity related to an absolute activity level, a relative activity level (e.g., compared to baseline), or activity differences between 2 or more electrodes (e.g. decrease in coherence or correlation) meets at least one defined treatment criterion. The one or more characteristics of the sensed data can be displayed by the visual display 520 to the user, and a history of values for the characteristic(s) can be stored by the CPU 540 in the RAM 542 or permanently in the SSD/HD 590.

There are numerous scientific articles describing methods of measurement of nerve activity but for this application, the display 520 may show a digital display of one or more electrical characteristics such as the peak voltage, average voltage, peak power and/or average power of sensed nerve activity. The difference (or ratio) in measurements before and after the renal denervation procedure can be used to assess the effectiveness of the procedure. Of these average voltage would be a preferred measurement.

The display 520 could provide a graphical display of the actual sensed signals as well as means to select which pair of electrodes is being used to derive a bipolar signal that is displayed. For example, using the button touchpad 550, control can be provided to enable a user to choose electrodes pair derivations such as 1-2, 2-3 or 3-1 would be desirable. This would have electrode 1 corresponding to wire 561, electrode 2 to wire 562 and electrode 3 to wire 563.

Monopolar derivations where electrode 1 is referenced to an electrode located distally within a patient could also allow electrical activity to be localized to a more specific degree since the active electrode recording the activity would reflect nerve activity and the reference electrode would not.

A calibration module 509 allows a user in to normalize the signal level during initial measurement of sympathetic nerve activity and capture the baseline nerve activity signal and thus establish the baseline activity level stored in the RAM portion 544 of FIG. 21.

In one embodiment, the visual display 520 would include 5 LEDs that could be activated to show maximum activity at the time of calibration/baseline recording. Following the renal denervation procedure, the user could operate the electronics module to cause a post-therapy measurement to be obtained. The reduction in nerve activity between the pre-therapy measurement and the post-therapy measurement would be displayed by illumination of the new level compared to the normalized value.

For example, if the post denervation level is 40% of the normalized level for one of the sensors, then only 2 of the 5 LEDs would be lit showing a 60% drop in nerve activity. An example of even simpler version would have the visual display 520 include a green, yellow and red LED for various sensors, wherein this example, green indicates normal nerve activity, yellow indicates a partial reduction and red indicates a significant reduction. A more complex embodiment could use the baseline as a "control" level of activity and then calculate the average activity over a specified measurement time interval. The measurement protocol stored in the module 506 could then be configured to compare the sensed activity over a similar duration of nerve activity measurement which occurs after ablation therapy. The visual display 520 using an alphanumeric of full graphical display can be configured to display a quantitative, numerical reduction value (e.g., "Nerve activity reduced by 64% compared to baseline nerve activity.")

A sensed data characteristic can be related to a measured neurogram. A neurogram may be obtained by analog means by sending the sensed neural activity through a band pass filter (e.g., band-width, 700-2,000 Hz) and then a resistance-capacitance integrating network (e.g., time constant, 0.1 second) to obtain a mean voltage waveform. A digital signal processing equivalent to this can also be performed by the CPU 540 according to a digital signal processing protocol stored in the module 506. The neurogram may be processed to represent the average envelope of the response in order to measure amplitude, burst rate, and other measures as is well known.

In addition to ongoing activity, the sensed data can reflect evoked activity recorded in response to an evoking stimulus such as electrical or pharmaceutical stimulation, or other evoking stimulus.

The sensed data can also be evoked by a change in the patient's state. For example, the patient state can be adjusted by raising and lowering blood pressure as can occur by providing vasoactive drugs to the patient. Either the baseline or post-ablation activity, or both, may be taken with blood pressure being higher or lower than might otherwise occur in the patient, in the absence of such intervention.

In an embodiment, re and post assessment of patients can be adjusted based upon patient characteristics. For example, patients can be divided into two groups based upon high or low basal microvolt levels of renal sympathetic nerve activity. Assessment for the two groups may then occur differently. For example, patients with high basal microvolt levels of activity may have their baseline taken without intervention, while a low basal microvolt level patient may be assessed after drug exposure to increase activity during at least one of the baseline or post-ablation period.

One measure of neural activity that may be assessed, is peak burst height (or maximum voltage) which can reflect the number of active fibers in renal sympathetic nerve activity (RSNA) or synchronized RSNA. This measure may reflect residual nerve activity better than any post-ablation changes in average rhythm/burst rate/frequency over time, or peak frequency of the nerve activity. Nonetheless both amplitude and frequency of the activity (e.g., bursts) may be used to assess post-ablation nerve activity change relative to the pre-ablation baseline or relative to a threshold which defines successful therapy. Peak duration is influenced by the firing synchrony and the dispersion of the mass discharge due to different conduction velocities of the multiple renal nerve fibers. Peak duration, or averaged peak duration, may also be used to assess post-ablation changes in nerve activity.

Other measures can also include: average voltage; bursts/min; average burst count; average burst amplitude; assessment of cyclical signatures; integrated and/or rectified renal sympathetic nerve activity (SNA); "leaky" or resetting integrators to integrate over time or up to a defined threshold; amplitude at a spectral frequency range associated with nerve activity; and, time locked activity recorded in response to an evoking stimulus such as at least one a drug or external electrical stimulus or internal electrical stimulus such as the ECG signal or non-electrical stimulus such as oscillation of arterial pressure. Of course any of these measures can be normalized to baseline.

Correlation measures of recorded sensed data can also be obtained. Correlation may be accomplished between two electrodes and may be further processed according to cardiac data sensed by sensors located external to the patient. For example, correlation may also be calculated to assess association between heart beats, heart rates, and bursting patterns.

The SSD/HD 520 of FIG. 21 may be configured to store a historical record in order to summarize, track, and store the ablation treatment that was provided and sensed data that was obtained which may be especially helpful evaluating what occurred during therapy.

The input/output module 507 works in conjunction with the control module 520 for presenting information to a user (e.g. physician) through the visual display 520 and/or sonic transducer 547 of FIG. 21 and obtaining information/input from the user through the touchpad 550 or touch sensitive display, when provided. In addition to data, the visual and sonic transducers can present the user with alarms or notification related to the provision of therapy (e.g., a timer can be shown on the screen or an audio-sound can be related to a measurement of sensed activity, such as presenting a pitch that varies with the amount of sensed nerve activity). While not shown in FIG. 21, although the electronics system 500 may communicate in a wired or wireless manner with, or be realized within, a specialized device, smartphone, laptop, or tablet computer the specialized device containing a visual display and loudspeaker. The device 500 can also contain user interface module 524 which interacts with user controls 525 such as nobs, switches, etc. to allow a user to provide input, such as through a menu guided system, as well as adjust operation of the device by manually adjusting nobs related to the operation of the device.

Both the control module 502 and the waveform generator module 512 may be configured with safety hardware and software routines, including calibration routines to calibrate the apparatus 500 and to ensure proper functioning.

The modules and components described for the apparatus 500 of FIGS. 21 and 22 are for illustration purposes only and the device used by the system of embodiments of the present invention can be realized with less than or more than the modules and system components described herein.

It is also envisioned that rather than conducting wires, that optical fibers may be used for signal conduction through the catheter and for delivery of laser based ablation for the nerve fibers. It is also envisioned that a solid state laser instead of an electrode could be located at the distal portion of the catheter to turn electrical energy into light for ablation. Such a laser could also be located in place of the ultrasonic transducer 650 of FIGS. 17 and 18 that could then send optical signals for ablation through optical fibers that would replace the wires 616.

It is also envisioned that the sensing capabilities of the NSC and PNASC presented here may have, in some embodiments, an important additional method of use. Specifically, the level of sympathetic nerve activity seen in the perivascular space may be indicative of whether the patient's hypertension is sympathetically driven. This would allow the clinician to decide whether denervation should be performed as well as providing a baseline against which the post-denervation nerve activity can be compared. It could also facilitate the choice of denervate vs. medicate and if medication is to be chosen, which medication would be best for non-sympathetically driven hypertension.

Various other modifications, adaptations, and alternative designs are of course possible in light of the above teachings. Therefore, it should be understood at this time that within the scope of the appended claims the invention may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "sensing nerve activity using a catheter" include "instructing the sensing of nerve activity using a catheter." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A method of modulating nerve activity, comprising:
positioning a distal portion of a catheter within a renal vessel;
advancing a first needle guiding element and a second needle guiding element outward from the catheter toward an inside surface of the renal vessel;
advancing a first needle and a second needle through the first needle guiding element and second needle guiding element, respectively, and into a peri-vascular space outside of the inside surface of the renal vessel, wherein a distal end of the first needle guiding element and a distal end of the second needle guiding element are configured to maintain their position against the inside surface of the renal vessel as the first needle and the second needle advance into the peri-vascular space; and
operating the catheter to provide at least one modality of neurolysis to nerves located in the peri-vascular space or to sense nerve activity from at least one of the first and second needles.

2. The method as in claim 1, wherein the at least one modality of neurolysis includes injecting an ablative fluid through the first needle and the second needle to form two ablative fluid zones in the peri-vascular space.

3. The method as in claim 2, wherein the ablative fluid injected from each needle into the peri-vascular space travels circumferentially forming one zone for each needle where the zones approximately intersect to form a ring of neurolysis.

4. The method as in claim 2, wherein injecting the ablative fluid comprises injecting ethanol.

5. The method as in claim 1, wherein the at least one modality of neurolysis includes providing ablation of nerves using energy delivered by at least the first needle.

6. The method as in claim 5, where the energy delivered is in the radiofrequency spectrum.

7. The method as in claim 5, where the energy delivered includes providing ultrasonic ablation from an ultrasound transducer.

8. The method as in claim 1, further including evaluating nerve activity by comparison to a treatment criterion.

9. The method as in claim 5, wherein operating the catheter to sense nerve activity uses a return that is provided by at least one of: the second needle, an electrode on the skin of the patient, or an electrode on the catheter.

10. The method as in claim 1, wherein operating the catheter to sense nerve activity includes sensing nerve activity during two or more periods of time separated by at least 30 seconds.

11. The method as in claim 10, where the two or more periods of time include a first period of time before ablation and a second period of time after ablation.

12. The method as in claim 1, wherein the catheter includes a third needle, wherein operating the catheter to sense nerve activity includes sensing nerve activity between the first needle and the second needle, between the first needle and the third needle, or between the second needle and the third needle.

13. The method as in claim 1, including evaluating the quality of neurolysis by comparison of the nerve activity to a pre-set criterion.

14. The method as in claim 1, wherein operating the catheter to sense nerve activity further includes sensing nerve activity between at least two needles.

15. A method of modulating nerve activity, comprising:
positioning a distal portion of a catheter within a vessel of a human patient;
advancing at least a first needle guiding element and a second needle guiding element outward from the catheter toward an interior wall of the vessel;
advancing at least a first needle and a second needle through the first guiding element and the second needle guiding element and into a peri-vascular region outside of the interior wall of the vessel, wherein a distal end of the first needle guiding element and a distal end of the second needle guiding element are configured to maintain their position against the interior wall of the vessel as the first needle and the second needle advance into the peri-vascular region;
wherein the catheter is configured to provide at least a first modality of neurolysis to nerves located in a peri-vascular region of the patient or sense nerve activity from at least one location in the peri-vascular region.

16. The method as in claim 15, further including using external equipment to provide a measurement of nerve activity.

17. The method as in claim 16, wherein the measurement of nerve activity is used to determine the efficacy of the first modality of neurolysis.

18. The method as in claim 17, wherein at least part of the method is repeated if the level of neurolysis is insufficient.

19. The method as in claim 15, where a second modality of neurolysis is applied, wherein the second modality of neurolysis is different from the first modality of neurolysis.

20. The method as in claim 16, wherein a visual display is used to provide the measurement of the nerve activity.

21. The method as in claim 16, wherein the measurement of nerve activity includes a measurement of one or more of:
spike count,
mean burst frequency,
peak burst frequency,
power within at least one spectral band, and
a normalized measurement of nerve activity which compares nerve activity after injection to nerve activity before injection.

* * * * *